United States Patent [19]
Capage et al.

[11] Patent Number: 5,559,015
[45] Date of Patent: Sep. 24, 1996

[54] RECOMBINANT-DNA MEDIATED PRODUCTION OF XANTHAN GUM

[75] Inventors: Michael A. Capage; Daniel H. Doherty; Michael Betlach; Rebecca W. Vanderslice, all of Boulder, Colo.

[73] Assignee: Getty Scientific Development Company, Houston, Tex.

[21] Appl. No.: 352,216

[22] Filed: Dec. 2, 1994

Related U.S. Application Data

[63] Continuation of Ser. No. 815,615, Jan. 7, 1992, abandoned, which is a continuation of Ser. No. 333,868, Apr. 3, 1989, abandoned, which is a continuation of Ser. No. 188,687, Apr. 27, 1988, abandoned, which is a continuation of Ser. No. 29,530, Mar. 23, 1987, abandoned, which is a continuation-in-part of Ser. No. 844,332, Mar. 26, 1986, abandoned.

[51] Int. Cl.$^6$ .............. C12P 19/06; C12N 1/21; C12N 15/70; C12N 15/74
[52] U.S. Cl. ............ 435/104; 435/252.3; 435/252.33; 435/257.34; 435/320.1
[58] Field of Search .................. 435/104, 172.3, 435/252.3, 252.34, 320.1, 252.33

[56] References Cited

U.S. PATENT DOCUMENTS

| | | | |
|---|---|---|---|
| 4,329,448 | 5/1982 | Cox et al. | 536/123 |
| 4,357,423 | 11/1982 | Cox et al. | 435/101 |
| 4,407,951 | 10/1983 | Weisrock et al. | 435/104 |
| 4,713,449 | 12/1987 | Vanderslice et al. | 536/123 |
| 4,868,293 | 9/1989 | Vanderslice et al. | 536/123 |

FOREIGN PATENT DOCUMENTS

| | | | |
|---|---|---|---|
| 66961 | 12/1982 | European Pat. Off. | C12P 19/06 |
| 0233019 | 8/1987 | European Pat. Off. | |

OTHER PUBLICATIONS

Karn et al., Proc. Nat'l. Acad. Sci U.S.A., 77:5172–5176 (1980).
Wood et al., J. Bacteriol 14:1448–1451 (1981).
Ditta et al., Proc. Nat'l Acad. Sci U.S.A., 77:7347–7351 (1980).
Turner et al., Mol. Gen. Genet., 195: 101–107 (1984).
Ruvkun et al., Nature 289: 85–88 (1981).
Ohman et al., J. Bacteriol, 162:1068–1074 (1985).
R. P. Silver et al., Nature, 289: 696–698 (1981).
S. K. Kadam et al., J. Bacteriol., 161: 277–284 (1985).
A. Darzins et al., J. Bacteriol., 159: 9–18 (1984).
A. Darzins et al., J. Bacteriol., 161: 249–257 (1985).
J. B. Goldberg et al., J. Bacteriol., 158: 1115–1121 (1984).
S. Gottesman et al., J. Bacteriol., 162: 1111–1119 (1985).
R. C. Goldman et al., J. Bacteriol., 163: 256–261 (1985).
Silver et al., J. Bacteriol., 157: 568–575 (1984).
Darzins et al., J. Bacteriol., 164: 516–524 (1985).
Daniels et al., The EMBO J., 3: 3323–3328 (1984).
Engebrecht et al., Proc. Nat'l Acad. Sci. U.S.A., 81:4154–4158 (1984).
Enseley et al., Science, 222: 167–169 (1983).
Malpartida et al., Nature, 309: 462–464 (1984).
Fishel et al., Develop. Biol., 110: 369–381 (1985).
Couto et al., J. Biol. Chem., 259: 378–382 (1984).
Creeger et al., J. Biol. Chem., 254: 804–810 (1979).
Harding et al., "Genetic and Physical Analysis of Cloned Xanthan Gum Biosynthetic Genes from *Xanthomonas campetris*," Abstracts of the Annual Meeting, No. 272 (1986), 0–64.
Barrere et al. (Dec. 1986) Int. J. Biol. Macromol.: 372–374.
Okita et al. *J. Biol. Chem.* 256 (13):6944–6952, 1981.
Joyce et al. *J. Biol. Chem.* 257 (4): 1958–1964, 1982.
Gay et al. *J. Bacteriol.* 153 (3): 1424–1431, 1983.
Ditta et al. *Plasmid* 13: 149–153, 1985.

Primary Examiner—Mindy Fleisher
Assistant Examiner—Philip W. Carter
Attorney, Agent, or Firm—Finnegan, Henderson, Farabow, Garrett & Dunner, L.L.P.

[57] ABSTRACT

Methods for the recombinant-DNA mediated production of xanthan gum and gum variants structurally related to xanthan are disclosed. The methods in part involve the synthesis of these polysaccharides in anaerobic and/or denitrifying hosts.

In particular, plasmids pX209 and pRK290-H366 are disclosed which contain the genes, isolated from *X. campestris*, encoding Transferase I, Transferases II, Transferase III, Transferase IV, Transferase V, Ketalase, Acetylase and Polymerase. These plasmids have been deposited in the American Type Culture Collection under Accession Nos. 67051 and 67049, respectively.

48 Claims, 64 Drawing Sheets

FIG. 2.
BamHI RESTRICTION MAPS OF LAMBDA 1059 CLONES SELECTED BY HYBRIDIZATION WITH X655

| CLONE DESIGNATION | BamHI FRAGMENTS |
|---|---|
| B  | 2.2, 3.5, 1.35, 1.0 |
| D  | 1.5, 4.7, 2.2, 3.5 |
| F  | 1.4, 1.5, 4.7, 2.2 |
| H  | 4.7, 2.2, 3.5, 1.35 |
| I  | 1.05, 1.4, 1.5, 4.7, 2.2, 3.5, 1.35, 1.0 |
| K  | 1.35, 1.0, 11.5 |
| M  | 1.05, 1.4, 1.5, 4.7, 2.2 |
| O  | 1.5, 4.7, 2.2, 3.5, 1.35 |
| R  | 4.7, 2.2, 3.5, 1.35, 1.0 |
| T  | 1.5, 4.7, 2.2, 3.5, 1.35, 1.0 |
| V  | 3.5, 1.35, 1.0, 11.5 |
| X  | 1.35, 1.0, 11.5 |
| Y  | 1.5, 4.7, 2.2, 3.5, 1.35, 1.0 |
| A' | 1.5, 4.7, 2.2, 3.5 |
| C' | 1.35, 1.0, 11.5 |
| E' | 2.2, 3.5, 1.35, 1.0 |
| H' | 2.2, 3.5, 1.35, 1.0 |
| J' | 4.7, 2.2, 3.5, 1.35, 1.0 |
| L' | 1.4, 1.5, 4.7, 2.2, 3.5, 1.35, 1.0 |
| N' | 1.05, 1.4, 1.5, 4.7, 2.2 |
| O' | 2.2, 3.5, 1.35, 1.0 |
| Q' | 4.7, 2.2, 3.5 |
| R' | 1.5, 4.7, 2.2, 3.5, 1.35, 1.0 |
| S' | 1.05, 1.4, 1.5, 4.7, 2.2, 3.5 |
| T' | 1.35, 1.0, 11.5 |
| U' | 1.05, 1.4, 1.5, 4.7, 2.2, 3.5, 1.35, 1.0 |

FIG. 3.

BamHI RESTRICTION MAPS OF LAMBDA 1059 CLONES SELECTED BY HYBRIDIZATION WITH X708

| CLONE DESIGNATION | BamHI FRAGMENTS |
|---|---|
| 3 | 1.05, 1.4, 1.5, 4.7 |
| 4 | 1.4, 1.5, 4.7, 2.2, 3.5, 1.35, 1.0 |
| 5 | 1.9, 5.8, 1.05, 1.4, 1.5 |
| 7 | 1.9, 5.8, 1.05, 1.4 |
| 8 | 1.9, 5.8, 1.05, 1.4, 1.5 |
| 9 | 1.05, 1.4, 1.5, 4.7 |
| 10 | 1.05, 1.4, 1.5 |
| 11 | 1.4, 1.5, 4.7, 2.2, 3.5, 1.35, 1.0 |
| 12 | 1.5, 4.7, 2.2, 3.5 |
| 14 | 5.8, 1.05, 1.4, 1.5, 4.7 |
| 15 | 5.8, 1.05, 1.4, 1.5 |
| 16 | 5.8, 1.05, 1.4, 1.5, 4.7, 2.2 |
| 17 | 1.05, 1.4, 1.5, 4.7, 2.2 |
| 18 | 1.9, 5.8, 1.05, 1.4, 1.5 |
| 19 | 5.8, 1.05, 1.4, 1.5 |
| 20 | 5.8, 1.05, 1.4, 1.5, 4.7, 2.2 |
| 21 | 1.05, 1.4, 1.5 |
| 22 | 1.9, 5.8, 1.05, 1.4, 1.5 |
| 23 | 1.05, 1.4, 1.5, 4.7, 2.2, 3.5 |
| 24 | 1.05, 1.4, 1.5, 4.7, 2.2 |
| 25 | 1.05, 1.4, 1.5, 4.7 |
| 26 | 1.05, 1.4, 1.5, 4.7, 2.2, 3.5 |
| 28 | 1.5, 4.7, 2.2, 3.5, 1.35, 1.0 |
| 29 | 1.05, 1.4, 1.5, 4.7, 2.2, 3.5, 1.35, 1.0 |
| 33 | 1.9, 5.8, 1.05 |
| 35 | 1.05, 1.4, 1.5, 4.7, 2.2, 3.5, 1.35 |

BamHI RESTRICTION MAP OF THE REGION OF THE XANTHOMONAS GENOME CONTAINING THE GUM GENE CLUSTER

FIG. IOA-I

```
           10         20         30         40         50         60
    GGATCCGGTT GAGGCGGTAA CAGGGGATTG GCATGGCATT GACGAAAGCG GAGATGGCCG
    CCTAGGCCAA CTCCGCCATT GTCCCCTAAC CGTACCGTAA CTGCTTTCGC CTCTACCGGC 70         80         90        100        110        120
    AGCGTCTGTT CGACGAAGTC GGCCTGAACA AGCGTGAGGC GAAGGAATTC GTCGACGCGT
    TCGCAGACAA GCTGCTTCAG CCGGACTTGT TCGCACTCCG CTTCCTTAAG CAGCTGCGCA 130        140        150        160        170        180
    TTTTCGATGT GCTGCGCGAT GCACTGGAGC AGGGCCGTCA GGTGAAGTTG TCGGGCTTCG
    AAAAGCTACA CGACGCGCTA CGTGACCTCG TCCCGGCAGT CCACTTCAAC AGCCCGAAGC 190        200        210        220        230        240
    GCAACTTCGA TCTGCGGCGC AAGAACCAAC GGCCCGGTCG CAATCCCAAG ACCGGTGAGG
    CGTTGAAGCT AGACGCCGCG TTCTTGGTTG CCGGGCCAGC GTTAGGGTTC TGGCCACTCC 250        260        270        280        290        300
    AAATTCCGAT CTCGGCCAGG ACGGTGGTGA CCTTCCGCCC CGGCCAGAAA CTCCAAGGAA
    TTTAAGGCTA GAGCCGGTCC TGCCACCACT GGAAGGCGGG GCCGGTCTTT GAGGTTCCTT 310        320        330        340        350        360
    CTGGGTGGAG GCTTATGCTG GATCCGGGCA GTAATCGCGA GCTACCGCCG ATTCCGGCCA
    GACCCACCTC CGAATACGAC CTAGGCCCGT CATTAGCGCT CGATGGCGGC TAAGGCCGGT 370        380        390        400        410        420
    AGCGCTACTT CACCATCGGT GAGGTGAGCG AGCTGTGCGA CGTCAAGCCG CACGTGCTGC
    TCGCGATGAA GTGGTAGCCA CTCCACTCGC TCGACACGCT GCAGTTCGGC GTGCACGACG
```

FIG. 10A-2

```
            430        440        450        460        470        480
     GCTATTGGGA AACCGAATTT CCGAGCCTGG AGGCCAGTCA AGCGGCGCGC AACCGACGCT
     CGATAACCCT TTGGCTTAAA GGCTCGGACC TCCGGTCAGT TCGCCGCGCG TTGGCTGCGA 490        500        510        520        530        540
     ACTACCAGCG GCACGATGTC GTGATGGTGC GGCAGATTCG TGGCCTGCTG TACGAGCAGG
     TGATGGTCGC CGTGCTACAG CACTACCACG CCGTCTAAGC ACCGGACGAC ATGCTCGTCC 550        560        570        580        590        600
     GTTACACCAT CGGGGGCGCG CGTCTGCGTC TTGAAGGGGA TGGGGCCAAG AGCGAGTCAG
     CAATGTGGTA GCCCCCGCGC GCAGACGCAG AACTTCCCCT ACCCCGGTTC TCGCTCAGTC 610        620        630        640        650        660
     CGCTGAGCAA TCAGATCATC AAGCAGGTGC GCATGGAGCT TGAAGAAGTC CTGCAGCTGC
     GCGACTCGTT AGTCTAGTAG TTCGTCCACG CGTACCTCGA ACTTCTTCAG GACGTCGACG 670        680        690        700        710        720
     TGCGACGCTA GGAAAGCGCC GCATAAAGCC GCTATAATCG CAGGCCGCCT CAGGGCGGGA
     ACGCTGCGAT CCTTTCGCGG CGTATTTCGG CGATATTAGC GTCCGGCGGA GTCCCGCCCT 730        740        750        760        770        780
     CGCAACATCT TCGGGGTATA GCGCAGCCTG GTAGCGCACT AGTCTGGGGG ACTAGTGGTC
     GCGTTGTAGA AGCCCCATAT CGCGTCGGAC CATCGCGTGA TCAGACCCCC TGATCACCAG 790        800        810        820        830        840
     GTCGGTTCGA ATCCGGCTAC CCCGACCAAA CAACAGGCCT ACGTCGCAAG ACGTGGGCCT
     CAGCCAAGCT TAGGCCGATG GGGCTGGTTT GTTGTCCGGA TGCAGCGTTC TGCACCCGGA
```

FIG. 10A-3

```
          850        860        870        880        890        900
     TTTTGTTGCG TCGCAACATG TCAGTTCGAT GGCATTCCAG GCTATGCCAC TATGCGCAAC
     AAAACAACGC AGCGTTGTAC AGTCAAGCTA CCGTAAGGTC CGATACGGTG ATACGCGTTG 910        920        930        940        950        960
     GGCATATTGC AAGGCGGCAT ATGCAAGTCC TGTACGCAAT TATTTCGCGG TTCAGGCTGC
     CCGTATAACG TTCCGCCGTA TACGTTCAGG ACATGCGTTA ATAAAGCGCC AAGTCCGACG 970        980        990       1000       1010       1020
     TACAAGTCGG GATCAGCAGG CGTCCGTAAG TGCCCGGAAA CGCTAGAGTT CGTATGCTGA
     ATGTTCAGCC CTAGTCGTCC GCAGGCATTC ACGGGCCTTT GCGATCTCAA GCATACGACT 1030       1040       1050       1060       1070       1080
     GAATGACGAC CCAGGTCACG TTCTCTTAAC GTCGAGGCGA CGAACTTGAA TCAATAGGCC
     CTTACTGCTG GGTCCAGTGC AAGAGAATTG CAGCTCCGCT GCTTGAACTT AGTTATCCGG 1090       1100       1110       1120       1130       1140
     AACGCCGTCA AAAAAATGGC GTGTTGTGCC TTGCGATGTG TTCGTTCTAT GCCATAGTGC
     TTGCGGCAGT TTTTTTACCG CACAACACGG AACGCTACAC AAGCAAGATA CGGTATCACG 1150       1160       1170       1180       1190       1200
     ACTGCAACAC GCGATTCAAC GTTGGTCCCG GCACGCGTCG GGATGCAACT TCCTGTCGTA
     TGACGTTGTG CGCTAAGTTG CAACCAGGGC CGTGCGCAGC CCTACGTTGA AGGACAGCAT 1210       1220       1230       1240       1250       1260
     CGTTCGTGCT GGCGCCTGAG CCGGTTGAAT GCTGCGCGAG GTCCTGTCCC ACCCAACAGA
     GCAAGCACGA CCGCGGACTC GGCCAACTTA CGACGCGCTC CAGGACAGGG TGGGTTGTCT
```

FIG. 10A-4

```
         1270       1280       1290       1300       1310       1320
    GGCAGCCAGC TACACGCATG AAGAAACTGA TCGGACGACT CGTCGCAAGG CCTCAGCCTG
    CCGTCGGTCG ATGTGCGTAC TTCTTTGACT AGCCTGCTGA GCAGCGTTCC GGAGTCGGAC 1330       1340       1350       1360       1370       1380
    GCTCTGCTCT GCTCGATGTC GCTGGGCGCT TGCAGCACCG GCCCGGAGAT GGCGTCTTCG
    CGAGACGAGA CGAGCTACAG CGACCCGCGA ACGTCGTGGC CGGGCCTCTA CCGCAGAAGC 1390       1400       1410       1420       1430       1440
    CTGCCGCATC CGGACCCGCT GGCAATGTCC ACGGTGCAGC CCGAATACCG TCTTGCGCCG
    GACGGCGTAG GCCTGGGCGA CCGTTACAGG TGCCACGTCG GGCTTATGGC AGAACGCGGC 1450       1460       1470       1480       1490       1500
    GGCGATCTGT TGCTGGTGAA GGTGTTTCAG ATCGACGATC TGGAGCGGCA GGTCCGCATC
    CCGCTAGACA ACGACCACTT CCACAAAGTC TAGCTGCTAG ACCTCGCCGT CCAGGCGTAG 1510       1520       1530       1540       1550       1560
    GACCAGAACG GTCACATCTC ACTGCCGTTG ATTGGCGACG TCAAGGCCGC CGGTCTGGGC
    CTGGTCTTGC CAGTGTAGAG TGACGGCAAC TAACCGCTGC AGTTCCGGCG GCCAGACCCG 1570       1580       1590       1600       1610       1620
    GTTGGCGAAC TGGAAAAGCT GGTCGCCGAT CGGTATCGCG CAGGCTACCT GCAGCAGCCG
    CAACCGCTTG ACCTTTTCGA CCAGCGGCTA GCCATAGCGC GTCCGATGGA CGTCGTCGGC 1630       1640       1650       1660       1670       1680
    CAGATTTCGG TATTCGTGCA GGAGTCCAAC GGGCGTCGCG TCACGGTCAC TGGTGCGGTA
    GTCTAAAGCC ATAAGCACGT CCTCAGGTTG CCCGCAGCGC AGTGCCAGTG ACCACGCCAT
```

FIG. 10A-5

```
           1690       1700       1710       1720       1730       1740
      GACGAGCCGG GCATCTACCC GGTGATCGGC GCCAACCTCA CCTTGCAGCA GGCGATCGCG
      CTGCTCGGCC CGTAGATGGG CCACTAGCCG CGGTTGGAGT GGAACGTCGT CCGCTAGCGC 1750       1760       1770       1780       1790       1800
      CAGGCCAAGG GTGTCAGCAC GGTGGCAAGC CGCGGCAACG TGATCGTGTT CCGCATGGTC
      GTCCGGTTCC CACAGTCGTG CCACCGTTCG GCGCCGTTGC ACTAGCACAA GGCGTACCAG 1810       1820       1830       1840       1850       1860
      AACGGGCAAA AAATGATTGC GCGGTTCGAC CTGACCGAGA TCGAGAAGGG GGCCAATCCG
      TTGCCCGTTT TTTACTAACG CGCCAAGCTG GACTGGCTCT AGCTCTTCCC CCGGTTAGGC 1870       1880       1890       1900       1910       1920
      GATCCTGAGA TTTATGGCGG CGACATTGTC GTGGTGTATC GCTCGGATGC GCGCGTGTGG
      CTAGGACTCT AAATACCGCC GCTGTAACAG CACCACATAG CGAGCCTACG CGCGCACACC 1930       1940       1950       1960       1970       1980
      TTGCGCACCA TGCTGGAACT GACCCCCTTG GTGATGGTGT GGCGCGCTTA CCGATGAGTA
      AACGCGTGGT ACGACCTTGA CTGGGGGAAC CACTACCACA CCGCGCGAAT GGCTACTCAT 1990       2000       2010       2020       2030       2040
      TGAATTCAGA CAATCGTTCC TCTTCGTCGC AGCGGTCATG GTCATCTGGA ACTGGCAGAT
      ACTTAAGTCT GTTAGCAAGG AGAAGCAGCG TCGCCAGTAC CAGTAGACCT TGACCGTCTA 2050       2060       2070       2080       2090       2100
      GTCGACTTGA TGGACTACTG GCGCGCCCTG GTCTCGCAGC TCTGGCTGAT CATCCTGATC
      CAGCTGAACT ACCTGATGAC CGCGCGGGAC CAGAGCGTCG AGACCGACTA GTAGGACTAG
```

FIG. 10A-6

```
       2110        2120        2130        2140        2150        2160
  GCCGTCGGCG  CGCTGTTGCT  GGCATTCGGC  ATCACGATGT  TGATGCCCGA  GAAGTACCGC
  CGGCAGCCGC  GCGACAACGA  CCGTAAGCCG  TAGTGCTACA  ACTACGGGCT  CTTCATGGCG 2170        2180        2190        2200        2210        2220
  GCCACCAGCA  CCCTGCAGAT  CGAACGTGAC  TCGCTCAATG  TGGTGAACGT  CGACAACCTG
  CGGTGGTCGT  GGGACGTCTA  GCTTGCACTG  AGCGAGTTAC  ACCACTTGCA  GCTGTTGGAC 2230        2240        2250        2260        2270        2280
  ATGCCGGTGG  AATCGCCGCA  GGATCGCGAT  TTCTACCAGA  CCCAGTACCA  GTTGCTGCAG
  TACGGCCACC  TTAGCGGCGT  CCTAGCGCTA  AAGATGGTCT  GGGTCATGGT  CAACGACGTC 2290        2300        2310        2320        2330        2340
  AGCCGTTCGC  TGGCGCGTGC  GGTGATCCGG  GAAGCCAAGC  TCGATCAGGA  GCCGGCGTTC
  TCGGCAAGCG  ACCGCGCACG  CCACTAGGCC  CTTCGGTTCG  AGCTAGTCCT  CGGCCGCAAG 2350        2360        2370        2380        2390        2400
  AAGGAGCAGG  TGGAGGAGGC  GCTGGCCAAA  GCCGCCGAAA  AGAATCCCGA  GGCGGGTAAG
  TTCCTCGTCC  ACCTCCTCCG  CGACCGGTTT  CGGCGGCTTT  TCTTAGGGCT  CCGCCCATTC 2410        2420        2430        2440        2450        2460
  TCGCTCGATT  CGCGGCAGGC  GATCGTCGAG  CGCAGCCTCA  CCGATACGTT  GCTCGCCGGG
  AGCGAGCTAA  GCGCCGTCCG  CTAGCAGCTC  GCGTCGGAGT  GGCTATGCAA  CGAGCGGCCC 2470        2480        2490        2500        2510        2520
  CTGGTGGTCG  AGCCGATCCT  CAACTCGCGC  CTGGTGTACG  TCAATTACGA  TTCGCCAGAC
  GACCACCAGC  TCGGCTAGGA  GTTGAGCGCG  GACCACATGC  AGTTAATGCT  AAGCGGTCTG
```

FIG. 10A-7

```
          2530       2540       2550       2560       2570       2580
     CCGGTGCTGG CCGCCAAGAT CGCCAATACG TACCCGAAGG TGTTCATCGT CAGCACCCAG
     GGCCACGACC GGCGGTTCTA GCGGTTATGC ATGGGCTTCC ACAAGTAGCA GTCGTGGGTC 2590       2600       2610       2620       2630       2640
     GAACGCCGCA TGAAGGCGTC TTCGTTTGCG ACACAGTTTC TGGCTGAGCG CCTGAAGCAG
     CTTGCGGCGT ACTTCCGCAG AAGCAAACGC TGTGTCAAAG ACCGACTCGC GGACTTCGTC 2650       2660       2670       2680       2690       2700
     TTGCGCGAGA AGGTCGAAGA CTCTGAAAAG GATCTGGTCT CGTATTCGAC CGAAGAGCAG
     AACGCGCTCT TCCAGCTTCT GAGACTTTTC CTAGACCAGA GCATAAGCTG GCTTCTCGTC 2710       2720       2730       2740       2750       2760
     ATCGTGTCGG TTGGCGATGA CAAGCCCTCG CTGCCTGCGC AGAATCTGAC CGATCTCAAT
     TAGCACAGCC AACCGCTACT GTTCGGGAGC GACGGACGCG TCTTAGACTG GCTAGAGTTA 2770       2780       2790       2800       2810       2820
     GCGTTGCTGG CATCCGCACA GGACGCCCGG ATCAAGGCCG AGTCAGCTTG GCGGCAGGCT
     CGCAACGACC GTAGGCGTGT CCTGCGGGCC TAGTTCCGGC TCAGTCGAAC CGCCGTCCGA 2830       2840       2850       2860       2870       2880
     TCCAGTGGCG ATGGCATGTC ATTGCCGCAG GTGTTGAGCA GCCCGCTGAT TCAAAGCCTG
     AGGTCACCGC TACCGTACAG TAACGGCGTC CACAACTCGT CGGGCGACTA AGTTTCGGAC 2890       2900       2910       2920       2930       2940
     CGCAGCGAGC AGGTGCGTCT GACCAGCGAG TACCAGCAGA AACTGTCGAC CTTCAAGCCG
     GCGTCGCTCG TCCACGCAGA CTGGTCGCTC ATGGTCGTCT TTGACAGCTG GAAGTTCGGC
```

FIG. 10A-8

```
              2950       2960       2970       2980       2990       3000
         GATTACCCGG AGATGCAGCG CCTCAAGGCG CAGATCGAAG AGTCGCGTCG TCAGATCAAT
         CTAATGGGCC TCTACGTCGC GGAGTTCCGC GTCTAGCTTC TCAGCGCAGC AGTCTAGTTA 3010       3020       3030       3040       3050       3060
         GGCGAAGTCA TCAATATCCG TCAGTCGCTG AAGGCGACCT ACGACGCCTC CGTGCATCAG
         CCGCTTCAGT AGTTATAGGC AGTCAGCGAC TTCCGCTGGA TGCTGCGGAG GCACGTAGTC 3070       3080       3090       3100       3110       3120
         GAGCAGCTGC TCAACGACCG CATCGCCGGT CTGCGGTCCA ACGAGCTGGA TCTGCAGAGC
         CTCGTCGACG AGTTGCTGGC GTAGCGGCCA GACGCCAGGT TGCTCGACCT AGACGTCTCG 3130       3140       3150       3160       3170       3180
         CGCAGCATCC GCTACAACAT GCTCAAGCGC GAACGTCGAC ACCAACCGCC AGCTCTACGA
         GCGTCGTAGG CGATGTTGTA CGAGTTCGCG CTTGCAGCTG TGGTTGGCGG TCGAGATGCT 3190       3200       3210       3220       3230       3240
         TAGCGCTCCT GCAGCGCTAC AAGGAAATCG GCGTGGCGAG CAACGTGGGC GCCAACAACG
         ATCGCGAGGA CGTCGCGATG TTCCTTTAGC CGCACCGCTC GTTGCACCCG CGGTTGTTGC 3250       3260       3270       3280       3290       3300
         TGACCATCGT CGATACCGCA GACGTGCCTA CGTCTAAGAC TTCGCCGAAA CTCAAATTGA
         ACTGGTAGCA GCTATGGCGT CTGCACGGAT GCAGATTCTG AAGCGGCTTT GAGTTTAACT 3310       3320       3330       3340       3350       3360
         ACCTCGCGTT GGGCCTGATC TTTGGCGTAT TCCTGGGCGT GGCTGTGGCT CTGGTTCGCT
         TGGAGCGCAA CCCGGACTAG AAACCGCATA AGGACCCGCA CCGACACCGA GACCAAGCGA
```

FIG. 10A-9

```
       3370       3380       3390       3400       3410       3420
  ACTTCCTGCG TGGGCCTTCT CCGAAGTCGC GGTTGAACTG ACATCGTGAT GTTGCAAAAC
  TGAAGGACGC ACCCGGAAGA GGCTTCAGCG CCAACTTGAC TGTAGCACTA CAACGTTTTG 3430       3440       3450       3460       3470       3480
  GATGGTTAAT TGAAGTGACA ACTGATTCAG CGTGGAAAAG GTGGGATCCC GTAAGGTGCG
  CTACCAATTA ACTTCACTGT TGACTAAGTC GCACCTTTTC CACCCTAGGG CATTCCACGC 3490       3500       3510       3520       3530       3540
  GGCTCCCTCG TTTGAAGGTT TGTCTCTGTT GAAACAAAGG GCTGTCGTGC GATCTGGGGT
  CCGAGGGAGC AAACTTCCAA ACAGAGACAA CTTTGTTTCC CGACAGCACG CTAGACCCCA 3550       3560       3570       3580       3590       3600
  CGGTAGGTAT TACCGCGGTG ATCGGACGAC AGGATGATTG AAAGCTCGCG TGCGATTCGT
  BCCATCCATA ATGGCGCCAC TAGCCTGCTG TCCTACTAAC TTTCGAGCGC ACGCTAAGCA 3610       3620       3630       3640       3650       3660
  ATGTTCCCCC GCATGCGCCG TATCGAGTTT GGAGGACATC CCCATGCTTT TGGCAGACTT
  TACAAGGGGG CGTACGCGGC ATAGCTCAAA CCTCCTGTAG GGGTACGAAA ACCGTCTGAA 3670       3680       3690       3700       3710       3720
  GAGTAGCGCG ACTTACACGA CATCCTCGCC GCGATTGTTG TCCAAATATT CGGCAGCCGC
  CTCATCGCGC TGAATGTGCT GTAGGAGCGG CGCTAACAAC AGGTTTATAA GCCGTCGGCG 3730       3740       3750       3760       3770       3780
  CGACCTGGTC CTGCGCGTGT TCGACCTGAC CATGGTCGTT GCGTCCGGAC TGATCGCATA
  GCTGGACCAG GACGCGCACA AGCTGGACTG GTACCAGCAA CGCAGGCCTG ACTAGCGTAT
```

FIG. 10A-10

```
          3790       3800       3810       3820       3830       3840
     CCGCATCGTT TTCGGTACCT GGGTACCCGC AGCGCCTTAT CGGGTCGCGA TTGCGACAAC
     GGCGTAGCAA AAGCCATGGA CCCATGGGCG TCGCGGAATA GCCCAGCGCT AACGCTGTTG 3850       3860       3870       3880       3890       3900
     GTTGTTGTAC TCGGTGATCT GCTTTGCGTT GTTCCCGCTG TATCGCAGCT GGCGCGGCCG
     CAACAACATG AGCCACTAGA CGAAACGCAA CAAGGGCGAC ATAGCGTCGA CCGCGCCGGC 3910       3920       3930       3940       3950       3960
     TGGATTGCTG AGTGAGCTGG TGGTGCTGGG TGGCGCATTC GGCGGTGTGT TTGCGCTGTT
     ACCTAACGAC TCACTCGACC ACCACGACCC ACCGCGTAAG CCGCCACACA AACGCGACAA 3970       3980       3990       4000       4010       4020
     CGCGGTGCAT GCCCTGATCG TGCAGGTGGG TGAGCAGGTG TCGCGTGGTT GGGTCGGCCT
     GCGCCACGTA CGGGACTAGC ACGTCCACCC ACTCGTCCAC AGCGCACCAA CCCAGCCGGA 4030       4040       4050       4060       4070       4080
     GTGGTTCGTC GGCGGCCTGG TGTCGCTGGT GGCCGCACGC ACCTTGCTGC GTGGCTTCCT
     CACCAAGCAG CCGCCGGACC ACAGCGACCA CCGGCGTGCG TGGAACGACG CACCGAAGGA 4090       4100       4110       4120       4130       4140
     CAATCACCTG CGCACGCAGG GCGTGGATGT CCAGCGTGTG GTGGTAGTGG GCCTGCGTCA
     GTTAGTGGAC GCGTGCGTCC CGCACCTACA GGTCGCACAC CACCATCACC CGGACGCAGT 4150       4160       4170       4180       4190       4200
     TCCGGTGATG AAGATCAGTC ATTACCTGAG CCGTAATCCC TGGGTCGGCA TGAACATGGT
     AGGCCACTAC TTCTAGTCAG TAATGGACTC GGCATTAGGG ACCCAGCCGT ACTTGTACCA
```

FIG. 10A-11

```
           4210       4220       4230       4240       4250       4260
       TGGCTATTTC CGCACGCCGT ACGATCTGGC GGTGGCCGAA CAGCGCCAGG GTCTGCCGTG
       ACCGATAAAG GCGTGCGGCA TGCTAGACCG CCACCGGCTT GTCGCGGTCC CAGACGGCAC 4270       4280       4290       4300       4310       4320
       CCTGGGTGAT CCCGATGAGC TGATCGAGTA CCTGAAGAAC AACCAGGTGG AGCAGGTGTG
       GGACCCACTA GGGCTACTCG ACTAGCTCAT GGACTTCTTG TTGGTCCACC TCGTCCACAC 4330       4340       4350       4360       4370       4380
       GATCTCGCTG CCGCTTGGCG AGCGCGACCA CATCAAGCAG CTGCTGCAGC GCCTGGATCG
       CTAGAGCGAC GGCGAACCGC TCGCGCTGGT GTAGTTCGTC GACGACGTCG CGGACCTAGC 4390       4400       4410       4420       4430       4440
       CTACCCGATC AACGTGAAGC TGGTGCCCGA CCTGTTCGAC TTCGGCCTGT TGAACCAGTC
       GATGGGCTAG TTGCACTTCG ACCACGGGCT GGACAAGCTG AAGCCGGACA ACTTGGTCAG 4450       4460       4470       4480       4490       4500
       TGCCGAGCAG ATCGGCAGCG TGCCGGTGAT CAACCTGCGT CAGGGTGGCG TGGATCGTGA
       ACGGCTCGTC TAGCCGTCGC ACGGCCACTA GTTGGACGCA GTCCCACCGC ACCTAGCACT 4510       4520       4530       4540       4550       4560
       CAACTACTTC GTGGTCGCCA AGGCGCTGCA GGACAAGATC CTGGCGGTGA TTGCGCTGAT
       GTTGATGAAG CACCAGCGGT TCCGCGACGT CCTGTTCTAG GACCGCCACT AACGCGACTA 4570       4580       4590       4600       4610       4620
       GGGCCTGTGG CCGCTGATGC TGGCCATTGC GGTAGGCGTG AAGATGAGCT CGCCCGGCCC
       CCCGGACACC GGCGACTACG ACCGGTAACG CCATCCGCAC TTCTACTCGA GCGGGCCGGG
```

FIG. 10A-12

```
            4630       4640       4650       4660       4670       4680
       GGTGTTCTTC CGTCAGCGCC GCCACGGCCT GGGTGGCCGC GAGTTCTACA TGTTCAAGTT
       CCACAAGAAG GCAGTCGCGG CGGTGCCGGA CCCACCGGCG CTCAAGATGT ACAAGTTCAA 4690       4700       4710       4720       4730       4740
       CCGCTCGATG CGGGTGCATG ACGATCATGG CACCACGATT CAGCAGGCGA CCAAGAACGA
       GGCGAGCTAC GCCCACGTAC TGCTAGTACC GTGGTGCTAA GTCGTCCGCT GGTTCTTGCT 4750       4760       4770       4780       4790       4800
       CACGCGGATT ACGCGCTTCG GCAGTTTCCT GCGCCGCAGC AGCCTGGACG AGCTGCCGCA
       GTGCGCCTAA TGCGCGAAGC CGTCAAAGGA CGCGGCGTCG TCGGACCTGC TCGACGGCGT 4810       4820       4830       4840       4850       4860
       GATCTTCAAT GTCTTGGGTG GCAGCATGTC GATCGTGGGC CGCGCCCGC ACGCCGCGCA
       CTAGAAGTTA CAGAACCCAC CGTCGTACAG CTAGCACCCG GCGCGGGCG TGCGGCGCGT 4870       4880       4890       4900       4910       4920
       GCACAACACG CACTATGAAA AGCTGATCAA CCATTACATG CAGCGTCACT ACGTCAAGCC
       CGTGTTGTGC GTGATACTTT TCGACTAGTT GGTAATGTAC GTCGCAGTGA TGCAGTTCGG 4930       4940       4950       4960       4970       4980
       GGGGATTACC GGTTGGGCGC AGGTCAACGG TTTCCGCGGT GAGACCCCGG AGCTGCGGAC
       CCCCTAATGG CCAACCCGCG TCCAGTTGCC AAAGGCGCCA CTCTGGGGCC TCGACGCCTG 4990       5000       5010       5020       5030       5040
       GATGAAGAAG CGCATCCAGT ACGACCTTGA CTACATCCGT CGTTGGTCGC TGTGGCTGGA
       CTACTTCTTC GCGTAGGTCA TGCTGGAACT GATGTAGGCA GCAACCAGCG ACACCGACCT
```

FIG. 10A-13

```
            5050       5060       5070       5080       5090       5100
       TATCCGCATC ATCGTGCTGA CGGCCGTGCG CGTGCTCGGA CAGAAGACCG CGTACTGATG
       ATAGGCGTAG TAGCACGACT GCCGGCACGC GCACGAGCCT GTCTTCTGGC GCATGACTAC 5110       5120       5130       5140       5150       5160
       ACGGTGGGGA GTGTGCGACC TGGCGCACCT TGCGCCGCGG GCGGCTGCAT CGCAGCCGCC
       TGCCACCCCT CACACGCTGG ACCGCGTGGA ACGCGGCGCC CGCCGACGTA GCGTCGGCGG 5170       5180       5190       5200       5210       5220
       TTTCTCTCGC GGGCGCTGAC ATGCTGATTC AAATGAGCGA GCAGGCGCGG GTGCGTTGGC
       AAAGAGAGCG CCCGCGACTG TACGACTAAG TTTACTCGCT CGTCCGCGCC CACGCAACCG 5230       5240       5250       5260       5270       5280
       ACAACGCGCT GATCGAGCTG ACCCTGCTGA CCGGCGTGGG CTACAACCTG CTGCTGGCGT
       TGTTGCGCGA CTAGCTCGAC TGGGACGACT GGCCGCACCC GATGTTGGAC GACGACCGCA 5290       5300       5310       5320       5330       5340
       TGATCAACGC CAACGTGTTC ACCGTACGTC CGGTGATCAC ATATGCAGTG GAATTTCTGG
       ACTAGTTGCG GTTGCACAAG TGGCATGCAG GCCACTAGTG TATACGTCAC CTTAAAGACC 5350       5360       5370       5380       5390       5400
       TCTACGCAGC CTGTTTCCTG CTCGGGCTGG GCTCGATGAG CCGACAGCGC ATCGCGATGA
       AGATGCGTCG GACAAAGGAC GAGCCCGACC CGAGCTACTC GGCTGTCGCG TAGCGCTACT 5410       5420       5430       5440       5450       5460
       TCTTCGGCGG GCTAGGCTTG ATCGTGACGC TGATGTTCGT GCGTTTCCTG GTCAACTGGC
       AGAAGCCGCC CGATCCGAAC TAGCACTGCG ACTACAAGCA CGCAAAGGAC CAGTTGACCG
```

FIG. 10A-14

```
           5470        5480        5490        5500        5510        5520
      AGATCGACCC  CAAGTTCTTC  CGCGATGCCC  TGGTGGTCTT  TGCATTTGTC  GTGCTGGGGT
      TCTAGCTGGG  GTTCAAGAAG  GCGCTACGGG  ACCACCAGAA  ACGTAAACAG  CACGACCCCA 5530        5540        5550        5560        5570        5580
      CTGCTTACAC  CGGCTCGTTG  CCCAAGCTGT  TCATACGCAT  GACGATCATC  GTGTCATTGG
      GACGAATGTG  GCCGAGCAAC  GGGTTCGACA  AGTATGCGTA  CTGCTAGTAG  CACAGTAACC 5590        5600        5610        5620        5630        5640
      TCGCTGCGTT  CGAGCTGGCG  ATGCCCTCGG  CTTATGGCGA  TCTGGTCAAC  CCGAAGAGCT
      AGCGACGCAA  GCTCGACCGC  TACGGGAGCC  GAATACCGCT  AGACCAGTTG  GGCTTCTCGA 5650        5660        5670        5680        5690        5700
      TCTTCGTCAA  TGCGCGCGGC  ATGAGTGCAG  AAGGGTTCTG  GAACGAGGAC  AGCAATCTGT
      AGAAGCAGTT  ACGCGCGCCG  TACTCACGTC  TTCCCAAGAC  CTTGCTCCTG  TCGTTAGACA 5710        5720        5730        5740        5750        5760
      TCGTCAGTGC  CACACGACCC  GGTGAGCGCA  ACTTCCTCCC  AGGCTCGAAC  CTGCCACGCG
      AGCAGTCACG  GTGTGCTGGG  CCACTCGCGT  TGAAGGAGGG  TCCGAGCTTG  GACGGTGCGC 5770        5780        5790        5800        5810        5820
      CCTCTTCCTG  GTTCATCGAG  CCGGTGACGA  TGGGCAATTA  CATCTGCTTC  TTCACCGCGA
      GGAGAAGGAC  CAAGTAGCTC  GGCCACTGCT  ACCCGTTAAT  GTAGACGAAG  AAGTGGCGCT 5830        5840        5850        5860        5870        5880
      TCGTATTGAC  GTTCTGGCGC  TGGATGCGGC  CGTCGATGCT  GATTCTGTCT  ATTGGATTGA
      AGCATAACTG  CAAGACCGCG  ACCTACGCCG  GCAGCTACGA  CTAAGACAGA  TAACCTAACT
```

FIG. 10A-15

```
         5890       5900       5910       5920       5930       5940
    TCGGCTTCAT GATTGTGGCA TCCGACGGCC GACTGGCTGC CGGCACCTGT GTGCTGATGG
    AGCCGAAGTA CTAACACCGT AGGCTGCCGG CTGACCGACG GCCGTGGACA CACGACTACC 5950       5960       5970       5980       5990       6000
    TGCTGCTGTC GCCGTTATTG AAACGGATGG ATCAGCGGTT GGCGTTCCTG TTGTTCCTGT
    ACGACGACAG CGGCAATAAC TTTGCCTACC TAGTCGCCAA CCGCAAGGAC AACAAGGACA 6010       6020       6030       6040       6050       6060
    TTGTGATCGC CTCTGCCTGG CTGCTGGTGT GGATGACCGG GATTACGGCC TACCAGGACA
    AACACTAGCG GAGACGGACC GACGACCACA CCTACTGGCC CTAATGCCGG ATGGTCCTGT 6070       6080       6090       6100       6110       6120
    CCACGATGGG GCGCATCTTC TTCACTGTGA ATTCGATGAA CAATCTATCG TTCGAGTCGT
    GGTGCTACCC CGCGTAGAAG AAGTGACACT TAAGCTACTT GTTAGATAGC AAGCTCAGCA 6130       6140       6150       6160       6170       6180
    GGATGGGCCT GGATTTTGCG CAGGCCTACC GGTATTTCGA CAGCGGTATT TCTTACTTTA
    CCTACCCGGA CCTAAAACGC GTCCGGATGG CCATAAAGCT GTCGCCATAA AGAATGAAAT 6190       6200       6210       6220       6230       6240
    TTGCTTCGCA GTCGATTGTC GGCGTGCTGG CGTTCCTGCT GTCTTATTCG TTCCTGCTGC
    AACGAAGCGT CAGCTAACAG CCGCACGACC GCAAGGACGA CAGAATAAGC AAGGACGACG 6250       6260       6270       6280       6290       6300
    TGATGCCGAG CAAGGAAGGG CAGTTGTTCA AAAACCAGGC GATGTTTGCC TTTGCACTGA
    ACTACGGCTC GTTCCTTCCC GTCAACAAGT TTTTGGTCCG CTACAAACGG AAACGTGACT
```

FIG. 10A-16

```
       6310       6320       6330       6340       6350       6360
GCCTGTTGGT GTCTAACGGC TATTTCTCGA TCAAGACATC GGCGCTGTGG TGGTTTGTCT
CGGACAACCA CAGATTGCCG ATAAAGAGCT AGTTCTGTAG CCGCGACACC ACCAAACAGA 6370       6380       6390       6400       6410       6420
GCGGCTGCAT GTGGCACCTG ATGCCAGCAG CGTCAGCCGT GCCGGTGCGC GACGAAAGCA
CGCCGACGTA CACCGTGGAC TACGGTCGTC GCAGTCGGCA CGGCCACGCG CTGCTTTCGT 6430       6440       6450       6460       6470       6480
AGGAAGATCC AACGGACAAC GGCGTGCATG TGCCGTTGCC CGCAGGAGCG CCGCGGTGAA
TCCTTCTAGG TTGCCTGTTG CCGCACGTAC ACGGCAACGG GCGTCCTCGC GGCGCCACTT 6490       6500       6510       6520       6530       6540
TACGGTGACA GGGGCATCGG GGACGTCGGC GCCTGTGCAG GCTGCCGGCG CGCGTGCCTT
ATGCCACTGT CCCCGTAGCC CCTGCAGCCG CGGACACGTC CGACGGCCGC GCGCACGGAA 6550       6560       6570       6580       6590       6600
CGCGAGCGGC CGTAGCCGCG ATCCACGTAT CGATGCGACC AAGGCGATCG CGATATTGCT
GCGCTCGCCG GCATCGGCGC TAGGTGCATA GCTACGCTGG TTCCGCTAGC GCTATAACGA 6610       6620       6630       6640       6650       6660
GGTGGTGTTC TGCCACGCAA AAGGCGTGCC GCACGGAATG ACCCTGTTTG CCTACAGCTT
CCACCACAAG ACGGTGCGTT TTCCGCACGG CGTGCCTTAC TGGGACAAAC GGATGTCGAA 6670       6680       6690       6700       6710       6720
TCACGTTCCG CTTTTCTTCC TCGTGTCGGG TTGGCTGGCT GCCGGTTATG CCTCGCGCAC
AGTGCAAGGC GAAAAGAAGG AGCACAGCCC AACCGACCGA CGGCCAATAC GGAGCGCGTG
```

FIG. 10A-17

```
           6730       6740       6750       6760       6770       6780
       AACCAGCCTG CTGCAGACAA TCACCAAGCA GGCACGTGGT CTGTTGCTGC CCTATGTCGT
       TTGGTCGGAC GACGTCTGTT AGTGGTTCGT CCGTGCACCA GACAACGACG GGATACAGCA 6790       6800       6810       6820       6830       6840
       GTTCTATCTG CTTGGATATG TGTATTGGCT GTTGACGCGC AACATCGGCG AGAAAGCTGC
       CAAGATAGAC GAACCTATAC ACATAACCGA CAACTGCGCG TTGTAGCCGC TCTTTCGACG 6850       6860       6870       6880       6890       6900
       ACGTTGGGGG AGCCACCCGT GGTGGGAGCC GATCGTGTCG ATGTTTACCG GCGTCGGCCC
       TGCAACCCCC TCGGTGGGCA CCACCCTCGG CTAGCACAGC TACAAATGGC CGCAGCCGGG 6910       6920       6930       6940       6950       6960
       GGATCTGTAT GTGCAGCCGC CGCTGTGGTT CCTGCCGGTG ATGCTGGTCA CCGTGATTGG
       CCTAGACATA CACGTCGGCG GCGACACCAA GGACGGCCAC TACGACCAGT GGCACTAACC 6970       6980       6990       7000       7010       7020
       CTACGTTCTG TTGCGGCGCT GGATGCCGCC ACTGGTCATT GCGGCTGTCG CAGTTGTTCT
       GATGCAAGAC AACGCCGCGA CCTACGGCGG TGACCAGTAA CGCCGACAGC GTCAACAAGA 7030       7040       7050       7060       7070       7080
       CGCCTGGTTC TGGATGAACT GGTTTCCGCT CCAGCACATG CGATTGTTCT GGGGCCTGGA
       GCGGACCAAG ACCTACTTGA CCAAAGGCGA GGTCGTGTAC GCTAACAAGA CCCCGGACCT 7090       7100       7110       7120       7130       7140
       TGTGCTACCG GTGTCGCTGT GCTTCTACGC ACTGGGCGCG CTGCTGATCC ACGTGTCGCC
       ACACGATGGC CACAGCGACA CGAAGATGCG TGACCCGCGC GACGACTAGG TGCACAGCGG
```

FIG. 10A-18

```
         7150       7160       7170       7180       7190       7200
    GTATCTTCCA ACCTCCTTGC CTGGTAGCGC GTTGGTCACC GTAGTGCTGG CAGCATTGGT
    CATAGAAGGT TGGAGGAACG GACCATCGCG CAACCAGTGG CATCACGACC GTCGTAACCA 7210       7220       7230       7240       7250       7260
    TGCCTGGCTG GCCGGGGTCA ACGGCCGCAT CGATGTCAAC ATGCTGGAAT TCGGAAGGCA
    ACGGACCGAC CGGCCCCAGT TGCCGGCGTA GCTACAGTTG TACGACCTTA AGCCTTCCGT 7270       7280       7290       7300       7310       7320
    GCATGCCGTA TTCCTGTTGA GTGCAGTGGC GGGTTCGTTG ATGGTGATCT GCGCGGCGCG
    CGTACGGCAT AAGGACAACT CACGTCACCG CCCAAGCAAC TACCACTAGA CGCGCCGCGC 7330       7340       7350       7360       7370       7380
    CATGGTGCAG GAATGGACAT GGCTGCAGTG GATCGGGCGC AACACCTTGC TGATCCTGTG
    GTACCACGTC CTTACCTGTA CCGACGTCAC CTAGCCCGCG TTGTGGAACG ACTAGGACAC 7390       7400       7410       7420       7430       7440
    CACGCACATG CTGGTCTTCT TTGTACTGTC TGGTGTTGCG GCCTTGGCGG GTGGGTTTGG
    GTGCGTGTAC GACCAGAAGA AACATGACAG ACCACAACGC CGGAACCGCC CACCCAAACC 7450       7460       7470       7480       7490       7500
    TGGGGCGCGC CCAGGCCTTG GTTGGGCCAT CTTCGTGACG CTCTTTGCGC TGGTCGCCAG
    ACCCCGCGCG GGTCCGGAAC CAACCCGGTA GAAGCACTGC GAGAAACGCG ACCAGCGGTC 7510       7520       7530       7540       7550       7560
    CGTTCCGCTG CGCTGGTTTC TGATGCGTTT TGCCCCCTGG ACCTTGGGTG CACGTCCGGT
    GCAAGGCGAC GCGACCAAAG ACTACGCAAA ACGGGGGACC TGGAACCCAC GTGCAGGCCA
```

FIG. 10A-19

```
            7570       7580       7590       7600       7610       7620
      GTCGGCATGA CGACGGCTGC GATCACTGCC GGTCGCGTCG ACACAATCGC CTCAACTGTC
      CAGCCGTACT GCTGCCGACG CTAGTGACGG CCAGCGCAGC TGTGTTAGCG GAGTTGACAG 7630       7640       7650       7660       7670       7680
      GCGGAGCGCG ACTGGCAGAT CGACGTGGCC AAGGCTCTTG CGATCATTCT GGTCGCGCTG
      CGCCTCGCGC TGACCGTCTA GCTGCACCGG TTCCGAGAAC GCTAGTAAGA CCAGCGCGAC 7690       7700       7710       7720       7730       7740
      GGGCACGCCA GTGGCATGCC GCCTGCCTAC AAGCTGTTTG CCTACAGCTT CCATGTGCCT
      CCCGTGCGGT CACCGTACGG CGGACGGATG TTCGACAAAC GGATGTCGAA GGTACACGGA 7750       7760       7770       7780       7790       7800
      CTGTTTTTCG TTCTTTCCGG CTGGGTCGGT GAACGCTTCG GGCGTCGTGC ATTTGGCCGG
      GACAAAAAGC AAGAAAGGCC GACCCAGCCA CTTGCGAAGC CCGCAGCACG TAAACCGGCC 7810       7820       7830       7840       7850       7860
      AAGACGGTGG GAAAGCTTGC GCGCACGCTG CTGATTCCCT ACGTCAGCTT TTTTCTGGTG
      TTCTGCCACC CTTTCGAACG CGCGTGCGAC GACTAAGGGA TGCAGTCGAA AAAAGACCAC 7870       7880       7890       7900       7910       7920
      GCTTACGGCT ACTGGATACT GAGCGCAGTG CTCAACGGCA CATCCCAGTC CTGGGCTGGC
      CGAATGCCGA TGACCTATGA CTCGCGTCAC GAGTTGCCGT GTAGGGTCAG GACCCGACCG 7930       7940       7950       7960       7970       7980
      CACCCCTGGT GGCATCCGTT TGTTGGATTG CTGTGGGCCA ATGGATCCAG CTTGTATGTG
      GTGGGGACCA CCGTAGGCAA ACAACCTAAC GACACCCGGT TACCTAGGTC GAACATACAC
```

FIG. 10A-20

```
       7990       8000       8010       8020       8030       8040
  CTCCCGGCCT TGTGGTTTCT CCCCGCACTG TTTGTCGCCA CCGTTGTCTA CCTGGCACTG
  GAGGGCCGGA ACACCAAAGA GGGGCGTGAC AAACAGCGGT GGCAACAGAT GGACCGTGAC 8050       8060       8070       8080       8090       8100
  CGCGAAGACC TGAGCGCCGC AGTGCTCGCG GTCTGCAGTT TGCTGGTTGT GTGGGCGTGG
  GCGCTTCTGG ACTCGCGGCG TCACGAGCGC CAGACGTCAA ACGACCAACA CACCCGCACC 8110       8120       8130       8140       8150       8160
  ACGCGTTGGT TCCCAGGGCT GCGGCTGCGC CTTCCGTTTG CACTGGATGT GCTGCCGGTC
  TGCGCAACCA AGGGTCCCGA CGCCGACGCG GAAGGCAAAC GTGACCTACA CGACGGCCAG 8170       8180       8190       8200       8210       8220
  GCGCTGTTCT TCATTGCAGT CGGCGCATGG CTGTCACGCT TCGCAGAGAG AGTGCGCGCG
  CGCGACAAGA AGTAACGTCA GCCGCGTACC GACAGTGCGA AGCGTCTCTC TCACGCGCGC 8230       8240       8250       8260       8270       8280
  CTTCCTGCGG TCGTTTGGGT CGTCGCGTTC CCGGTCCTGG CATTCGCCTG GGGGGGCGTT
  GAAGGACGCC AGCAAACCCA GCAGCGCAAG GGCCAGGACC GTAAGCGGAC CCCCCCGCAA 8290       8300       8310       8320       8330       8340
  GCAGCCATGA ACGGGCAGGT GGATGTCAAT AATCTTCAGT TCGGAAAATC GTCGCTCCTG
  CGTCGGTACT TGCCCGTCCA CCTACAGTTA TTAGAAGTCA AGCCTTTTAG CAGCGAGGAC 8350       8360       8370       8380       8390       8400
  TTCCTGATCG CAAGCCTGCT GGGTACAGCA ATGACGTTGT GCATTGCCTA CTTCATGCAA
  AAGGACTAGC GTTCGGACGA CCCATGTCGT TACTGCAACA CGTAACGGAT GAAGTACGTT
```

FIG. 10A-21

```
         8410       8420       8430       8440       8450       8460
    GGGTGGCGCT GGCTGCGTTG GATCGGCGCC AATACGCTGC TGATCCTTGG CACGCACACG
    CCCACCGCGA CCGACGCAAC CTAGCCGCGG TTATGCGACG ACTAGGAACC GTGCGTGTGC 8470       8480       8490       8500       8510       8520
    TTGGTGTTTC TGGTCGTGAC CAGTGTCGTG GTGCGAACCG GGGTGATCGA TCGCAAACTC
    AACCACAAAG ACCAGCACTG GTCACAGCAC CACGCTTGGC CCCACTAGCT AGCGTTTGAG 8530       8540       8550       8560       8570       8580
    ATCGGTACAC CTGTCTGGGC GCTGGCTCTC TGCGCCTTTG CCATCGCTGC CTGCATTCCC
    TAGCCATGTG GACAGACCCG CGACCGAGAG ACGCGGAAAC GGTAGCGACG GACGTAAGGG 8590       8600       8610       8620       8630       8640
    ATGCGTGCCG TGCTGGTGCG CCGCGCCCTG GATGTTGGGA TTGAAACGCA AGTGAGACAT
    TACGCACGGC ACGACCACGC GGCGCGGGAC CTACAACCCT AACTTTGCGT TCACTCTGTA 8650       8660       8670       8680       8690       8700
    TTTCAGAATC ATCAGTCGAT GTGGCGTGTT CGTGTGAGTC ACCGGCAAAG GAGATCGGCG
    AAAGTCTTAG TAGTCAGCTA CACCGCACAA GCACACTCAG TGGCCGTTTC CTCTAGCCGC 8710       8720       8730       8740       8750       8760
    CAATGAAAGT CGTGCATGTG GTCCGCCAGT TCCATCCGTC GATCGGGGGG ATGGAGGAAG
    GTTACTTTCA GCACGTACAC CAGGCGGTCA AGGTAGGCAG CTAGCCCCCC TACCTCCTTC 8770       8780       8790       8800       8810       8820
    TCGTGCTGAA CGTGGCACGT CAGCATCAGG CCAACAGTGC CGACACGGTT GAGATCGTGA
    AGCACGACTT GCACCGTGCA GTCGTAGTCC GGTTGTCACG GCTGTGCCAA CTCTAGCACT
```

FIG. 10A-22

```
          8830        8840        8850        8860        8870        8880
      CGTTGGATCG  TGTGTTCACC  GATCCCTCTG  CGCAACTGGC  GCAGCACGAG  GTCCATCAGG
      GCAACCTAGC  ACACAAGTGG  CTAGGGAGAC  GCGTTGACCG  CGTCGTGCTC  CAGGTAGTCC 8890        8900        8910        8920        8930        8940
      GGTTGTCGAT  CACTCGCATC  GGCTATCGTG  GTTCATCGCG  GTACCCGATC  GCGCCGTCGG
      CCAACAGCTA  GTGAGCGTAG  CCGATAGCAC  CAAGTAGCGC  CATGGGCTAG  CGCGGCAGCC 8950        8960        8970        8980        8990        9000
      TGCTGGGGGC  GATCCGTTCG  GCGGACGTGG  TGCATCTGCA  TGGCATTGAT  TTTTTCTACG
      ACGACCCCCG  CTAGGCAAGC  CGCCTGCACC  ACGTAGACGT  ACCGTAACTA  AAAAAGATGC 9010        9020        9030        9040        9050        9060
      ACTACCTGGC  GTTGACCAAG  CCGCTGCACG  GCAAGCCGAT  GGTGGTCTCG  ACGCATGGCG
      TGATGGACCG  CAACTGGTTC  GGCGACGTGC  CGTTCGGCTA  CCACCAGAGC  TGCGTACCGC 9070        9080        9090        9100        9110        9120
      GGTTTTTCCA  CACTGCCTAT  GCGTCGCGCA  TGAAGCAGAT  CTGGTTCCAG  ACGCTGACGC
      CCAAAAAGGT  GTGACGGATA  CGCAGCGCGT  ACTTCGTCTA  GACCAAGGTC  TGCGACTGCG 9130        9140        9150        9160        9170        9180
      GTACTTCTGC  GCTGGCCTAT  GCGCGTGTGA  TCGCCACTAG  CGAGAATGAC  GGCGATCTGT
      CATGAAGACG  CGACCGGATA  CGCGCACACT  AGCGGTGATC  GCTCTTACTG  CCGCTAGACA 9190        9200        9210        9220        9230        9240
      TCGCCAAGGT  GGTCGCGCCG  TCGCGCTTGC  GGGTGATCGA  GAACGGTGTC  GACGTGGAGA
      AGCGGTTCCA  CCAGCGCGGC  AGCGCGAACG  CCCACTAGCT  CTTGCCACAG  CTGCACCTCT
```

FIG. 10A-23

```
      9250       9260       9270       9280       9290       9300
AGTATGCAGG GCAGGGCGCT CGAGCGCCGG GACGGACCAT GCTGTATTTC GGGCGTTGGT
TCATACGTCC CGTCCCGCGA GCTCGCGGCC CTGCCTGGTA CGACATAAAG CCCGCAACCA 9310       9320       9330       9340       9350       9360
CGGTCAACAA GGGCCTGATC GAAACGCTTG AATTGCTGCA GGCTGCGCTC ACGCGTGATC
GCCAGTTGTT CCCGGACTAG CTTTGCGAAC TTAACGACGT CCGACGCGAG TGCGCACTAG 9370       9380       9390       9400       9410       9420
CGCAGTGGCG GTTGATCATC GCCGGGCGCG AGTACGATTT GAATGAGGCG GATCTGCGCA
GCGTCACCGC CAACTAGTAG CGGCCCGCGC TCATGCTAAA CTTACTCCGC CTAGACGCGT 9430       9440       9450       9460       9470       9480
AGGCCATCGC CGAACGCGGT TTGCAGGACA AGGTGCAGCT GAGCATGTCG CCATCGCAGC
TCCGGTAGCG GCTTGCGCCA AACGTCCTGT TCCACGTCGA CTCGTACAGC GGTAGCGTCG 9490       9500       9510       9520       9530       9540
AGCAGTTGTG CGCGTTGATG CAGCAGGCGC AGTTCTTCGT GTGCCTGTCG CGGCATGAGG
TCGTCAACAC GCGCAACTAC GTCGTCCGCG TCAAGAAGCA CACGGACAGC GCCGTACTCC 9550       9560       9570       9580       9590       9600
GGTTTGGGAT TGCGGCGGTG GAAGCGATGA GCGCGGGGTT GATCCCGATT CTCAGCGACA
CCAAACCCTA ACGCCGCCAC CTTCGCTACT CGCGCCCCAA CTAGGGCTAA GAGTCGCTGT 9610       9620       9630       9640       9650       9660
TTCCTCCGTT CGTGCGGCTT GCCACCGAGT CCGGACAGGG TGTGATCGTC AATCGCGACA
AAGGAGGCAA GCACGCCGAA CGGTGGCTCA GGCCTGTCCC ACACTAGCAG TTAGCGCTGT
```

FIG. 10A-24

```
           9670       9680       9690       9700       9710       9720
      GGATTCAGGC CGCGGCCGAC AGCGTGCAAG CATTGGCGCT GCAGGCCAAT GCGGATTTCG
      CCTAAGTCCG GCGCCGGCTG TCGCACGTTC GTAACCGCGA CGTCCGGTTA CGCCTAAAGC 9730       9740       9750       9760       9770       9780
      ATGCGCGCCG CACGGCGACC ATGGCGTATG TGGCGCGCTA CGACTGGCGG CACGTGGTGG
      TACGCGCGGC GTGCCGCTGG TACCGCATAC ACCGCGCGAT GCTGACCGCC GTGCACCACC 9790       9800       9810       9820       9830       9840
      GGCGTTATAT CGACGAGTAC CACGCTGCGC TGGGAACACC ACGTACGCAG GAGGCCGTGC
      CCGCAATATA GCTGCTCATG GTGCGACGCG ACCCTTGTGG TGCATGCGTC CTCCGGCACG 9850       9860       9870       9880       9890       9900
      GATGAGCGCG TCTGCTTCGC TGCCAGTGAC GCGTGCTGCT GCGGCGCCCC GGATCACGGT
      CTACTCGCGC AGACGAAGCG ACGGTCACTG CGCACGACGA CGCCGCGGGG CCTAGTGCCA 9910       9920       9930       9940       9950       9960
      GCTGTTCTCC ACCGAAAAGC CGAACGCCAA CACCAACCCG TATCTCACCC AGCTCTACGA
      CGACAAGAGG TGGCTTTTCG GCTTGCGGTT GTGGTTGGGC ATAGAGTGGG TCGAGATGCT 9970       9980       9990      10000      10010      10020
      TGCGCTGCCG GACGCGGTGC AGCCGCGCTT CTTTTCGATG CGCGAGGCGT TGTTGTCGCG
      ACGCGACGGC CTGCGCCACG TCGGCGCGAA GAAAAGCTAC GCGCTCCGCA ACAACAGCGC 10030      10040      10050      10060      10070      10080
      CTACGACGTG CTGCATCTGC ACTGGCCGGA ATATCTGCTG CGCCATCCCA GCAAGATGGG
      GATGCTGCAC GACGTAGACG TGACCGGCCT TATAGACGAC GCGGTAGGGT CGTTCTACCC
```

FIG. 10A-25

```
        10090       10100       10110       10120       10130       10140
    CACGCTGGCC  AAGCAGGCCT  GCGCTGCCTT  GCTGCTGATG  AAGTTGCAGC  TGACCGGCAC
    GTGCGACCGG  TTCGTCCGGA  CGCGACGGAA  CGACGACTAC  TTCAACGTCG  ACTGGCCGTG 10150       10160       10170       10180       10190       10200
    GCCGGTGGTA  CGCACCTTGC  ACAACCTGGC  GCCGCATGAA  GACCGCGGCT  GGCGGGAGCG
    CGGCCACCAT  GCGTGGAACG  TGTTGGACCG  CGGCGTACTT  CTGGCGCCGA  CCGCCCTCGC 10210       10220       10230       10240       10250       10260
    CGCGCTGCTG  CGCTGGATCG  ATCAGCTCAC  GCGGCGCTGG  ATCCGCATCA  ACGCCACTAC
    GCGCGACGAC  GCGACCTAGC  TAGTCGAGTG  CGCCGCGACC  TAGGCGTAGT  TGCGGTGATG 10270       10280       10290       10300       10310       10320
    ACCGGTGCGG  CCGCCGTTCA  CCGACACCAT  CCTGCACGGC  CATTACCGCG  ACTGGTTCGC
    TGGCCACGCC  GGCGGCAAGT  GGCTGTGGTA  GGACGTGCCG  GTAATGGCGC  TGACCAAGCG 10330       10340       10350       10360       10370       10380
    GACGATGGAG  CAGAGCACCA  CGTTGCCTGG  TCGGCTGCTG  CATTTTGGAT  TGATCCGGCC
    CTGCTACCTC  GTCTCGTGGT  GCAACGGACC  AGCCGACGAC  GTAAAACCTA  ACTAGGCCGG 10390       10400       10410       10420       10430       10440
    GTACAAGGGC  GTTGAGGTGT  TGCTCGACGT  CATGCGCGGA  TGTGCAGGAC  CCGCGCCTGA
    CATGTTCCCG  CAACTCCACA  ACGAGCTGCA  GTACGCGCCT  ACACGTCCTG  GGCGCGGACT 10450       10460       10470       10480       10490       10500
    GCCTGCGCAT  CGTCGGCAAC  CCGGCGACGC  CAGGATGCGC  ACGCTGGTCG  AAACCGCCTG
    CGGACGCGTA  GCAGCCGTTG  GGCCGCTGCG  GTCCTACGCG  TGCGACCAGC  TTTGGCGGAC
```

FIG. 10A-26

```
        10510      10520      10530      10540      10550      10560
     CGCGCAGGAT GCACGTATCA GTGCACTGCT GGCCTATGTC GAGGAGCCGG TGCTCGCGCG
     GCGCGTCCTA CGTGCATAGT CACGTGACGA CCGGATACAG CTCCTCGGCC ACGAGCGCGC 10570      10580      10590      10600      10610      10620
     CGAAGTCAGT GCCTGCGAAC TGGTGGTACT GCCATACAAG CAGATGCACA ACTCCGGCAC
     GCTTCAGTCA CGGACGCTTG ACCACCATGA CGGTATGTTC GTCTACGTGT TGAGGCCGTG 10630      10640      10650      10660      10670      10680
     CTTGCTGCTG GCGTTGTCGT TGGCGCGGCC CGTGCTTGCG CCGTGGAGCG AATCGAACGC
     GAACGACGAC CGCAACAGCA ACCGCGCCGG GCACGAACGC GGCACCTCGC TTAGCTTGCG 10690      10700      10710      10720      10730      10740
     CGCGATCGCC GACGAAGTCG GGCCGGGTTG GGTGTTCCTG TACGAAGGCG AGTTCGATGC
     GCGCTAGCGG CTGCTTCAGC CCGGCCCAAC CCACAAGGAC ATGCTTCCGC TCAAGCTACG 10750      10760      10770      10780      10790      10800
     GGCGTTGTTG AGCGGCATGC TCGATCAGGT GCGCGCCGCG CCGCGTGGCC CGGCGCCCGA
     CCGCAACAAC TCGCCGTACG AGCTAGTCCA CGCGCCGCGC GGCGCACCGG GCCGCGGGCT 10810      10820      10830      10840      10850      10860
     TCTTTCACAA CGTGATTGGC CACGGATCGG GCAATTGCAC TATCGCACCT ACTTGGAAGC
     AGAAAGTGTT GCACTAACCG GTGCCTAGCC CGTTAACGTG ATAGCGTGGA TGAACCTTCG 10870      10880      10890      10900      10910      10920
     GCTCGGCAAG GATGGAGACG CCGCGCTGTG ACCGCAGAGA CATCGACCAT GACTTCCCCA
     CGAGCCGTTC CTACCTCTGC GGCGCGACAC TGGCGTCTCT GTAGCTGGTA CTGAAGGGGT
```

FIG. 10A-27

```
          10930      10940      10950      10960      10970      10980
     ACACCGCCGC CGCGCAGCCT CGGGTCGCGT GCCGCTGGCG CCGCCGTGAC CATGATCGGG
     TGTGGCGGCG GCGCGTCGGA GCCCAGCGCA CGGCGACCGC GGCGGCACTG GTACTAGCCC 10990      11000      11010      11020      11030      11040
     CAGTCGGCCA AGATGATCGT GCAGTTCGGC GGCATCGTGC TGCTGGCACG CTTGTTGACG
     GTCAGCCGGT TCTACTAGCA CGTCAAGCCG CCGTAGCACG ACGACCGTGC GAACAACTGC 11050      11060      11070      11080      11090      11100
     CCGTACGACT ACGGCTTGAT GGCCATGGTG ACCGCCATCG TGGGGCCGC CGAAATCCTG
     GGCATGCTGA TGCCGAACTA CCGGTACCAC TGGCGGTAGC ACCCCGGCG GCTTTAGGAC 11110      11120      11130      11140      11150      11160
     CGCGACTTCG GTCTCTCCGC AGCCGCCGTC CAGGCGAAAC ATGTCAGCCG CGAGCAACGC
     GCGCTGAAGC CAGAGAGGCG TCGGCGGCAG GTCCGCTTTG TACAGTCGGC GCTCGTTGCG 11170      11180      11190      11200      11210      11220
     GACAACCTGT TCTGGATCAA TAGCGGCATC GGTCTGATGC TGTCGGTGGT GGTGTTCGCC
     CTGTTGGACA AGACCTAGTT ATCGCCGTAG CCAGACTACG ACAGCCACCA CCACAAGCGG 11230      11240      11250      11260      11270      11280
     AGCGCGCACT GGATTGCGGA CTTTTATCAC GAGCCCGCAT TGGTGACGAT TTCGCAGGCA
     TCGCGCGTGA CCTAACGCCT GAAAATAGTG CTCGGGCGTA ACCACTGCTA AAGCGTCCGT 11290      11300      11310      11320      11330      11340
     TTGGCGGTGA CCTTCCTGCT CAACGGGATG ACCACCCAAT ACCGCGCACA CCTCAGTCGG
     AACCGCCACT GGAAGGACGA GTTGCCCTAC TGGTGGGTTA TGGCGCGTGT GGAGTCAGCC
```

FIG. 10A-28

```
         11350      11360      11370      11380      11390      11400
    GGGCTGCGCT TCGGTCAGGT AGCGCTGAGC GATGTGGGTT CGCAGGTGTT GGGGTTGGGT
    CCCGACGCGA AGCCAGTCCA TCGCGACTCG CTACACCCAA GCGTCCACAA CCCCAACCCA 11410      11420      11430      11440      11450      11460
    GCTGCAGTTG CGGCCGCCTT GGCCGGCTGG GGCTACTGGG CGTTGATCGT GCAGCAGGTG
    CGACGTCAAC GCCGGCGGAA CCGGCCGACC CCGATGACCC GCAACTAGCA CGTCGTCCAC 11470      11480      11490      11500      11510      11520
    GTGCAGGCCA TCGTGAACCT GATTATCGCT GGCGCATGTG CACGCTGGTT GCCGCGCGGG
    CACGTCCGGT AGCACTTGGA CTAATAGCGA CCGCGTACAC GTGCGACCAA CGGCGCGCCC 11530      11540      11550      11560      11570      11580
    TACGCGCGGC AGGCGCCGAT GCGCGATTTC ATGAGCTTTG GCTGGAACCT GATGGCGGCG
    ATGCGCGCCG TCCGCGGCTA CGCGCTAAAG TACTCGAAAC CGACCTTGGA CTACCGCCGC 11590      11600      11610      11620      11630      11640
    CAGCTGCTCG GCTATGCGAG CCGCAACGTT GGCCAGGTGA TCATCGGCTG GAGGACCGGG
    GTCGACGAGC CGATACGCTC GGCGTTGCAA CCGGTCCACT AGTAGCCGAC CTCCTGGCCC 11650      11660      11670      11680      11690      11700
    CCCGACGCGC TGGGTCTGTA CAACCGTGCC TTCCAGTTGT TGATGATGCC GTTGAATCAG
    GGGCTGCGCG ACCCAGACAT GTTGGCACGG AAGGTCAACA ACTACTACGG CAACTTAGTC 11710      11720      11730      11740      11750      11760
    ATCAATGCGC CTGCGACTAG TGTGGCGCTG CCGGTGTTGT CGCAATTGCA GGATGAGCGC
    TAGTTACGCG GACGCTGATC ACACCGCGAC GGCCACAACA GCGTTAACGT CCTACTCGCG
```

FIG. 10A-29

```
          11770      11780      11790      11800      11810      11820
       GAGCGCTACA GCGCTTTTCT GTTGCGCGGC CAGACGGTCA TGGTGCATTT GATCTTTGCG
       CTCGCGATGT CGCGAAAAGA CAACGCGCCG GTCTGCCAGT ACCACGTAAA CTAGAAACGC 11830      11840      11850      11860      11870      11880
       CTGTTCGCGT TTGCCTGTGC ACTGGCCATG CCGCTCATCG TCCTGGTGCT GGGTGAGCAG
       GACAAGCGCA AACGGACACG TGACCGGTAC GGCGAGTAGC AGGACCACGA CCCACTCGTC 11890      11900      11910      11920      11930      11940
       TGGCGGGAAG CGGTGCCGCT GTTTCAGGTG TTGACGCTGG GCGGTATCTT CCAGACGGCG
       ACCGCCCTTC GCCACGGCGA CAAAGTCCAC AACTGCGACC CGCCATAGAA GGTCTGCCGC 11950      11960      11970      11980      11990      12000
       TCGTACGCAA CCTACTGGGT GTTCCTGTCG AAGGGGTTGA TGCGCGAGCA GTTGGTGTAT
       AGCATGCGTT GGATGACCCA CAAGGACAGC TTCCCCAACT ACGCGCTCGT CAACCACATA 12010      12020      12030      12040      12050      12060
       TCGTTGGTCG GTCGCATCCT GCTCATCGCC TGCATTTTTG TTGGCTCCCG CTGGGGGGCC
       AGCAACCAGC CAGCGTAGGA CGAGTAGCGG ACGTAAAAAC AACCGAGGGC GACCCCCCGG 12070      12080      12090      12100      12110      12120
       ATGGGCGTGG CGATCGGCTA CTCATTCGGC CTGCTGTTGA TCTGGCCGCT GTCGCTGGTC
       TACCCGCACC GCTAGCCGAT GAGTAAGCCG GACGACAACT AGACCGGCGA CAGCGACCAG 12130      12140      12150      12160      12170      12180
       TGGATCGGCA AGATCACGGA CGCACCGGTC GGTGCGTTGT TCGTCAATGC CATGCGTGCG
       ACCTAGCCGT TCTAGTGCCT GCGTGGCCAG CCACGCAACA AGCAGTTACG GTACGCACGC
```

FIG. 10A-30

```
         12190       12200       12210       12220       12230       12240
    CTGGTGGCCT  ACGGTATCGC  CGGCGGCTGC  GCTTATTACG  CATCGGTCAC  TGTCGGTGGT
    GACCACCGGA  TGCCATAGCG  GCCGCCGACG  CGAATAATGC  GTAGCCAGTG  ACAGCCACCA 12250       12260       12270       12280       12290       12300
    CCATTGTGGC  AGCAGCTGCT  GGTCGGCGCC  GGCGCGATGG  CGCTGGTCTG  TCTGCTCGCA
    GGTAACACCG  TCGTCGACGA  CCAGCCGCGG  CCGCGCTACC  GCGACCAGAC  AGACGAGCGT 12310       12320       12330       12340       12350       12360
    TTGGCATGGC  CGGGATTCCG  GCGTGACGTG  GTCGCTATCG  TCAATATCCG  CAAGCTGCTC
    AACCGTACCG  GCCCTAAGGC  CGCACTGCAC  CAGCGATAGC  AGTTATAGGC  GTTCGACGAG 12370       12380       12390       12400       12410       12420
    ACGCAGGCGA  AGGCGCGCCG  ATGACACTGC  ACTGCGGTAC  TGGAATGTTG  GACTTCGAAA
    TGCGTCCGCT  TCCGCGCGGC  TACTGTGACG  TGACGCCATG  ACCTTACAAC  CTGAAGCTTT 12430       12440       12450       12460       12470       12480
    CTTCCCACTC  TTGCAAAGGA  CACGGCCTAT  GAGCGTCTCT  CCCGCAGCTC  CAGCTTCCGG
    GAAGGGTGAG  AACGTTTCCT  GTGCCGGATA  CTCGCAGAGA  GGGCGTCGAG  GTCGAAGGCC 12490       12500       12510       12520       12530       12540
    CATTCGCCGT  CCCTGCTATC  TGGTCTTGTC  TGCTCACGAT  TTCCGCACGC  CACGTCGGGC
    GTAAGCGGCA  GGGACGATAG  ACCAGAACAG  ACGAGTGCTA  AAGGCGTGCG  GTGCAGCCCG 12550       12560       12570       12580       12590       12600
    TAACATCCAT  TTCATCACCG  ATCAGTTGGC  TTTGCGTGGC  ACGACGCGTT  TTTTTTCGTT
    ATTGTAGGTA  AAGTAGTGGC  TAGTCAACCG  AAACGCACCG  TGCTGCGCAA  AAAAAAGCAA
```

FIG. 10A-31

```
         12610      12620      12630      12640      12650      12660
    GCGATACAGC AGACTCTCCC GCATGAAGGG AGATATGCGC CTGCCGCTGG ATGACACCGC
    CGCTATGTCG TCTGAGAGGG CGTACTTCCC TCTATACGCG GACGGCGACC TACTGTGGCG 12670      12680      12690      12700      12710      12720
    AAATACCGTT GTCTCGCACA ACGGTGTGGA CTGTTACCTG TGGCGCACGA CGGTGCATCC
    TTTATGGCAA CAGAGCGTGT TGCCACACCT GACAATGGAC ACCGCGTGCT GCCACGTAGG 12730      12740      12750      12760      12770      12780
    ATTCAATACA CGCCGGAGCT GGCTACGTCC TGTGGAAGAC GCCATGTTCC GCTGGTATGC
    TAAGTTATGT GCGGCCTCGA CCGATGCAGG ACACCTTCTG CGGTACAAGG CGACCATACG 12790      12800      12810      12820      12830      12840
    CGCGCATCCG CCAAAGCAGT TGCTGGACTG GATGCGCGAG TCCGATGTCA TCGTGTTTGA
    GCGCGTAGGC GGTTTCGTCA ACGACCTGAC CTACGCGCTC AGGCTACAGT AGCACAAACT 12850      12860      12870      12880      12890      12900
    AAGCGGGATC GCAGTCGCAT TCATCGAGCT TGCCAAGCGG GTCAATCCGG CTGCCAAACT
    TTCGCCCTAG CGTCAGCGTA AGTAGCTCGA ACGGTTCGCC CAGTTAGGCC GACGGTTTGA 12910      12920      12930      12940      12950      12960
    GGTCTATCGC GCGTCGGACG GGCTGAGCAC CATCAACGTG GCGTCTTACA TCGAGCGCGA
    CCAGATAGCG CGCAGCCTGC CCGACTCGTG GTAGTTGCAC CGCAGAATGT AGCTCGCGCT 12970      12980      12990      13000      13010      13020
    GTTCGACCGC GTGGCTCCGA CGCTGGACGT CATTGCCTTG GTGTCGCCCG CGATGGCCGC
    CAAGCTGGCG CACCGAGGCT GCGACCTGCA GTAACGGAAC CACAGCGGGC GCTACCGGCG
```

FIG. 10A-32

```
         13030      13040      13050      13060      13070      13080
      AGAAGTAGCA AGCCGCGACA ACGTCTTCCA TGTAGGTCAC GGCGTGGACC ACAACCTCGA
      TCTTCATCGT TCGGCGCTGT TGCAGAAGGT ACATCCAGTG CCGCACCTGG TGTTGGAGCT 13090      13100      13110      13120      13130      13140
      TCAGCTCGGC GACCCGTCGC CGTATGCCGA AGGCATCCAT GCAGTTGCGG TCGGGTCGAT
      AGTCGAGCCG CTGGGCAGCG GCATACGGCT TCCGTAGGTA CGTCAACGCC AGCCCAGCTA 13150      13160      13170      13180      13190      13200
      GCTGTTTGAT CCTGAATTTT TCGTCGTTGC CAGCAAGGCC TTTCCGCAAG TGACCTTCCA
      CGACAAACTA GGACTTAAAA AGCAGCAACG GTCGTTCCGG AAAGGCGTTC ACTGGAAGGT 13210      13220      13230      13240      13250      13260
      CGTGATCGGC TCCGGGATGG GCCGCCATCC GGGCTACGGC GACAATGTCA TTGTCTATGG
      GCACTAGCCG AGGCCCTACC CGGCGGTAGG CCCGATGCCG CTGTTACAGT AACAGATACC 13270      13280      13290      13300      13310      13320
      CGAAATGAAG CACGCGCAGA CGATTGGCTA TATCAAGCAC GCACGTTTCG GCATTGCGCC
      GCTTTACTTC GTGCGCGTCT GCTAACCGAT ATAGTTCGTG CGTGCAAAGC CGTAACGCGG 13330      13340      13350      13360      13370      13380
      TTACGCGTCC GAGCAGGTGC CGGTGTATCT GGCAGACAGC TCAATGAAAT TGCTGCAATA
      AATGCGCAGG CTCGTCCACG GCCACATAGA CCGTCTGTCG AGTTACTTTA ACGACGTTAT 13390      13400      13410      13420      13430      13440
      CGACTTTTTC GGCTTGCCGG CGGTGTGCCC GAATGCTGTG GTGGGGCCGT ACAAATCGCG
      GCTGAAAAAG CCGAACGGCC GCCACACGGG CTTACGACAC CACCCCGGCA TGTTTAGCGC
```

FIG. 10A-33

```
          13450      13460      13470      13480      13490      13500
     CTTCGGGTAC ACGCCAGGCA ATGCCGATTC GGTGATTGCC GCCATTACCC AGGCACTGGA
     GAAGCCCATG TGCGGTCCGT TACGGCTAAG CCACTAACGG CGGTAATGGG TCCGTGACCT 13510      13520      13530      13540      13550      13560
     AGCACCGCGT GTACGTTACC GCCAGTGTCT CAACTGGTCC GACACCACCG ACCGCGTGCT
     TCGTGGCGCA CATGCAATGG CGGTCACAGA GTTGACCAGG CTGTGGTGGC TGGCGCACGA 13570      13580      13590      13600      13610      13620
     CGACCCACGG GCGTACCCGG AAACCCGTCT TTATCCGCAC CCCCCCACCG CCGCGCCGCA
     GCTGGGTGCC CGCATGGGCC TTTGGGCAGA AATAGGCGTG GGGGGGTGGC GGCGCGGCGT 13630      13640      13650      13660      13670      13680
     GCTCTCTTCG GAGGCAGCGC TCTCACATTG AGGAGGCGCT TTTTTGATCA CGTTTGAAGG
     CGAGAGAAGC CTCCGTCGCG AGAGTGTAAC TCCTCCGCGA AAAAACTAGT GCAAACTTCC 13690      13700      13710      13720      13730      13740
     AGGATCCCTG TCATGGCCAA CGCTTTACTG CAGAAATGGG TGGAACGGGC GGAACGTCGC
     TCCTAGGGAC AGTACCGGTT GCGAAATGAC GTCTTTACCC ACCTTGCCCG CCTTGCAGCG 13750      13760      13770      13780      13790      13800
     GCATTGTTCT GGTGGCAGCC CAAAAACGGT GGCGTGAACA TGGGGGATCA CCTGTCGAAG
     CGTAACAAGA CCACCGTCGG GTTTTTGCCA CCGCACTTGT ACCCCCTAGT GGACAGCTTC 13810      13820      13830      13840      13850      13860
     GTGATCGTGT CGTGCGTGTT GGCGTTGCAG GACAAGACAC TTCTGGAAAA ACGCGATTTG
     CACTAGCACA GCACGCACAA CCGCAACGTC CTGTTCTGTG AAGACCTTTT TGCGCTAAAC
```

FIG. 10A-34

```
          13870      13880      13890      13900      13910      13920
       CGCCAGAAGC TGATCGCAAC CGGGTCGGTG CTGCATTTCG CCAAAGATGG CGACACCGTG
       GCGGTCTTCG ACTAGCGTTG GCCCAGCCAC GACGTAAAGC GGTTTCTACC GCTGTGGCAC 13930      13940      13950      13960      13970      13980
       TGGGGAAGCG GTATCAACGG CAAGATTCCG GCCGAGCGCA ATACGTTCAG CACGCTGGAC
       ACCCCTTCGC CATAGTTGCC GTTCTAAGGC CGGCTCGCGT TATGCAAGTC GTGCGACCTG 13990      14000      14010      14020      14030      14040
       GTACGCGCGG TACGCGGTCC CAAGACCCGC GCATTTTGC  TGGAACGTGG CATCGCAGTG
       CATGCGCGCC ATGCGCCAGG GTTCTGGGCG CGTAAAAACG ACCTTGCACC GTAGCGTCAC 14050      14060      14070      14080      14090      14100
       CCTGAGGTCT ACGGAGACCC GGGATTGCTG ACCCCGATGT TTTTCCCCGC CGACGCCCTC
       GGACTCCAGA TGCCTCTGGG CCCTAACGAC TGGGGCTACA AAAGGGGCG  GCTGCGGGAG 14110      14120      14130      14140      14150      14160
       GGCCCGGTCA CCAAGCGCCC GTTCGCGATC GTGCCGCACT TCAACGAGCC GGTTGAGAAG
       CCGGGCCAGT GGTTCGCGGG CAAGCGCTAG CACGGCGTGA AGTTGCTCGG CCAACTCTTC 14170      14180      14190      14200      14210      14220
       TACAGCGCCT ACGCCGAGCA TCTGGTGTTT CCCAACGTCA AGCCGGCCAC CTTCATGAGT
       ATGTCGCGGA TGCGGCTCGT AGACCACAAA GGGTTGCAGT TCGGCCGGTG GAAGTACTCA 14230      14240      14250      14260      14270      14280
       GCGCTGCTGG GTGCGGAATT TGTCATCAGC AGTTCGCTGC ATGGCCTGAT CCTGGCCGAA
       CGCGACGACC CACGCCTTAA ACAGTAGTCG TCAAGCGACG TACCGGACTA GGACCGGCTT
```

FIG. 10A-35

```
        14290       14300       14310       14320       14330       14340
   GCCTATGGCA  TCCCGGCGGT  GTATCTGGAC  TGGGGCAACG  GCGAAGACCG  TTTCAAGTAC
   CGGATACCGT  AGGGCCGCCA  CATAGACCTG  ACCCCGTTGC  CGCTTCTGGC  AAAGTTCATG 14350       14360       14370       14380       14390       14400
   GACGACTACT  ACCACGGCAC  CGGGCGCATG  CAATGGCATG  CCGGCCACAG  CGTGGAAGAA
   CTGCTGATGA  TGGTGCCGTG  GCCCGCGTAC  GTTACCGTAC  GGCCGGTGTC  GCACCTTCTT 14410       14420       14430       14440       14450       14460
   TGCATGGAAC  TGGGCGGCAA  CGGCAGTTTC  GATCTTGAAC  GCTTGCAGGC  AGGATTGCTG
   ACGTACCTTG  ACCCGCCGTT  GCCGTCAAAG  CTAGAACTTG  CGAACGTCCG  TCCTAACGAC 14470       14480       14490       14500       14510       14520
   GCTGCGTTCC  CTTACGATTT  GTGGTGAAAC  GACAATGCAT  GGCCAGCCAG  CAGGTGTGGA
   CGACGCAAGG  GAATGCTAAA  CACCACTTTG  CTGTTACGTA  CCGGTCGGTC  GTCCACACCT 14530       14540       14550       14560       14570       14580
   GACGGCAACG  GTGAGTGCAG  CGACACCTGC  GCAAGGGGTG  GTGATTCCGC  TGGGCGGCTT
   CTGCCGTTGC  CACTCACGTC  GCTGTGGACG  CGTTCCCCAC  CACTAAGGCG  ACCCGCCGAA 14590       14600       14610       14620       14630       14640
   CCCGGTGTTG  TCGACCACGC  AGGAAGCCTT  CGCGCTGGAT  CTGTTCCATG  CGCTGGCCGC
   GGGCCACAAC  AGCTGGTGCG  TCCTTCGGAA  GCGCGACCTA  GACAAGGTAC  GCGACCGGCG 14650       14660       14670       14680       14690       14700
   GCATCAGCCG  CGCCGGGTGT  TTTTCGCGAA  CACCAACTTC  ATCGTGCAGT  GCCAGGCGCT
   CGTAGTCGGC  GCGGCCCACA  AAAAGCGCTT  GTGGTTGAAG  TAGCACGTCA  CGGTCCGCGA
```

FIG. 10A-36

```
           14710       14720       14730       14740       14750       14760
        GCGCGCGCGC  ATGCAGGCGC  CGGCAGTGCG  CATCGTCAAC  GATGGGATCG  GCATGGATCT
        CGCGCGCGCG  TACGTCCGCG  GCCGTCACGC  GTAGCAGTTG  CTACCCTAGC  CGTACCTAGA 14770       14780       14790       14800       14810       14820
        GGCGGCGCGC  CTGATCCATG  GCCGCCGGTT  CGCCGGCAAC  CTCAACGGCA  CCGACCTGAT
        CCGCCGCGCG  GACTAGGTAC  CGGCGGCCAA  GCGGCCGTTG  GAGTTGCCGT  GGCTGGACTA 14830       14840       14850       14860       14870       14880
        TCCGTACCTT  TGCCGCGAGG  CCGCGCAGCC  GCTCAAGTTC  TTCCTGCTCG  GCGGCCGCCC
        AGGCATGGAA  ACGGCGCTCC  GGCGCGTCGG  CGAGTTCAAG  AAGGACGAGC  CGCCGGCGGG 14890       14900       14910       14920       14930       14940
        GGGCGTGGGC  AAGACCGCCG  CGGCGACCTT  GACCGGAACG  CTGGGCCAGC  AGGTCGTGGG
        CCCGCACCCG  TTCTGGCGGC  GCCGCTGGAA  CTGGCCTTGC  GACCCGGTCG  TCCAGCACCC 14950       14960       14970       14980       14990       15000
        CATGTGCGAT  GGGTATGGCG  AATTTGCGGC  GGCGGGCGAG  GGCCTGGCCG  AGCGCATCAA
        GTACACGCTA  CCCATACCGC  TTAAACGCCG  CCGCCCGCTC  CCGGACCGGC  TCGCGTAGTT 15010       15020       15030       15040       15050       15060
        TCGCTCCGGC  GCCGATGTGC  TGTTGGTGGC  CTTCGGCAAC  CCGCTGCAGG  AGCGGTGGAT
        AGCGAGGCCG  CGGCTACACG  ACAACCACCG  GAAGCCGTTG  GGCGACGTCC  TCGCCACCTA 15070       15080       15090       15100       15110       15120
        CCTGGACCAC  AGCGAGGCCT  TGCAGGTGCC  GCTGGTGTTC  GGCGTGGGCG  CCTTGCTGGA
        GGACCTGGTG  TCGCTCCGGA  ACGTCCACGG  CGACCACAAG  CCGCACCCGC  GGAACGACCT
```

FIG. 10A-37

```
         15130      15140      15150      15160      15170      15180
     TTTTCTCTCC GGCACTGCCA AGCGCGCGCC CAACTGGGTG CGCCGTTTGC ATATGGAATG
     AAAAGAGAGG CCGTGACGGT TCGCGCGCGG GTTGACCCAC GCGGCAAACG TATACCTTAC 15190      15200      15210      15220      15230      15240
     GATGTACCGG CTGCTCAACG AGCCGCGCCG GTTGCTCAAG CGCTACAGCT GGGATCTGCT
     CTACATGGCC GACGAGTTGC TCGGCGCGGC CAACGAGTTC GCGATGTCGA CCCTAGACGA 15250      15260      15270      15280      15290      15300
     GGTGTTCTTC CGCACCTGCC TGCGTGCGGG CAAACAGCTG GCGTGATGCA CGGCGGCGGT
     CCACAAGAAG GCGTGGACGG ACGCACGCCC GTTTGTCGAC CGCACTACGT GCCGCCGCCA 15310      15320      15330      15340      15350      15360
     GTGTGGCCTA GCATGCGTGC ATGCATCCAA CCGCCGCCGC GCTGATTCGA ACATTGGGCC
     CACACCGGAT CGTACGCACG TACGTAGGTT GGCGGCGGCG CGACTAAGCT TGTAACCCGG 15370      15380      15390      15400      15410      15420
     TTGCCCCCCA TCCGGAGGGC GGCCACTACC GGCGCGTGTA CGCGTCGACG CGCCAGGTGC
     AACGGGGGGT AGGCCTCCCG CCGGTGATGG CCGCGCACAT GCGCAGCTGC GCGGTCCACG 15430      15440      15450      15460      15470      15480
     TGGATGACAG CGGTGCGCCG CCGCGTCCGG CGCTGACCGC CATCCGCTTC CTGTTGTGCG
     ACCTACTGTC GCCACGCGGC GGCGCAGGCC GCGACTGGCG GTAGGCGAAG GACAACACGC 15490      15500      15510      15520      15530      15540
     CAGGCGAAGC CAGTCGCTGG CATCGGGTGG ATGCCGAGGA GTGCTGGCAC TGGCAGCAAG
     GTCCGCTTCG GTCAGCGACC GTAGCCCACC TACGGCTCCT CACGACCGTG ACCGTCGTTC
```

FIG. 10A-38

```
         15550      15560      15570      15580      15590      15600
     GTGCGCCGCT GGAGTTGCTG ATCTTCGACG AAGCGAGCGG GCAGTTGCGG CGCGAAGTGC
     CACGCGGCGA CCTCAACGAC TAGAAGCTGC TTCGCTCGCC CGTCAACGCC GCGCTTCACG 15610      15620      15630      15640      15650      15660
     TGGACGCCGC AGAGCGCGGC GACGCCATGC ACGTGGTGCC GGCCGGCTGC TGGCAGGCGG
     ACCTGCGGCG TCTCGCGCCG CTGCGGTACG TGCACCACGG CCGGCCGACG ACCGTCCGCC 15670      15680      15690      15700      15710      15720
     CGCGCTCGCT GGGGGACTTC ACCCTGGTGG GCTGCACGGT TTCGCCAGGG TTTGTCTGGG
     GCGCGAGCGA CCCCCTGAAG TGGGACCACC CGACGTGCCA AGCGGTCCC AAACAGACCC 15730      15740      15750      15760      15770      15780
     AAGGTTTCGC GCTGCTCGAA GACGGCTCGC CGCTGGCGGC ACAGCTGGCC GCGTTGGTTG
     TTCCAAAGCG CGACGAGCTT CTGCCGAGCG GCGACCGCCG TGTCGACCGG CGCAACCAAC 15790      15800      15810      15820      15830      15840
     CCGAAGGCGC CGCGCCGGAG CCGCCAACGC TTCCCTAACG CGTGCGGGCC CGCGTTCGCG
     GGCTTCCGCG GCGCGGCCTC GGCGGTTGCG AAGGGATTGC GCACGCCCGG GCGCAAGCGC 15850      15860      15870      15880      15890      15900
     TAGTGTCCGC GTTCCAACCG GGAGGCGGTA CGTGATGCAG CGCAGGGGGG CGGTGTGGCG
     ATCACAGGCG CAAGGTTGGC CCTCCGCCAT GCACTACGTC GCGTCCCCCC GCCACACCGC 15910      15920      15930      15940      15950      15960
     GGCAGGAATC GCGTTGGTGT CGTTGTTGGC ACCGATGCTG GCGTGTGCCG TCGAGGTGGC
     CCGTCCTTAG CGCAACCACA GCAACAACCG TGGCTACGAC CGCACACGGC AGCTCCACCG
```

FIG. 10A-39

```
        15970      15980      15990      16000      16010      16020
   CGTACAGGCG CCGGCAGCGC CGCCAACGGT GGTCGATCTG GAAGCCATGG TGGTGCGCGG
   GCATGTCCGC GGCCGTCGCG GCGGTTGCCA CCAGCTAGAC CTTCGGTACC ACCACGCGCC 16030      16040      16050      16060      16070
   GCAGCAACCC GGCCCCGGCC TGTGGAAGGT CAGCAAGGGC GACCACGTGC TGTGGATCC
   CGTCGTTGGG CCGGGGCCGG ACACCTTCCA GTCGTTCCCG CTGGTGCACG ACACCTAGG-
```

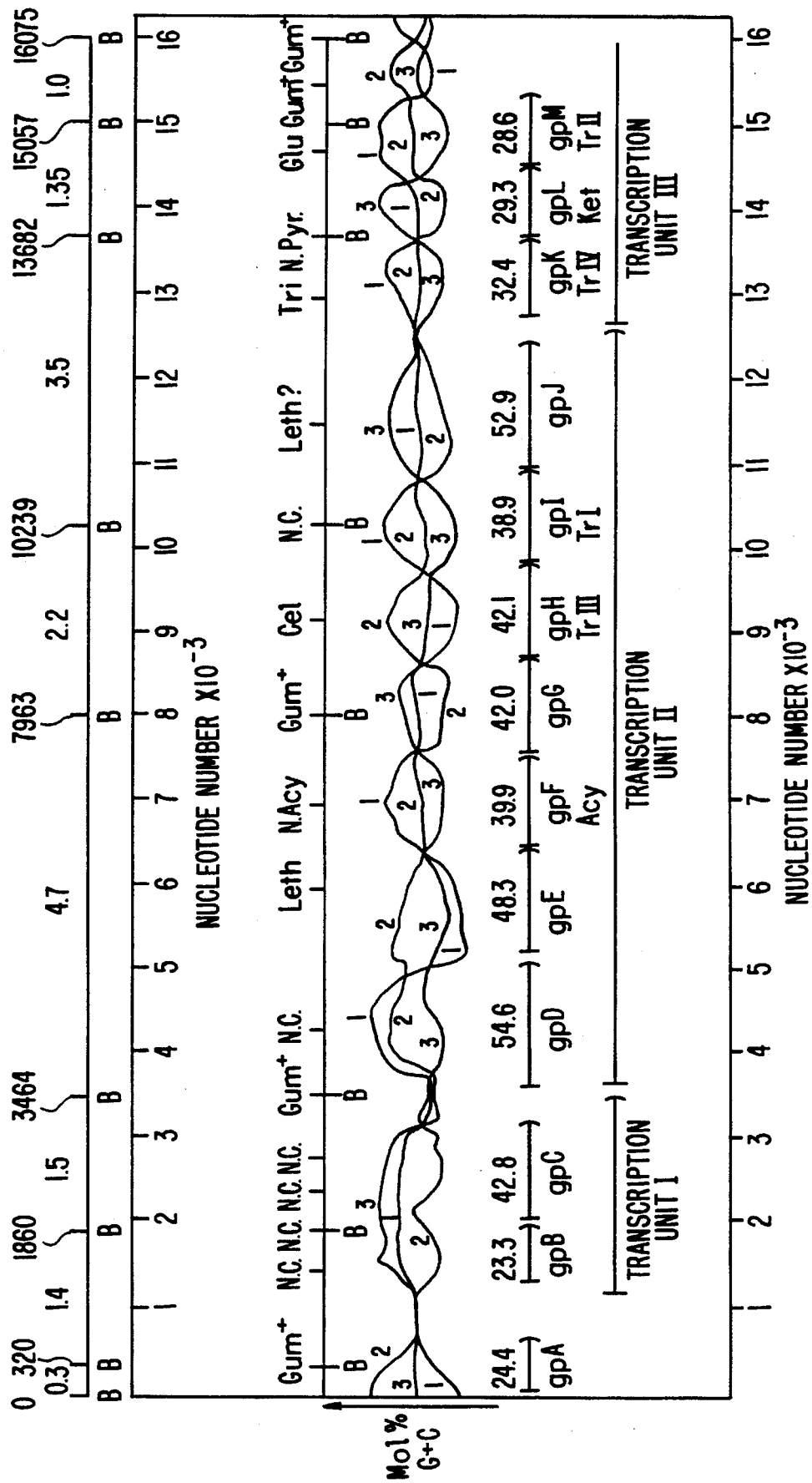
FIG. 11. ORGANIZATION AND STRUCTURE OF THE GUM GENE CLUSTER

FIG. 12A (gpA)
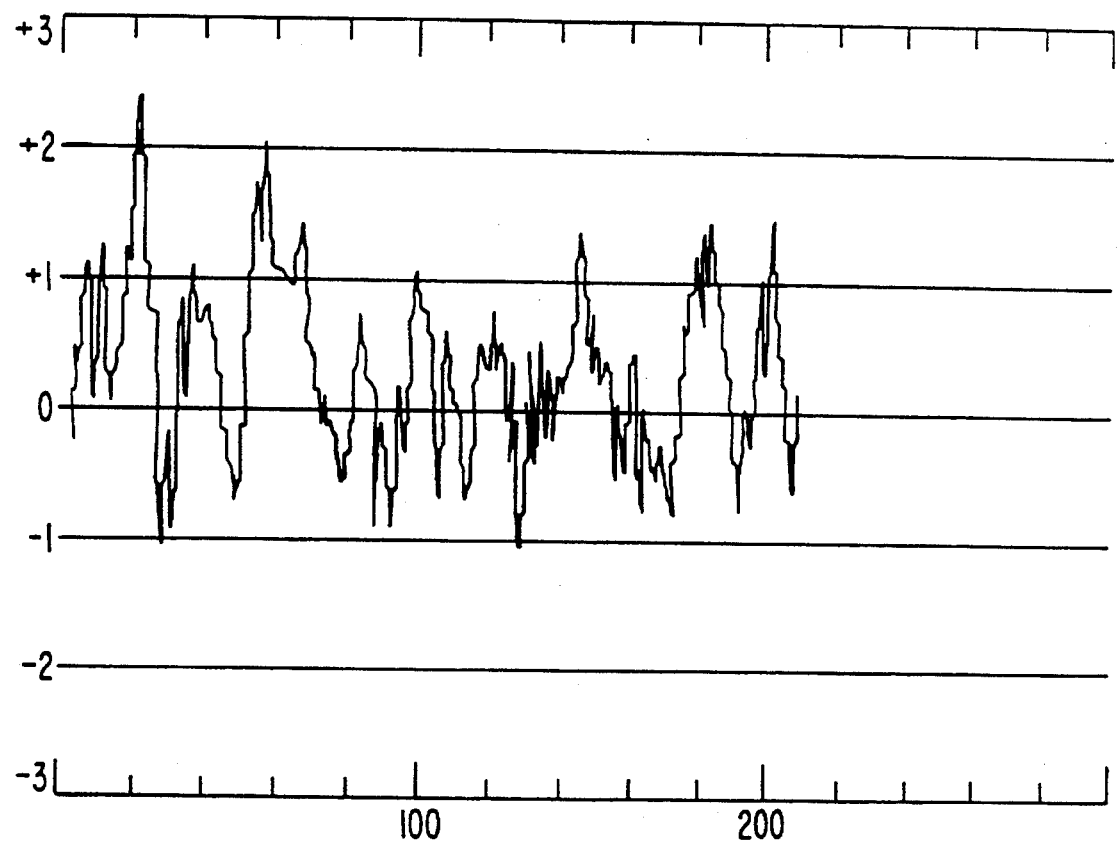
MOLECULAR WEIGHT = 24.4 kD
HYDROPHOBIC RESIDUES = 31.5%
```
M A L T K A E M A E R L F D E V G L N K R E A K E F V D A F
F D V L R D A L E Q G R Q V K L S G F G N F D L R R K N Q R
P G R N P K T G E E I P I S A R T V V T F R P G Q K L Q G T
G W R L M L D F G S N R E L P P I P A K R Y F T I G E V S E
L C D V K P H V L R Y W E T E F P S L E A S Q A A R N R R Y
Y Q R H D V V M V R Q I R G L L Y E Q G Y T I G G A R L R L
E G D G A K S E S A L S N Q I I K Q V R M E L E E V L Q L L
R R
```

FIG. 12B(gpB)
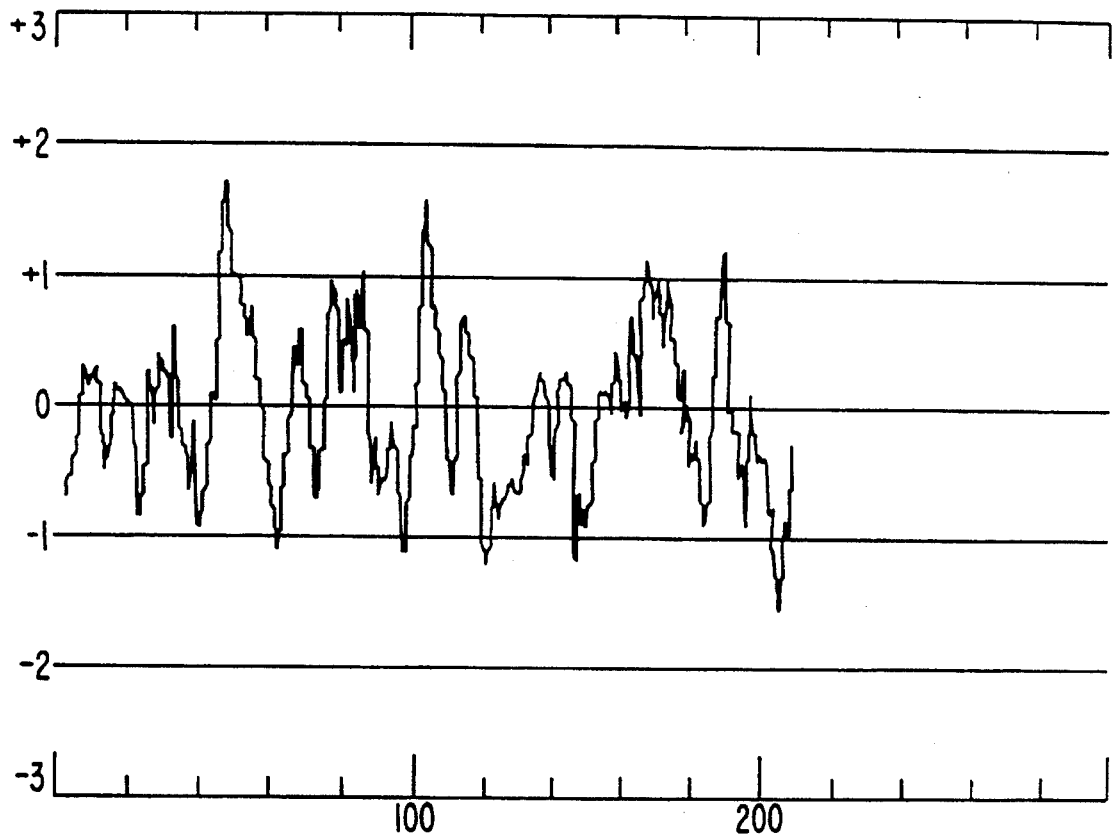
MOLECULAR WEIGHT = 23.3 kD
HYDROPHOBIC RESIDUES = 36.4%
```
M S L G A C S T G P E M A S S L P H P D P L A M S T V Q P E
Y R L A P G D L L L V K V F Q I D D L E R Q V R I D Q N G H
I S L P L I G D V K A A G L G V G E L E K L V A D R Y R A G
Y L Q Q P Q I S V F V Q E S N G R R V T V T G A V D E P G I
Y P V I G A N L T L Q Q A I A Q A K G V S T V A S R G N V I
V F R M V N G Q K M I A R F D L T E I E K G A N P D P E I Y
G G D I V V V Y R S D A R V W L R T M L E L T P L V M V W R
A Y R
```

FIG. 12C(gpC)

MOLECULAR WEIGHT = 42.8 kD
HYDROPHOBIC RESIDUES = 32.0 %

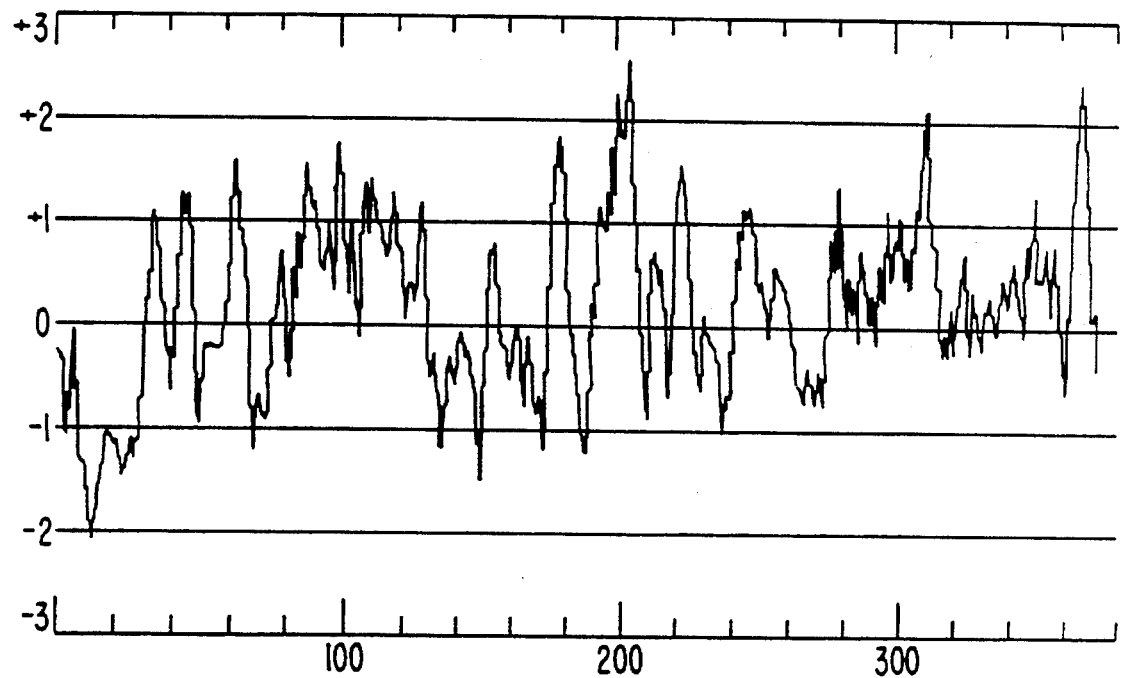

```
M D Y W R A L V S Q L W L I I L I A V G A L L L A F G I T M
L M P E K Y R A T S T L Q I E R D S L N V V N V D N L M P V
E S P Q D R D F Y Q T Q Y Q L L Q S R S L A R A V I R E A K
L D Q E P A F K E Q V E E A L A K A A E K N P E A G K S L D
S R Q A I V E R S L T D T L L A G L V V E P I L N S R L V Y
V N Y D S P D P V L A A K I A N T Y P K V F I V S T Q E R R
M K A S S F A T Q F L A E R L K Q L R E K V E D S E K D L V
S Y S T E E Q I V S V G D D K P S L P A Q N L T D L N A L L
A S A Q D A R I K A E S A W R Q A S S G D G M S L P Q V L S
S P L I Q S L R S E Q V R L T S E Y Q Q K L S T F K P D Y P
E M Q R L K A Q I E E S R R Q I N G E V I N I R Q S L K A T
Y D A S V H Q E Q L L N D R I A G L R S N E L D L Q S R S I
R Y N M L K R E R R H Q P P A L R
```

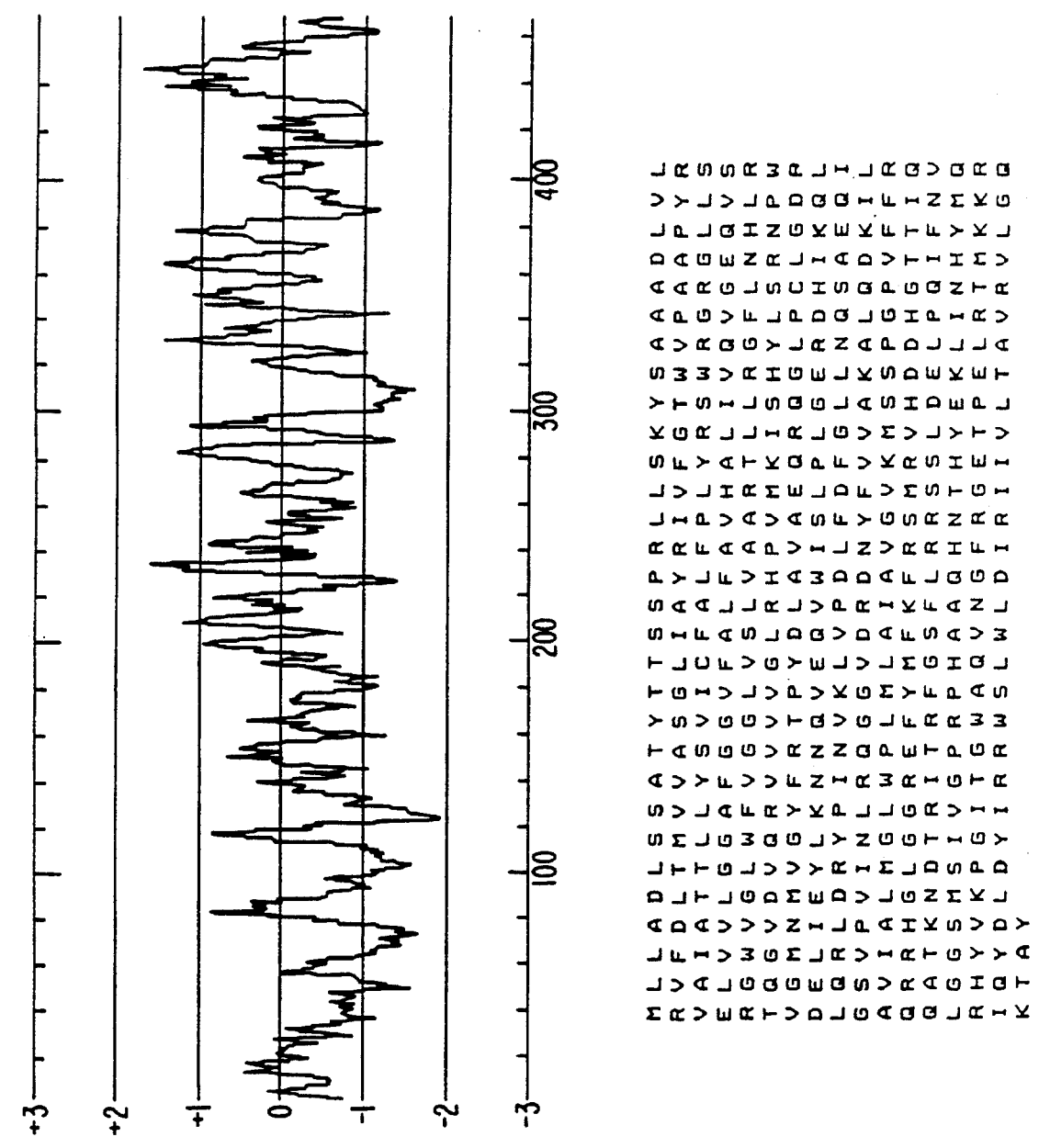
FIG. 12D(gpD)
MOLECULAR WEIGHT=54.6 kD
HYDROPHOBIC RESIDUES=41.4%

FIG. 12E (gpE)

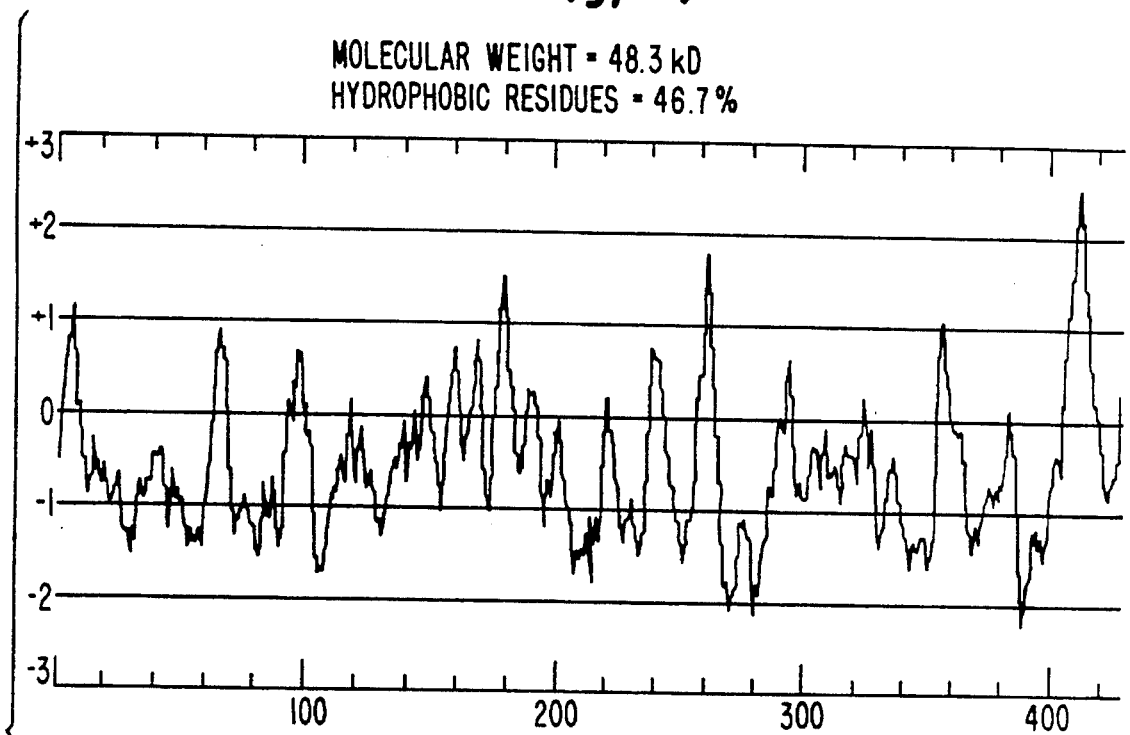

```
M L I Q M S E Q A R V R W H N A L I E L T L L T G V G Y N L
L L A L I N A N V F T V R P V I T Y A V E F L V Y Y A A C F L
L G L G S M S R Q R I A M I F G G L G L I V T L M F V R F L
V N W Q I D P K F F R D A L V V F A F V V L G S A Y T G S L
P K L F I R M T I I V S L V A A F E L A M P S A Y G D L V N
P K S F F V N A R G M S A E G F W N E D S N L F V S A T R P
G E R N F L P G S N L P R A S S W F I E P V T M G N Y I C F
F T A I V L T F W R W M R P S M L I L S I G L I G F M I V A
S D G R L A A G T C V L M V L L S P L L K R M D Q R L A F L
L F L F V I A S A W L L V W M T G I T A Y Q D T T M G R I F
F T V N S M N N L S F E S W M G L D F A Q A Y R Y F D S G I
S Y F I A S Q S I V G V L A F L L S Y S F L L L M P S K E G
Q L F K N Q A M F A F A L S L L V S N G Y F S I K T S A L W
W F V C G C M W H L M P A A S A V P V R D E S K E D P T D N
G V H V P L P A G A P R
```

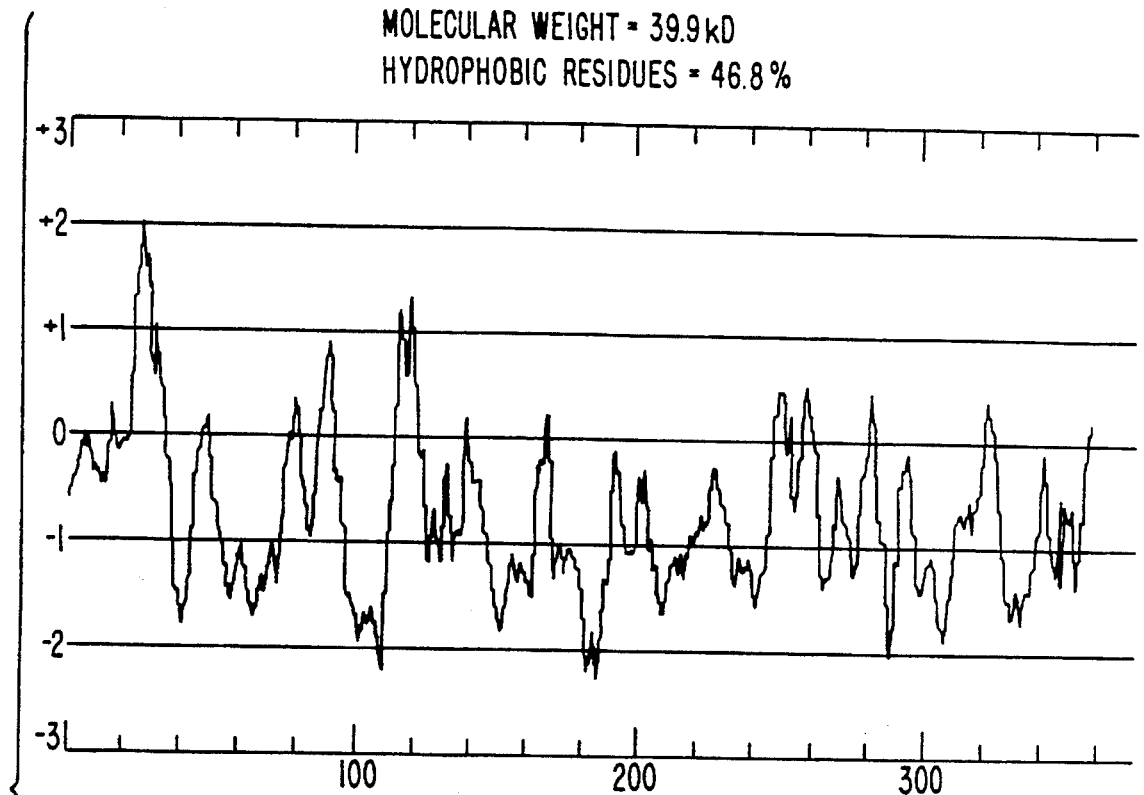

FIG. 12F(gpF)

MOLECULAR WEIGHT = 39.9 kD
HYDROPHOBIC RESIDUES = 46.8%

```
V N T V T G A S G T S A P V Q A A G A R A F A S G R S R D P
R I D A T K A I A I L L V V F C H A K G V P H G M T L F A Y
S F H V P L F F L V S G W L A A G Y A S R T T S L L Q T I T
K Q A R G L L L P Y V V F Y L L G Y V Y W L L T R N I G E K
A A R W G S H P W W E P I V S M F T G V G P D L Y V Q P P L
W F L P V M L V T V I G Y V L L R R W M P P L V I A A V A V
V L A W F W M N W F P L Q H M R L F W G L D V L P V S L C F
Y A L G A L L I H V S P Y L P T S L P G S A L V T V V L A A
L V A W L A G V N G R I D V N M L E F G R Q H A V F L L S A
V A G S L M V I C A A R M V Q E W T W L Q W I G R N T L L I
L C T H M L V F F V L S G V A A L A G G F G G A R P G L G W
A I F V T L F A L V A S V P L R W F L M R F A P W T L G A R
P V S A
```

FIG. 12G(gpG)
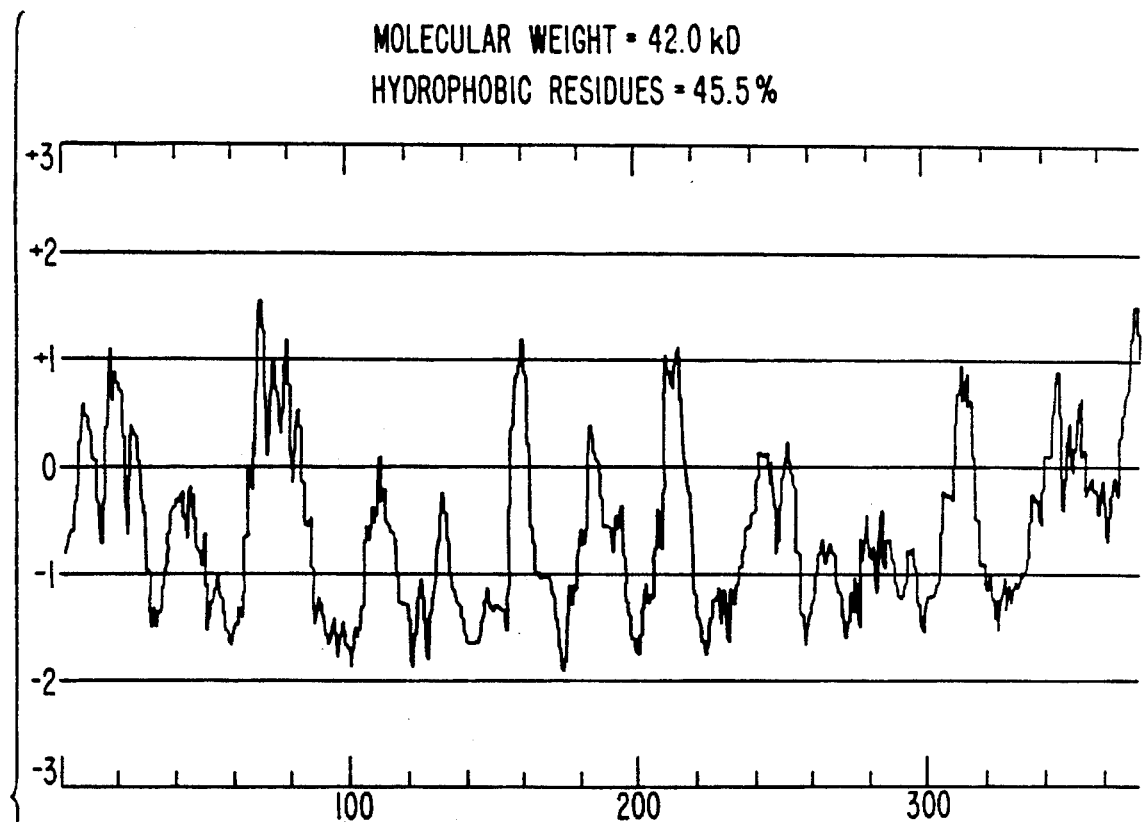

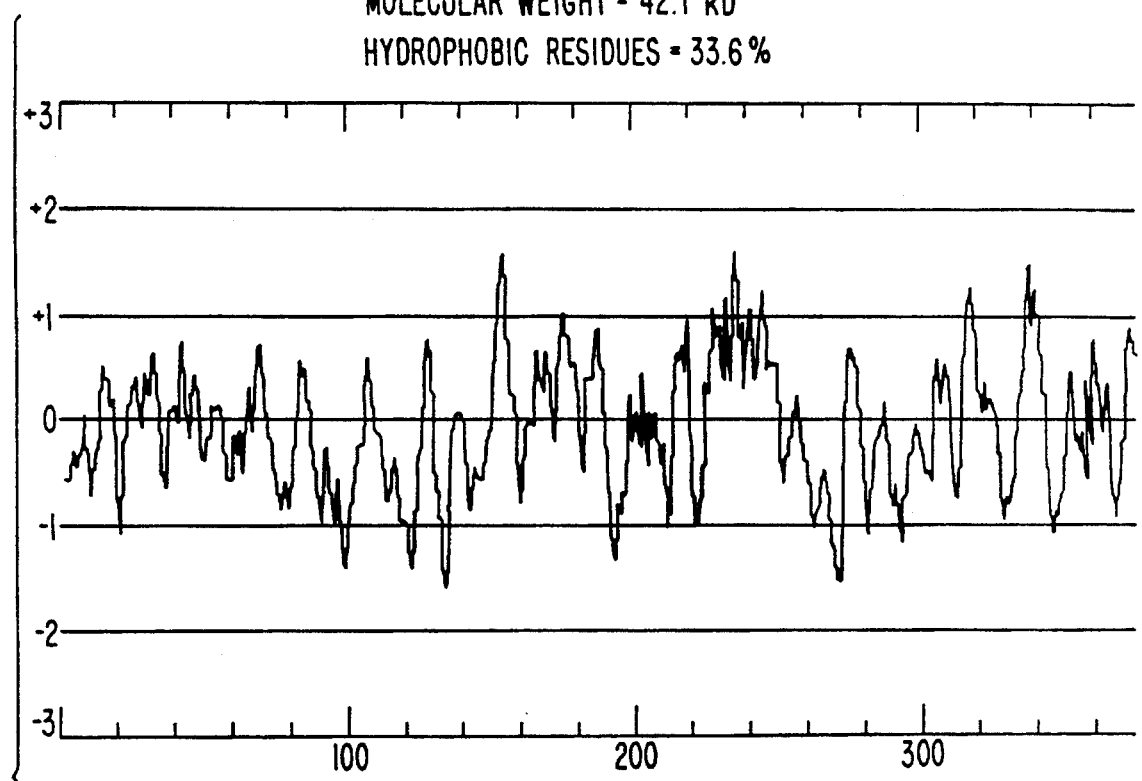

FIG. 12H(gpH)

MOLECULAR WEIGHT = 42.1 kD
HYDROPHOBIC RESIDUES = 33.6%

```
M K V V H V V R Q F H P S I G G M E E V V L N V A R Q H Q A
N S A D T V E I V T L D R V F T D P S A Q L A Q H E V H Q G
L S I T R I G Y R G S S R Y P I A P S V L G A I R S A D V V
H L H G I D F F Y D Y L A L T K P L H G K P M V V S T H G G
F F H T A Y A S R M K Q I W F Q T L T R T S A L A Y A R V I
A T S E N D G D L F A K V V A P S R L R V I E N G V D V E K
Y A G Q G A R A P G R T M L Y F G R W S V N K G L I E T L E
L L Q A A L T R D P Q W R L I I A G R E Y D L N E A D L R K
A I A E R G L Q D K V Q L S M S P S Q Q Q L C A L M Q Q A Q
F F V C L S R H E G F G I A A V E A M S A G L I P I L S D I
P P F V R L A T E S G Q G V I V N R D R I Q A A A D S V Q A
L A L Q A N A D F D A R R T A T M A Y V A R Y D W R H V V G
R Y I D E Y H A A L G T P R T Q E A V R
```

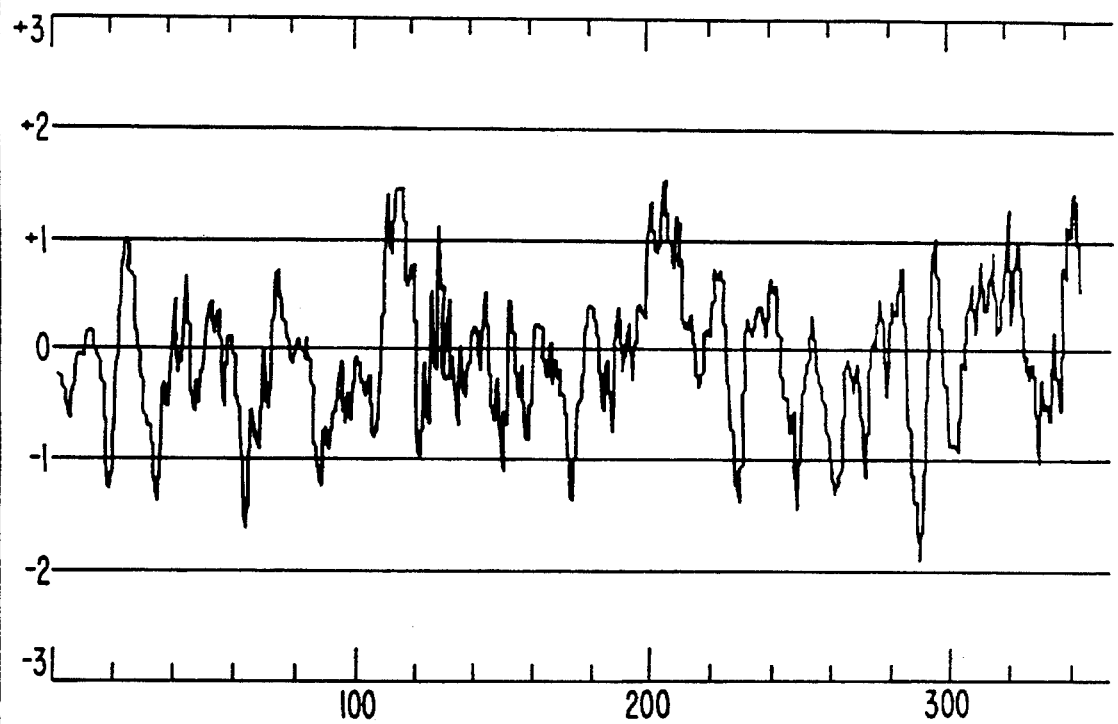

FIG. 121(gp1)

MOLECULAR WEIGHT = 38.9 kD
HYDROPHOBIC RESIDUES = 32.9%

```
M S A S A S L P V T R A A A A P R I T V L F S T E K P N A N
T N P Y L T Q L Y D A L P D A V Q P R F F S M R E A L L S R
Y D V L H L H W P E Y L L R H P S K M G T L A K Q A C A A L
L L M K L Q L T G T P V V R T L H N L A P H E D R G W R E R
A L L R W I D Q L T R R W I R I N A T T P V R P P F T D T I
L H G H Y R D W F A T M E Q S T T L P G R L L H F G L I R P
Y K G V E V L L D V M R G C A G P A P E P A H R R Q P G D A
R M R T L V E T A C Q D A R I S A L L A Y V E E P V L A R
E V S A C E L V V L P Y K Q M H N S G T L L L A L S L A R P
V L A P W S E S N A A I A D E V G P G W V F L Y E G E F D A
A L L S G M L D Q V R A A P R G P A P D L S Q R D W P R I G
Q L H Y R T Y L E A L G K D G D A A L
```

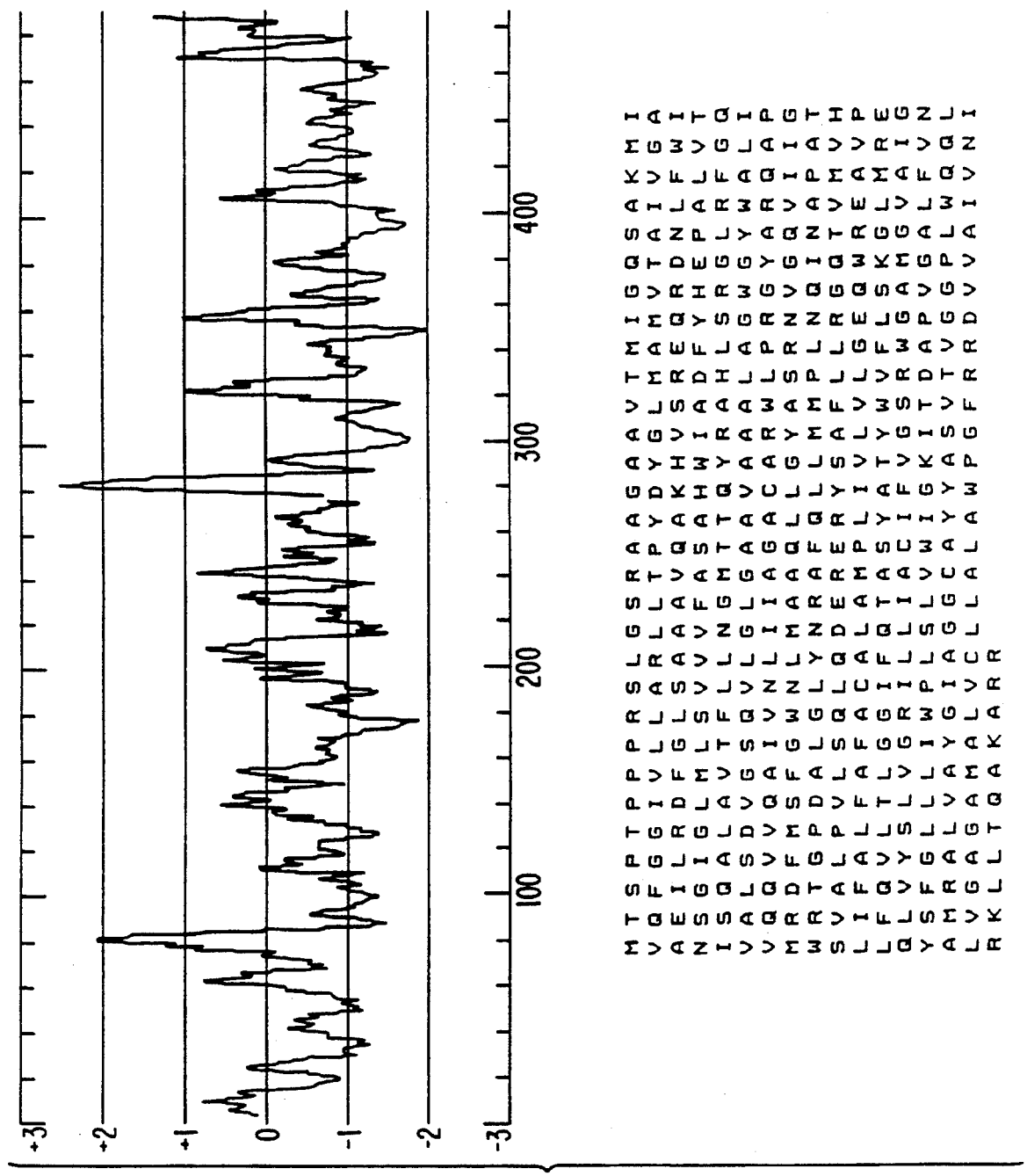
FIG. 12J(gpJ)
MOLECULAR WEIGHT=52.9 kD
HYDROPHOBIC RESIDUES=43.1%

FIG. 12K(gpK)

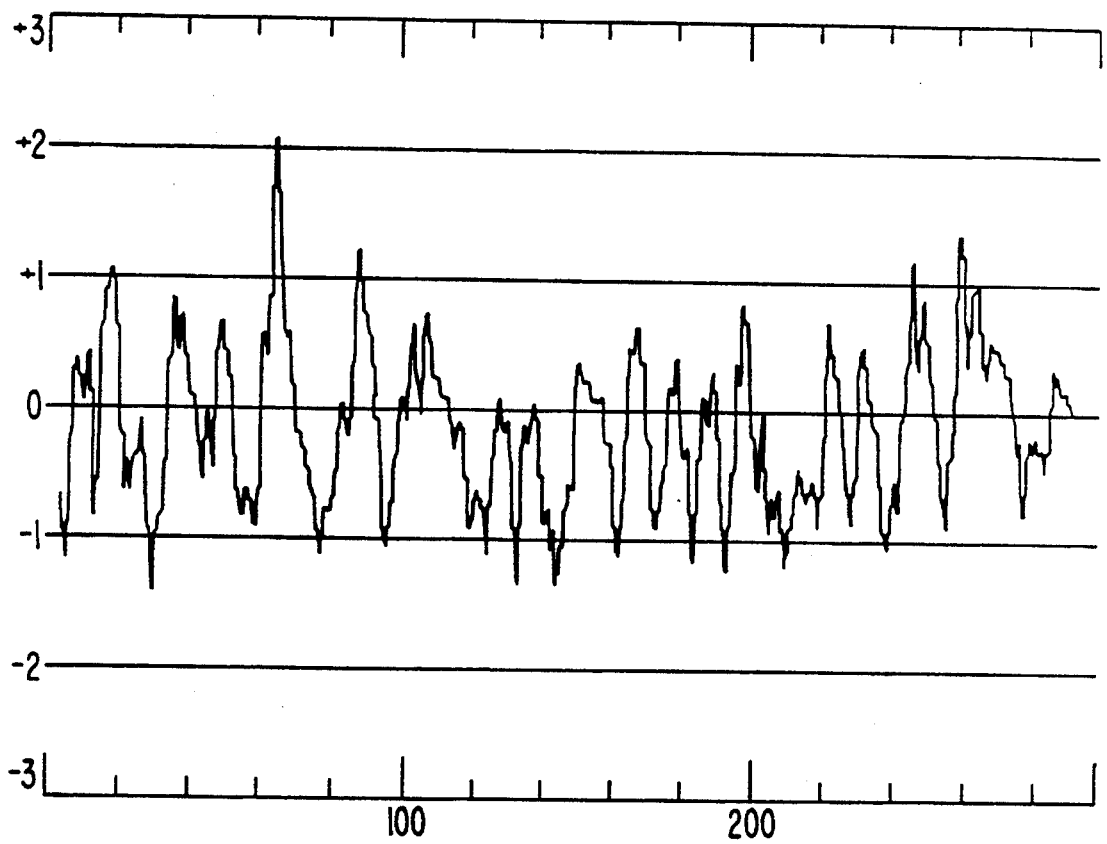

MOLECULAR WEIGHT = 32.4 kD
HYDROPHOBIC RESIDUES = 34.5%

```
M F R W Y A A H P F K Q L L D W M R E S D V I V F E S G I A
V A F I E L A K R V N P A A K L V Y R A S D G L S T I N V A
S Y I E R E F D R V A P T L D V I A L V S P A M A A E V A S
R D N V F H V G H G V D H N L D Q L G D P S P Y A E G I H A
V A V G S M L F D P E F F V V A S K A F P Q V T F H V I G S
G M G R H P G Y G D N V I V Y G E M K H A G T I G Y I K H A
R F G I A P Y A S E Q V P V Y L A D S S M K L L Q Y D F F G
L P A V C F N A V V G F Y K S R F G Y T P G N A D S V I A A
I T Q A L E A F F V R Y R Q C L N W S D T T D R V L D P R A
Y P E T R L Y F H F F T A A P Q L S S E A A L S H
```

FIG. 12L (gpL)

MOLECULAR WEIGHT = 29.3 kD
HYDROPHOBIC RESIDUES = 35.5%

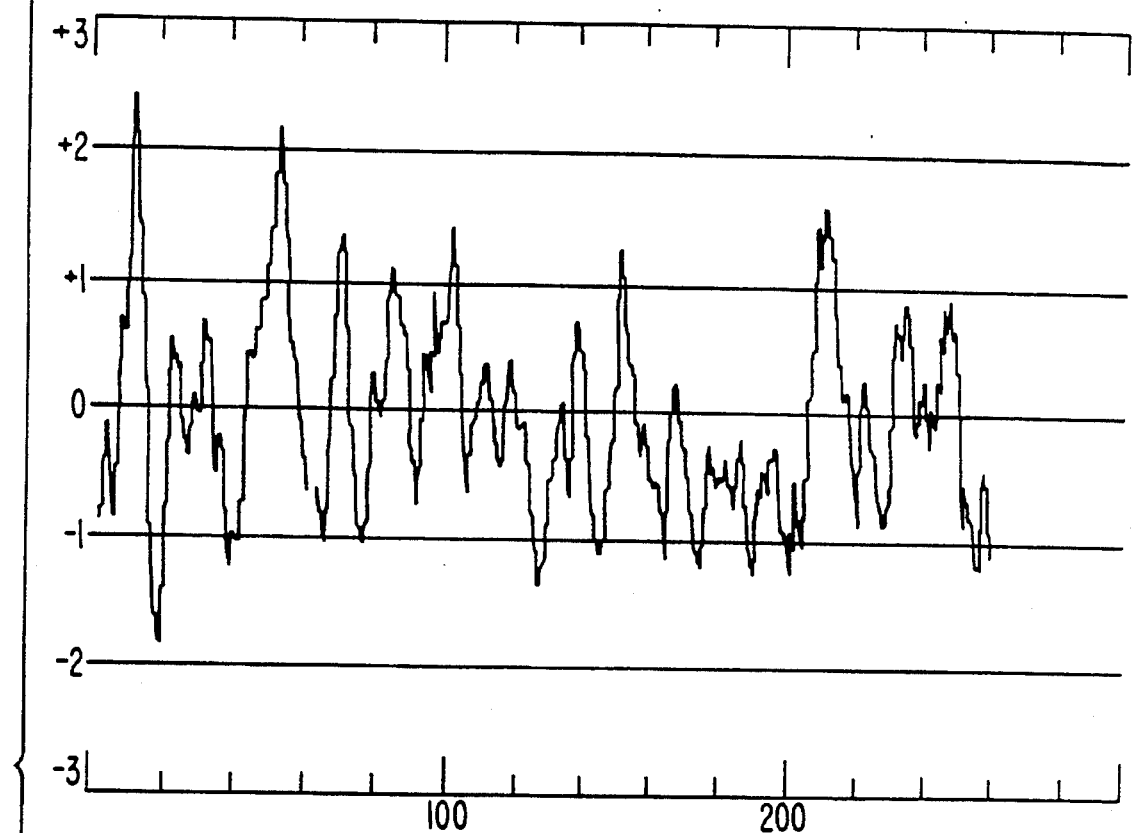

```
M A N A L L Q K W V E R A E R R A L F W W Q P K N G G V N M
G D H L S K V I V S C V L A L Q D K T L L E K R D L R Q K L
I A T G S V L H F A K D G D T V W G S G I N G K I P A E R N
T F S T L D V R A V R G P K T R A F L L E R G I A V P E V Y
G D P G L L T F M F F P A D A L G P V T K R F F A I V P H F
N E P V E K Y S A Y A E H L V F P N V K P A T F M S A L L S
A E F V I S S S L H G L I L A E A Y G I F A V Y L D W G N S
E D R F K Y D D Y Y H G T G R M Q W H A G H S V E E C M E L
G G N G S F D L E R L Q A G L L A A F P Y D L W
```

FIG. 12M(gpM)

MOLECULAR WEIGHT = 28.6 KD
HYDROPHOBIC RESIDUES = 34.5%

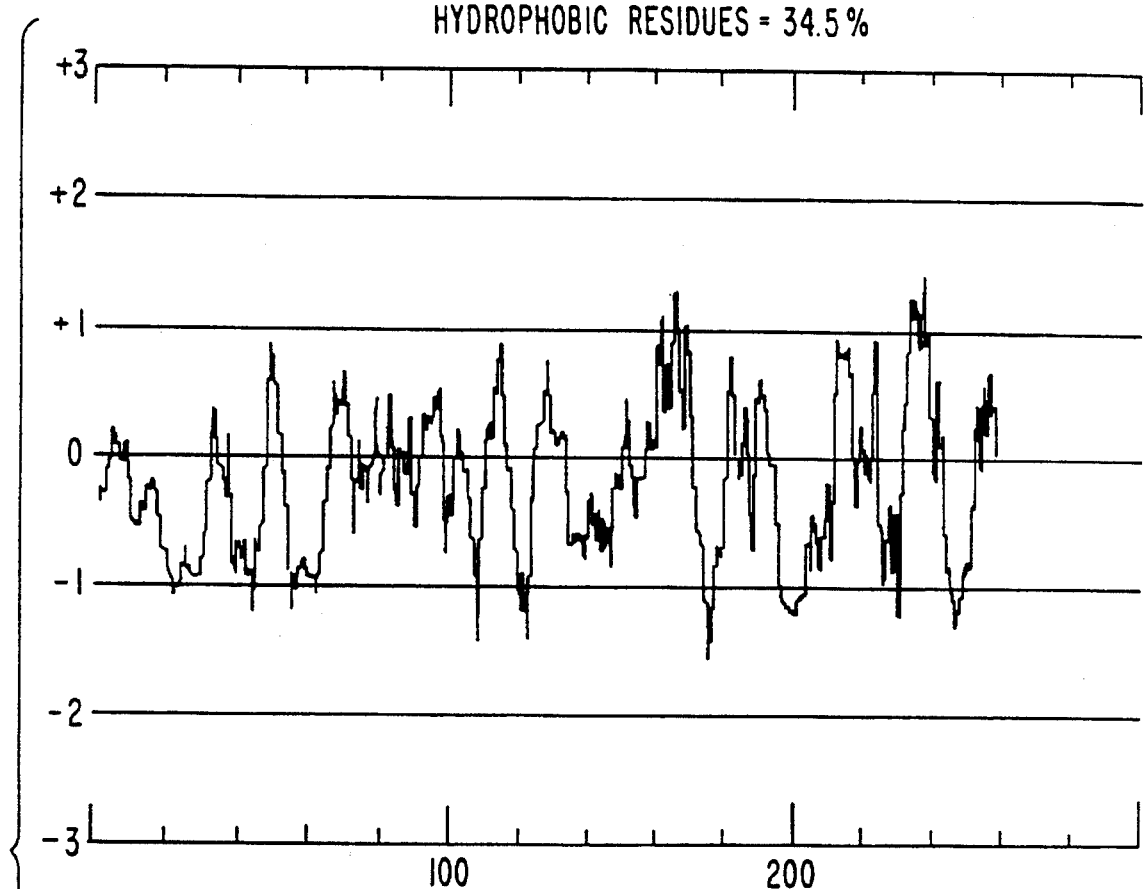

```
M H G Q F A G V E T A T V S A A T P A Q G V V I P L G G F F
V L S T T Q E A F A L D L F H A L A A H Q P R R V F F A N T
N F I V Q C Q A L R A R M Q A P A V R I V N D G I G M D L A
A R L I H G R R F A S N L N G T D L I P Y L C R E A A Q P L
K F F L L G G R P G V G K T A A A T L T G T L G Q Q V V G M
C D G Y G E F A A A G E G L A E R I N R S G A D V L L V A F
G N F L Q E R W I L D H S E A L Q V P L V F G V G A L L D F
L S G T A K R A P N W V R R L H M E W M Y R L L N E P R R L
L K R Y S W D L L V F F R T C L R A G K Q L A
```

TRANSCRIPTION TERMINATORS

SECONDARY CLOVERLEAF STRUCTURE FOR THE PROLINE tRNa IN THE 1.4 Kb BamHI FRAGMENT (POSITION 732)

RECOMBINANT-DNA MEDIATED PRODUCTION OF XANTHAN GUM

This application is a continuation of application Ser. No. 07/815,615, filed Jan. 7, 1992, now abandoned, which is a continuation of application Ser. No. 07/333,868, filed Apr. 3, 1989, now abandoned, which is a continuation of application Ser. No. 07/188,687, filed Apr. 27, 1988, now abandoned, which is a continuation of application Ser. No. 07/029,530, filed Mar. 23, 1987, now abandoned, which is a continuation-in-part of application Ser. No. 06,844,332, filed Mar. 26, 1986, now abandoned.

Xanthan gum is produced naturally by bacteria of the genus Xanthomonas, in particular by microorganisms of the species *X. campestris*. Xanthan gum is widely used in a variety of applications due to its unusual physical properties, i.e., its extremely high specific viscosity and its pseudoplasticity. In two specific applications, xanthan gum is used in foods as a thickening agent and in enhanced oil recovery as a mobility control and profile modification agent. In addition, xanthan gum is useful in the formulation of petroleum drilling fluids.

Chemically, xanthan gum is an anionic heteropolysaccharide. The repeating unit of the polymer is a pentamer composed of five sugar moieties, specifically two glucose, one glucuronic acid, and two mannose moieties. The sugar residues are arranged such that the glucose moieties form the backbone of the polymer chain, with side chains of mannose-glucuronic acid-mannose residues generally extending from alternate glucose moieties. Usually, this basic structure is specifically acetylated and pyruvylated as described, for example, by Janson, E. P. et al., in Carbohydrate Research 45:275–282 (1975), specifically incorporated herein by reference. The structure of xanthan gum is depicted viscosity of the fermentation broth, thus reducing the oxygen transfer rate, and necessitating the use of expensive aeration, cooling and agitation equipment to achieve desired product concentrations.

The present inventors have discovered portable DNA sequences encoding a gene cluster required for xanthan production and have cloned, on plasmid vectors, these portable sequences. When used in an appropriate host, particularly a denitrifying bacterium, these plasmid vectors will cause the production of xanthan gum according to the method of the present invention in an economical and commercially feasible manner. This technology could also be employed to produce variants of xanthan gum. Such variant polysaccharides are known to be produced by mutant strains of *X. campestris* that contain mutations within the chromosomal copy of the gene cluster responsible for xanthan production. Examples of these variant gums are disclosed in U.S. patent application Ser. No. 762,878 of Vanderslice et al. entitled "A Polysaccharide Polymer Made by Xanthomonas," filed Aug. 6, 1985 and U.S. patent application Ser. No. 844,435 of Doherty et al. entitled "Family of Xanthan-Based Polysaccharide Polymers Including Non-Actylated and/or Non-Pyruvylated Gum and Acetylated and Non-Acetylated Polytetramer Gum," filed Mar. 26, 1986. Both of these patent applications are specifically incorporated herein by reference. Cloning a portable DNA sequence that contains such a mutation onto a plasmid vector and subsequent transfer of that recombinant plasmid into an appropriate bacterium will result in synthesis by that bacterium of a polysaccharide equivalent to the particular xanthan gum variant polysaccharide produced by the mutated *X. campestris* strain carrying that mutation in its chromosome.

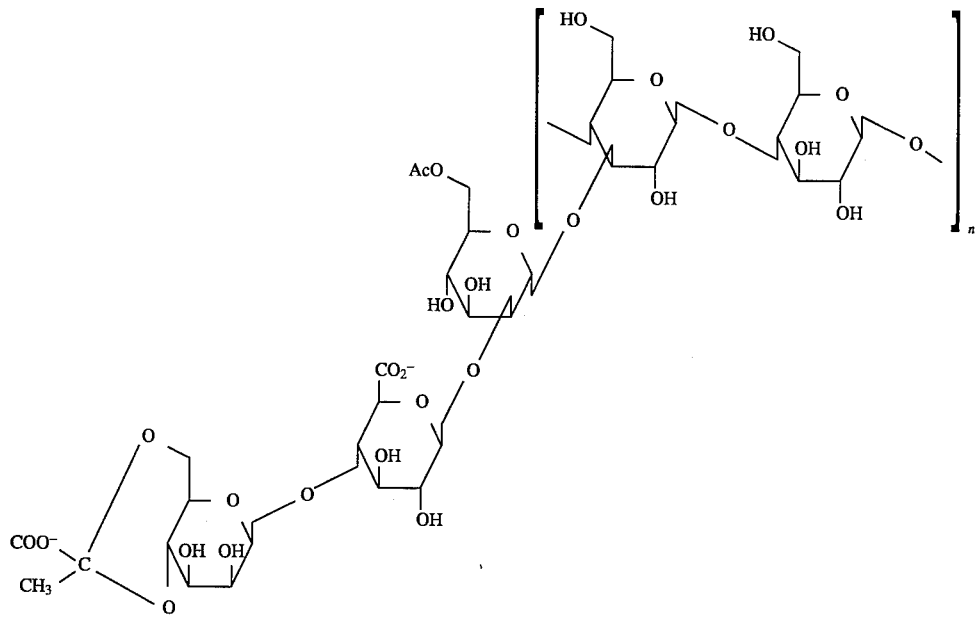

To date, *Xanthomonas campestris* and related Xanthomonas species have been the sole source available for the production of xanthan gum. However, these organisms have low temperature optima (27°–30° C.), slow growth rates and are obligate aerobes, all of which increase the cost of fermentation. Xanthan production drastically increases the

SUMMARY OF THE INVENTION

One object of the present invention is to provide a method for the production of xanthan gum in which the fermentation may be conducted at a temperature greater than 30° C. and/or which may be conducted under anaerobic conditions. An additional object of the present invention is to provide a recombinant-DNA mediated method for the production of xanthan gum using microorganisms which are capable of polysaccharide production and which are preferably capable of growth at or above 30° C. and/or under anaerobic conditions. The xanthan gums produced by this method are chemically equivalent to that produced by *Xanthomonas campestris*. Additional polysaccharides, created by mutations in various biosynthetic genes, can also be produced in alternative hosts.

To facilitate the recombinant-DNA mediated synthesis of these polysaccharides, it is a further object of the present invention to provide portable DNA sequences capable of directing production of polysaccharides. It is also an object of the present invention to provide vectors containing these portable sequences. These vectors are capable of being used in recombinant systems to provide commercially useful quantities of xanthan gums and other polysaccharides.

Additional objects and advantages of the invention will be set forth in part in the description which follows, and in part will be obvious from the description or may be learned from practice of the invention. The objects and advantages may be realized and attained by means of the instrumentalities and combinations particularly pointed out in the appended claims.

To achieve the objects and in accordance with the purposes of the present invention, methods for the production of xanthan gum are set forth, which methods utilize microorganisms capable of polysaccharide production, preferably at or above 30° C. and/or under anaerobic conditions. The polysaccharides produced by these methods are in one embodiment chemically equivalent to those produced by *Xanthomonas campestris* and in another embodiment are chemically equivalent to the variant gums disclosed by Vanderslice et al., supra, and Doherty et al., supra.

The portable sequences may be either synthetic sequences or restriction fragments ("natural" DNA sequences). In a preferred embodiment, a portable DNA sequence is isolated from a *X. campestris* library and is capable, when transferred into an alternative host, of directing the production of a xanthan gum which is chemically equivalent to that produced by *Xanthomonas campestris*.

Additionally, to achieve the objects and in accordance with the purposes of the present invention, a recombinant-DNA method is disclosed which results in microbial manufacture of xanthan gum and other polysaccharides using the portable DNA sequences referred to above. This recombinant DNA method comprises:

a) preparation of a portable DNA sequence capable of directing an alternate host microorganism to produce either a polysaccharide chemically equivalent to a polysaccharide produced by *X. campestris* or a novel polysaccharide structurally related to xanthan;

b) cloning the portable DNA sequence into a vector capable of being transferred into and replicating in a host microorganism, such vector containing elements for the expression of the gum biosynthetic enzymes encoded by the portable DNA sequence;

c) transferring the vector containing the portable DNA sequence into a host microorganism capable of producing polysaccharide under the direction of the portable DNA sequence, preferably at high synthetic rates, elevated temperature, and/or under anaerobic conditions;

d) culturing the host microorganism under conditions appropriate for maintenance of the vector and synthesis of the polysaccharide; and e) harvesting the polysaccharide.

In a preferred embodiment of the present invention, the portable DNA sequence is comprised of DNA sequences capable of directing production of the following enzymes: Transferase I; Transferase II; Transferase III; Transferase IV; Transferase V; Acetylase; Ketalase; and Polymerase. These enzymes, which are used in xanthan gum biosynthesis, are depicted in FIG. 1 and described more fully below.

To further accomplish the objects and in further accord with the purposes of the present invention, a series of cloning vectors are provided, each of which contains at least one of the portable DNA sequences discussed above. In particular, plasmids pRK290-H336 and pX209 are disclosed.

Strains *E. coli* LE392(TX209), bearing plasmid pX209, and strain *E. coli* LE392(pRK290-H366), bearing plasmid pRK290-H366, have been deposited in the American Type Culture Collection, Rockville, Md., on Mar. 21, 1986 under Accession Nos. 67051 and 67049, respectively.

It is to be understood that both the foregoing general description and the following detailed description are exemplary and explanatory only and are not restrictive of the invention, as claimed. The accompanying drawings, which are incorporated in and constitute a part of this specification, illustrate various embodiments of the invention and, together with the description, serve to explain the principles of the invention.

BRIEF DESCRIPTION OF THE DRAWINGS

FIG. 2 is a restriction map of lambda 655(+).

FIG. 3 is a restriction map of lambda 708(+).

FIG. 10 consists of the nucleotide sequence of a 16,080 base pair segment of *Xanthomonas campestris* DNA that contains a gene cluster that directs Xanthan biosynthesis.

FIG. 11 shows an overview of the organization and structure of the genes contained in the 16 kb segment of DNA. The top line in the figure is a BamHI restriction map and indicates the location of each of the BamHI restriction sites in the sequence. The line drawn above the frame analysis curves shows the approximate position of some of the mutations that have been isolated and characterized. The frame analysis curves presented show the distribution of G+C content at the first (blue line), second (red line), and third (black line) nucleotide positions. Note that the distribution of G+C content at the three nucleotide positions is non-random throughout the entire sequence, indicating that virtually all of this DNA codes for protein products. The reading frame of each protein is defined by the nucleotide position having an intermediate value within each region of non-random G+C distribution. The points where the G+C distribution at the three nucleotide positions change predict either the beginning or end of a gene or the end of one gene and the beginning of the next. In each case, these points were found to correlate with the presence of either a start or stop codon in the appropriate reading frame.

Below the frame analysis curves, separate arrows are drawn to indicate the location and extent of each gene in the sequence. For convenience, we designate each gene with a letter and use that letter preceded by "gp" to designate its protein product. Above each arrow, the molecular weight of the protein product is shown in kD. Below each arrow, the name of each gene product is shown as its lettered name as well as its functional name for those cases where gene function could be derived from the mutant phenotype.

FIGS. 12A–12M show data relating to hydrophilic amino acid residues and predicted amino acid sequences with respect to gpA-gpM.

FIG. 13 shows potential secondary structures of putative transcription terminators identified within the DNA sequence around positions 900, 3400 and 12,400.

FIG. 14 shows the folded secondary structure of the proline tRNA identified in the DNA sequence from positions 732–808.

FIG. 15*a* shows the locations of various TnK12 insertion mutations within the cloned *X. campestris* DNA carried in recombinant plasmid pRK290-H336.

FIG. 15*b* shows the extent of DNA deleted from the *X. campestris* chromosome in a series of deletion mutants. The deleted DNA is indicated by the cross-hatched box.

FIG. 16*a* shows the locations of in vitro generated $Kan^r$ insertion and deletion mutations within plasmid pRK290-HA3.

FIG. 16*b* shows the positions of seven in vitro generated $Kan^r$ insertion mutations within plasmid pRK290-H336.

DETAILED DESCRIPTION OF THE PREFERRED EMBODIMENTS

The present inventors believe that biosynthesis of xanthan gum in *Xanthomonas campestris* proceeds via the pathway depicted in FIG. 1. This figure depicts the assembly of the pentasaccharide (five-sugar) repeat unit of xanthan gum linked to an isoprenoid lipid "carrier" molecule. The assembly of this penta-saccharide is shown to proceed by sequential addition, in a specific and defined order, of the five individual sugar moieties that occur in the pentasaccharide repeat unit. Each unique sugar addition is catalyzed by a specific enzymatic activity that is specific to that particular step. The sugars are donated by specific sugar nucleotides. The enzymatic activities are referred to herein as "Transferases." The individual enzymatic activities are further designated by roman numerals I through V, denoting the step in the sequentially ordered series of sugar additions that each Transferase activity catalyzes.

The two mannose sugar moieties present in mature xanthan, and in the pentasaccharide precursor unit, are known to be modified. The mannose moiety added at step 3 by the activity of Transferase III is known to be acetylated. The fraction of this moiety present in the acetylated form in mature xanthan gum is observed to be variable. An enzymatic activity, here termed Acetylase, catalyzes the addition of the acetyl group to the mannose, although the precise point in the sequence of the biosynthetic pathway at which the Acetylase functions is currently unknown. Similarly, the mannose sugar moiety attached by the activity of Transferase V at step 5 is known to be pyruvylated. An enzymatic activity, here termed Ketalase, catalyzes the addition of the pyruvate group. Again, the fraction of these mannose moieties that are observed to be pyruvylated in mature xanthan gum is variable, and the point within the biosynthetic pathway at which the Ketalase acts is currently unknown.

Pentasaccharide precursor units are polymerized in a subsequent enzymatic reaction catalyzed by an activity referred to here as "Polymerase." The Polymerase activity catalyzes release of a pentasaccharide subunit from its attached isoprenoid lipid carrier molecule and concerted attachment of that pentasaccharide unit onto a lipid-linked pentasaccharide, decasaccharide, or higher order array of the basic pentasaccharide repeat with the resulting increase in the degree of polymerization of recipient nascent xanthan molecules.

As noted in the copending United States Patent Applications of Vanderslice et al. and Doherty et al., supra, both of which are specifically incorporated herein by reference, other polysaccharides have been discovered which may be described as "variants" of xanthan. These include the "polytrimer" of Vanderslice et al., both in its acetylated and non-acetylated forms, as well as the "polytetramer," both acetylated and non-acetylated, and the non-acetylated, non-pyuvylated, or non-acetylated and non-pyruvylated pentameric xanthan gums of Doherty et al. It is clear from both the foregoing description of the enzymes discovered in the xanthan pathway and from the following description of the newly-discovered mutant organisms that the materials necessary for the recombinant-DNA mediated production of these variant gums are inherently described herein. For example, polytetramer may be synthesized in a recombinant-DNA system which does not possess the DNA sequence encoding Transferase V while a non-acetylated polytetramer-synthesizing plasmid would lack both the genes encoding Transferase V and Acetylase.

Figure 1:
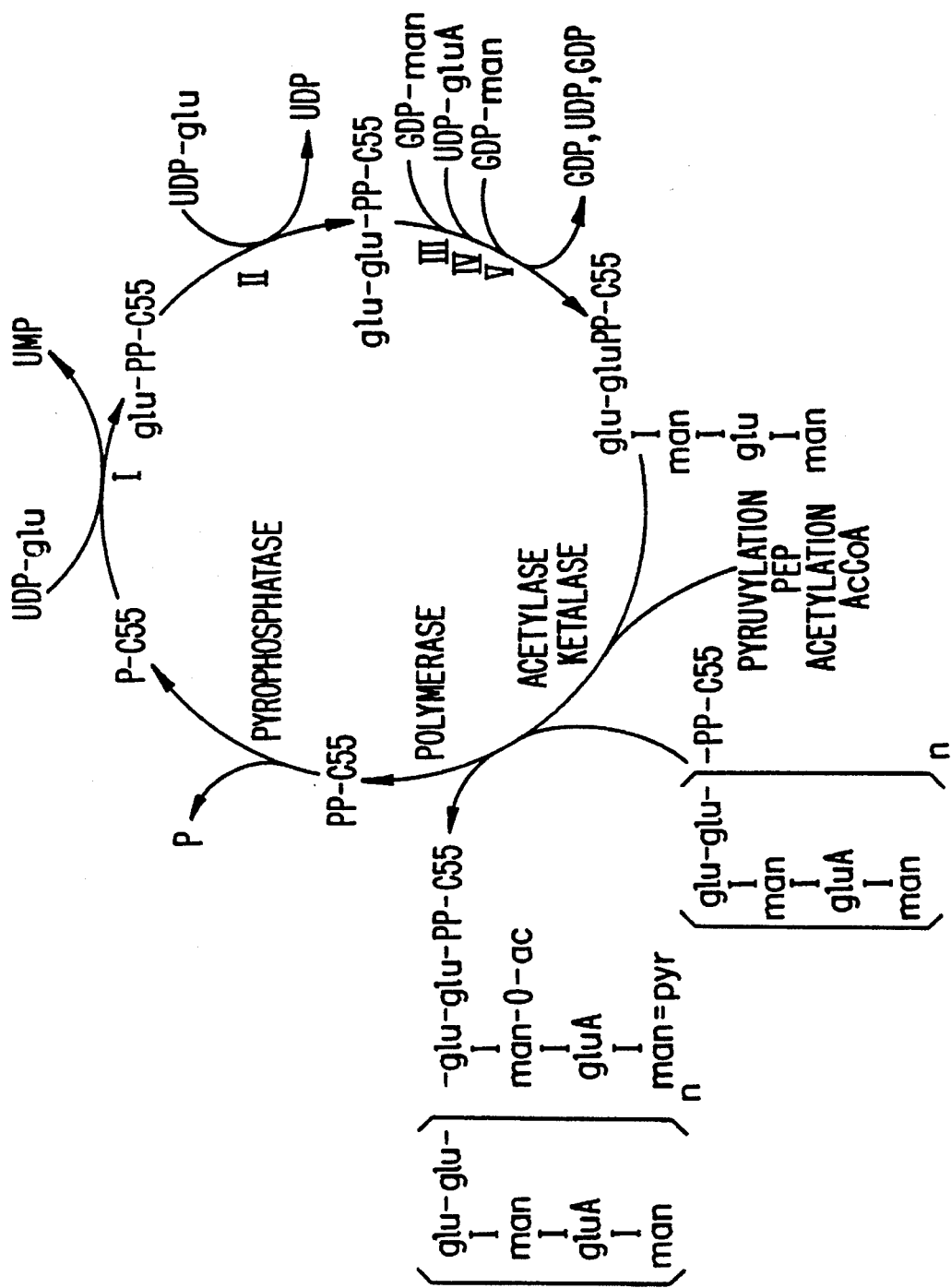
FIG. 1 depicts the biosynthetic pathway of xanthan gum synthesis in *X. campestris* (shown in FIG. 1 of U.S. Pat. No. 4,713,449, issued Dec. 15, 1987).

A mutation of *Xanthomonas campestris* has been identified that specifically inactivated the activity of Transferase IV. A strain carrying this mutation, X655, has been described by Vanderslice et al. and has been deposited at American Type Culture Collection (ATCC) in Rockville, Maryland under Accession No. 53195. The identification of that specific defect in that *X. campestris* mutant strain X655 led to the cloning of *X. campestris* chromosomal DNA sequences from the region of the chromosome to which the site of the mutation in-strain X655 was localized. Mutagenesis and analytical technology were used as described below in Examples 1, 2 and 7 to induce and analyze the phenotypic properties of mutations in DNA sequences near the site of the X655 mutation. As a basis for the present invention, it was believed that the genes encoding other Transferase activities would be clustered in the vicinity of the gene identified in strain X655 as encoding a necessary component of the activity of Transferase IV, because in bacteria clustering of genes for metabolic pathways is known to occur.

Knowledge of the Transferase IV defect in strain X655 was used to clone and genetically and physically analyze a large segment (35 kb) of *X. campestris* chromosomal DNA spanning the site of the mutation causing the Transferase IV defect in strain X655. Numerous mutations within that DNA were induced and characterized. Analyses of genetic locations of these mutations and the phenotypes of mutant strains carrying these mutations (Examples 2, 4 and 7) provided direct evidence that this DNA sequence in the *X. campestris* chromosome, and as a portable DNA segment on transferable plasmid vectors, contained genes encoding proteins required for the activities of Transferase I, II, III, and IV, Acetylase, and Ketalase. These data lead to the conclusion that the portable DNA segments cloned in plasmids pRK290-H336 and pX209 contain genes encoding proteins required for the activities of Transferases I through V, Acetylase, Ketalase, Polymerase, and possibly other as yet uncharacterized activities, necessary for, or related to, xanthan biosynthesis. Transfer of plasmid vectors containing this "gene cluster" for xanthan biosynthesis, as a portable DNA sequence, into bacteria other than *Xanthomonas campestris*, could thus be used to reduce the cost of production of xanthan gum by altering the conditions of the fermentation.

To date, *Xanthomonas campestris* and related Xanthomonas species have been the sole microbial source available for the production of xanthan gum. However, these organisms have low temperature optima (27°–30° C.), slow growth rates and are obligate aerobes, all of which increase the cost of fermentation. In addition, the existing aerobic fermentation technology requires a low viscosity fermentation broth to enable the broth to have a high oxygen transfer rate. However, because xanthan is an exopolysaccharide, the xanthan production drastically increases the viscosity of the fermentation broth, thus reducing the oxygen transfer rate and necessitating the use of expensive aeration, agitation, and cooling equipment to achieve desired product concentrations.

It has been proposed by the present inventors that denitrifying bacteria, which may have higher temperature optima and faster growth rates and will have the ability to grow anaerobically if supplied with a suitable nitrogen source, could be transformed with portable DNA sequences capable of directing the production of xanthan gum. Production of xanthan in these organisms will be less expensive than in the current species which is employed. In addition, the present inventors have discovered a portable DNA sequence encoding the gene cluster responsible for xanthan production and have plasmid vectors which contain these portable sequences. When used in an appropriate host, particularly a denitrifying bacterium, these plasmids will cause the production of xanthan gum according to the method of The present invention in an economical and commercially feasible manner. In addition, bacterial hosts with only some of the proposed advantages are contemplated as alternative production hosts.

The genes responsible for conversion of xanthan precursors (UDP-glucose, UDP-glucuronic acid, GDP-mannose, acetyl-CoA, and phosphoenolpyruvate) to xanthan are clustered in the *X. campestris* genome and have been cloned. In the present invention, these genes will be introduced into suitable alternative hosts, and gum biosynthesis measured. Corrective steps are outlined in the eventuality that the alternative hosts, with the biosynthetic cluster present, do not synthesize xanthan gum.

Additional embodiments of the present invention are envisioned as employing other known or currently undiscovered vectors which would contain one or more of the portable DNA sequences described herein. In particular, it is preferred that these vectors have some or all of the following characteristics: (1) be stable in the desired host; (2) be capable of being present in an appropriate copy number in the desired host; (3) possess a regulatable promoter; and (4) have at least one DNA sequence coding for a selectable trait present on a portion of the plasmid separate from that where the portable DNA sequence will be inserted.

The following, non-inclusive list of bacterial hosts and plasmid vectors is believed to set forth combinations which can easily be altered to meet the above-criteria and are therefore preferred for use in the present invention (Table 1). Such alterations are easily performed by those of ordinary skill in the art in light of the available literature and the teachings contained herein.

TABLE I

| HOST VECTORS | COMMENTS | |
|---|---|---|
| PSEUDOMONAS | RSF1010 | Some vectors useful in |
| *P. AERUGINOSA* | Rms149 | broad host range of Gram- |
| *P. PUTIDA* | pKT209 | negative bacteria including |
| | RK2 | Xanthamonas |
| | pSa727 | and Agrobacterium. |
| CLOSTRIDIUM | pJU12 | Shuttle plasmids for *E. coli* |
| | | and |
| *C. PERFRINGENS* | pJU7 | *C. perfringens* construction, |
| | | ref. |
| | pJU10 | Squires, C. et al. (1984) |
| | | Journal |
| | pJU16 | Bacteriol. 159:465–471. |
| | pJU13 | |

The large cluster of gum biosynthetic genes has been cloned on a plasmid containing a broad host range origin of DNA replication that can be transferred and maintained in a wide variety of gram-negative bacterial species, including *E. campestris* and *X. campestris* strain X1107, which contains a deletion of all the known gum biosynthetic genes. Plasmid pRK290-H336 converts X1107 into a xanthan producing strain through complementation.

When a plasmid such as pRK290-H336 is placed in an alternative host, many steps must occur properly in order for xanthan biosynthesis to occur. First, the genes encoding the biosynthetic enzymes must be transcribed and translated to give functional biosynthetic enzymes at an appropriate level.

Second, the alternative hosts must contain sufficient biosynthetic capacities for acetyl-CoA, phosphoenolpyruvate, UDP-glucose, UDP- glucuronic acid, and GDP-mannose so that the biosynthetic enzymes can polymerize those precursors into xanthan gum. Third, the biosynthetic enzymes encoded by the cluster must aggregate if such a multiprotein complex is the operative biosynthetic unit. Fourth, the architecture of that complex (or the individual enzymes) must provide vectorial polysaccharide biosynthesis so that the xanthan will be secreted into the culture medium.

The practice of genetics, molecular biology, biochemistry, fermentation engineering, microbial physiology, and recombinant DNA technology, by one skilled in the art, makes likely the straightforward and obvious isolation of alternative hosts that express the xanthan biosynthetic genes and that can produce extracellular xanthan gum.

EXAMPLES

Example 1

This example shows the methods of mutagenesis and screening employed to generate the mutant strains which are xanthan gum deficient.

B1459 S4-L was obtained from the Northern Regional Research Laboratories of the U.S. Department of Agriculture. It was genetically marked with a chromosomal resistance to streptomycin and was used as a recipient in a conjugation with *E. Coli* LE392 containing plasmid pRK2013::Tn10. Plasmid pRK2013 contains Tn903 which encodes kanamycin resistance as described by Figurski, D. H., and Helinski, D. R. in Proc. Natl. Acad. Sci., U.S.A., 76:1648–1652 (1979), specifically incorporated herein by reference. The plasmid cannot replicate in *X. campestris*. Transposon Tn10 encodes resistance to tetracycline. Transconjugants were selected which were resistant to streptomycin and kanamycin, or streptomycin and tetracycline. The former occurred at a frequency of about $4 \times 10^{-6}$ per recipient and presumably resulted from a transposition of Tn903. The latter occurred at a frequency of about $3 \times 10^{-6}$ per recipient and presumably resulted from a transposition of Tn10 into the genome of *Xanthomonas campestris*.

Auxotrophs were found among these transconjugants at a frequency of about 2%; their needs were widely distributed among the various nutritional requirements. This indicates that these transposons do not have a particularly preferred locus for insertion in *X. campestris*. Prototrophic revertants of the auxotrophs were selected, and most were found to be drug-sensitive; this suggests that the auxotrophies were caused by transposon insertion.

To screen for xanthan gum deficient mutants among the doubly resistant transconjugants, Congo Red dye (200 ug/ml), which enhances the morphological distinction between xanthan gum producing and non-producing colonies, was added to the solid media. Colonial morphology was examined after 7 to 12 days incubation at 30° C. Xanthan gum deficient mutants were found at a frequency of approximately $10^{-4}$. Henceforth strains that fail to make xanthan in vivo are termed Gum⁻ strains, and those caused by insertion of Tn10, also Gum⁻ strains, may be additionally designated as gum::Tn10 mutants.

Example 2

This example demonstrates the biochemical phenotypes of the Gum⁻ mutant strains and the methods used to assess the phenotypes.

The basic method relating to the use of a cell-free system to study the biosynthetic pathway of xanthan gum is described by Ielpi, L., Couso, R. O., and Dankert, M. A. in FEBS Letters 130:253–256 (1981), specifically incorporated herein by reference. It has been found that a modified version of this method may be employed to analyze the Gum⁻ isolates described herein. For this novel method, the in vitro cell-free system is prepared generally by lysing cells of a microorganism, preferably *Xanthomonas campestris*, in the presence of a suitable buffer, preferably with EDTA, and obtaining the appropriate biosynthetic enzymes which are able to subsequently process exogenously added substrates. Alternate means of lysis may be used, including but not limited to sonication, detergent treatment, enzyme treatment and combinations thereof.

Generally, to determine the defective step in the biosynthetic pathway of a Gum⁻ mutant, a lysate of this microorganism was incubated with the appropriate substrates, which may include UDP-glucose, GDP-mannose, UDP-glucuronic acid, acetyl-CoA, and phosphoenolpyruvate. The choice of substrates is dependent on the steps which are desired to be analyzed. The biosynthetic process may, in one embodiment, be monitored by the incorporation of radiolabeled substrates into the polymeric units. Other methods that are known to those of ordinary skill in the art also may be used to allow identification of the biosynthetic intermediates. In particular, chromatographic methods have been developed to separate and to identify the oligosaccharide intermediates after hydrolysis from the lipid carriers. These include thin layer chromatography (TLC) and high performance liquid chromatography (HPLC).

The cell-free biosynthesis of xanthan has been found to be a time-dependent, sequential process that is dependent on the addition of all three specific sugar nucleotides. The background of non-specific incorporation of labeled substrate is minimal and does not interfere with the detection of the xanthan-specific intermediates or xanthan polymer in the gum fraction.

The involvement of lipid carriers, specifically C55 isoprenoid pyrophosphate, has been shown in several polysaccharide biosynthetic pathways. Additionally, the involvement of a pyrophosphoryl-linked lipid carrier in xanthan biosynthesis has been demonstrated and confirmed. Thus, the xanthan biosynthetic intermediates, at least up to the pentasaccharide, have been found to be recoverable in the organic soluble fraction with these carrier lipids.

Using methods described herein for recovery of intermediate products, it has been discovered that, under in vitro conditions, mutant *X. campestris* lysates will produce accumulated intermediates and novel truncated forms of xanthan gum, even in the presence of all substrates required for normal xanthan biosynthesis. The specific blockage points indicate which particular enzyme activities are missing. Gum⁻ strains were analyzed and assigned biochemical phenotypes. These biochemical phenotypes allow the genotypes of the mutant strains to be defined. For instance, a mutant strain that accumulates cellobiose on the lipid carrier in vitro is said to have a defect in the gene for Transferase III.

If the lysate of a Gum⁻ mutant produces normal xanthan gum when supplied with all the substrates, one concludes that all of the enzymes in the biosynthetic pathway are normal. Thus, the inability to make gum in vivo is a result of the absence of one of the required substrates. A class of Gum⁻ mutants which can make gum only in vitro when the substrates are provided was found. These Gum⁻ mutants are discussed more fully in U.S. patent application Ser. No.

843,349 of Betlach et al. entitled "Process for the Synthesis of Sugar Nucleotides Using Recombinant-DNA Methods," filed Mar. 24, 1986. All of these mutants mapped away from the gum cluster.

Specific procedures for these cell-free studies are described herein. The Gum⁻ derivatives were grown in YM (yeast-malt medium) supplemented with 2% (w/v) glucose as described by Jeanes, A., et al. (U.S. Department of Agriculture, ARS-NC-51, 14 pp (1976)) specifically incorporated here by reference. Cult. res were grown to late log phase at 30° C. at 300 rpm. The cells were titered on YM plus 2% (w/v) glucose plates at 30° C. The cells were harvested by centrifugation and washed with cold Tris-HCl, 70 mM, pH 8.2. Washed cells were resuspended in Tris-HCl, 70 mM, pH 8.2 with 10 mM EDTA and were freeze-thawed three times by a procedure similar to Garcia, R. C., et al. (European Journal of Biochemistry 43:93–105, (1974)) specifically incorporated herein by reference. This procedure ruptured the cells, as was evidenced by the increased viscosity of the suspensions and the complete loss of cell viability (one in $10^6$ survivors) after this treatment. The freeze-thawed lysates were frozen in aliquots at −80° C. Protein concentration was determined with BIO RAD assay (BIO RAD Laboratories, Richmond, Calif.) and was found to be 5 to 7 mg cell protein per ml of lysate.

As described in Ielpi, L., Couso, R. O., and Dankeft, M. A., supra, an aliquot of freeze-thawed lysate (equivalent to 300 to 400 ug protein), DNAase I (10 ug/ml), and $MgCl_2$ (8 mM) were preincubated at 20° C. for twenty minutes. An equal volume of 70 mM Tris-HCl, pH 8.2, with the desired radiolabeled sugar nucleotides (UDP-glucose and GDP-mannose), with or without UDP-glucuronic acid, was added and incubated at 20° C. At various times, the reactions were stopped by the addition of EDTA to 4 mM. The samples were centrifuged; the pellets were washed two times with buffer. To allow analysis of the gum fractions, the supernatants were combined, carrier xanthan (100 ug) was added, and the xanthan plus synthesized polymer were precipitated with ethanol(60%)-KCl(0.8%). The precipitated polymer was resuspended in water and reprecipitated two more times to remove unincorporated label. Radioactivity incorporated into the gum fraction was determined in a liquid scintillation counter, and the data were processed to obtain incorporation in terms of picomoles.

To allow analysis of the lipid carrier linked intermediates, the washed pellet was extracted twice with chloroform:methanol:water (1:2:0.3). The lipid-linked biosynthetic intermediates were converted to the free oligosaccharides by mild acid hydrolysis (pH 2, 90° C., 20 min) and alkaline phosphatase treatment (bovine alkaline phosphatase, 50 mM $MgCl_2$, and 10 mM glycine buffer pH 9.8 at 37° C. overnight). The samples were back-extracted with chloroform:methanol (2:1) and centrifuged. The aqueous phase was removed and reduced in volume in vacuuo for analysis by thin-layer chromatography.

Thin-layer chromatography was carried out on silica gel (Baker 250 um, preformed lanes) with butanol:dioxane:water (35:50:20) using three developments. Compounds radiolabeled with carbon-14 were detected by autoradiography at −80° C. using Kodak X-Omat AR film with standard development. The sugar standards were visualized with aniline diphenylamine (1.8% aniline and 1.8% diphenylamine in acidified acetone obtained from Sigma Chemical Co.). The mobility of the xanthan biosynthetic intermediates was compared to the mobility of sugar standards. For radiometric analysis of double-labeled oligosaccharides, silica gel not treated with interfering sprays was scraped, eluted, and counted with Budget-Solve Aqueous Counting Cocktail (RPI) in plastic vials in a Beckman LS-7500 scintillation counter utilizing the autoquench compensation. The scintillation data were processed to obtain the absolute amounts of [$^3$H]-labeled and [$^{14}$C]-labeled materials to allow molar ratios of the sugars in the compounds to be computed.

The Gum⁻ strains analyzed in vitro were assayed in several ways: (1) radiolabeled UDP-glucose alone to assess the charging of the carrier lipid with glucose or cellobiose, (2) unlabeled UDP-glucuronic acid and double radiolabeled UDP-glucose and GDP-mannose to determine the molar ratio of glucose and mannose, and (3) unlabeled UDP-glucose and double radiolabeled GDP-mannose and UDP-glucuronic acid to compare the molar ratio of mannose and glucuronic acid in the intermediates and the gum fraction. Mutants suspected of defects in acetylation or pyruvylation were checked for their ability to incorporate radiolabeled acetyl-CoA and phosphoenolpyruvate by the methods of Ielpi et al., Biochem. Biophys. Res. Comm. 102:1400–1408 (1981) and Ielpi et al., Biochem. Intern. 6:323–333 (1983), both of which are specifically incorporated herein by reference.

The strains fell into two major phenotypes. One group was defective in gum synthesis in vivo and in vitro. All of these mutants had mutational insertions in the gum DNA cluster. The other group, although they could not synthesize polysaccharide in vivo, could synthesize xanthan gum in vitro when the substrates were provided. All of these mutants had mutational insertions in DNA unlinked to the gum cluster. These mutants were tested for the presence of the sugar nucleotides and found to be defective in various steps of the biosyntheses of sugar nucleotides.

The mutants with blocks in the gum biosynthetic pathway were found to be of several types. The possible biochemical phenotypes and our observations are presented here and in FIG. 7 where the map positions of some mutations conferring these particular phenotypes are shown.

Transferase I and Unknown Defects

Many mutant lysates showed poor incorporation of radiolabel in the organic fraction, with a small quantity of glucose being the only sugar detected above background. No polymeric material was detected in the gum fraction. This small quantity of glucose has been demonstrated by TLC and/or HPLC. There are several possible explanations for this phenotype. The level of glucose seen in this class is similar to the non-xanthan-specific or "unchaseable" glucose seen when all three sugar nucleotides are present for S4-L. This phenotype may be the result of a Transferase I defect, which would not allow charging of the lipid carrier with glucose. Alternatively, it could result from a defect in another gene that influences the initiation of the biosynthesis, directly or indirectly affecting the expression of Transferase I.

Transferase II

Two mutant lysates showing a significant accumulation of glucose on the lipid carrier were observed. The glucose was not polymerized to cellobiose on the lipid carrier. These lysates were unaffected by the presence of GDP-mannose and UDP-glucuronic acid. No radiolabeled material was found in the gum fraction. This defect is thought to be in the gene for Transferase II.

Transferase III

The radiometric analysis of the cell-free biosynthetic reaction mixes from some lysates showed that, in the presence of UPD[$^{14}$C]glucose, the organic fraction charges well (37% of the S4-L level). In the presence of all three sugar nucleotides, the charging with glucose was at the same high level, but there was no incorporation of either mannose or glucuronate. The gum fraction showed that no polymeric material (cellulose) was synthesized. The freed sugars from the organic fraction were analyzed by TLC and these mutants were shown to synthesize cellobiose very efficiently. The cellobiose accumulated in the organic fraction. The presence of GDP-mannose or UDP-glucuronate did not affect the accumulation of the cellobiose; the cellobiose did not appear to be processed further. These data indicate that these mutants have a defect in the Transferase III.

Transferase IV

Some mutant lysates (including lysates from X655, ATCC No. 53195) show the accumulation of the lipid-linked trimeric intermediate (described in U.S. Patent Application of Vanderslice et al., Supra.) in the organic fraction which has a molar ratio of 2:1 glucose to mannose. The gum fraction of each cell lysate in this group contains radiolabeled polytrimeric gum. These mutants are in the gene for Transferase IV, the glycosyl transferase that transfers glucuronic acid to the lipid-linked oligosaccharide precursor.

Transferase V

Mutant strains of this type would accumulate the tetrameric oligosaccharide on the lipid carrier and presumably produce an altered polysaccharide missing the terminal mannose and pyruvate.

Polymerase

Mutant strains with a defective Polymerase may accumulate the lipid-linked pentameric building blocks and be unable to polymerize them. This phenotype was not observed. A defective gene for the Polymerase may result in a different biochemical phenotype, such as no charging, or a lethal phenotype to the organism. Specifically, Polymerase mutants might show a Transferase I phenotype.

Acetylase and Ketalase

These defects were found in Gum+ strains. Polysaccharide was harvested after growth by centrifugation of culture broth at 12,000×g for 30 minutes to one hour at 10°–20° C. Precipitated gum from the supernatant was analyzed after hydrolysis by HPLC. The HPLC analysis of the hydrolyzed gums show that some mutants produce xanthan gum without pyruvate, and some mutants produce xanthan gum with 2:2:1 molar ratios of glucose to mannose to glucuronate with no acetate. In vitro data confirmed these results. These mutations eliminate the Ketalase or the Acetylase, respectively.

Example 3

Example 3 is the preparation of a library of total genomic X. campestris DNA in lambda 1059.

Bacteriophage lambda 1059 is a substitution cloning vector constructed by Karn et al. in Proc. Natl. Acad. Sci. U.S.A. 77:5172–5176 (1980), specifically incorporated herein by reference. The chromosome of this phage contains a 14 kb central region delimited by two BamHI sites. This central BamHI fragment (hereinafter referred to as the "stuffer" fragment) contains no genetic functions necessary for phage growth and can thus be removed and replaced with foreign DNA. The two arms of the vector contain all of the essential genetic functions for lambda replication and maturation. Viable phage particles are produced by ligating a DNA fragment having a size of 6 kb to 24 kb between the left and right arms of the vector DNA. Ligations of the left and right arms to each other do not yield viable phage particles because the genome size is too small for proper packaging into phage heads.

The "stuffer" fragment of lambda 1059 carries the lambda red (exo and beta genes) and gamma under the control of the leftward promotor (pL). These genes confer a Spi$^+$ phenotype on the vector, i.e., the phage is able to grow on recA$^-$ strains but is unable to grow on strains that are lysogenic for bacteriophage P2. Since pL is also located on the "stuffer" fragment, the expression of the Spi+ phenotype is not affected by the orientation of the "stuffer" between the left and right arms of the vector.

Vector DNA digested with BamHI is ligated with genomic DNA prepared by digestion with any restriction enzyme that generates "sticky" ends that are compatible with the cohesive ends of BamHI (e.g., BglII, BclI, and Sau3A). Cleavage of genomic DNA by Sau3A is an effective technique for generating a nearly random population of high molecular weight DNA fragments because the recognition site for cleavage by this enzyme occurs on an average of once in every 256 bp. Viable phage particles containing an insert of foreign DNA will express a Spi$^-$ phenotype and, thus, be able to grow on P2 lysogens but not on recA$^-$ strains.

High molecular weight (greater than 100 kb) genomic DNA was isolated from 2 liters of S4-L rif-101 using procedures described by Saito and Muria as described in Blochem. Biophys. Acta 72:619–629, specifically incorporated herein by reference. High molecular weight X. campestris genomic DNA was partially digested with Sau3A using reaction conditions which generated a collection of fragments with a predominant size of 15–20 kb. In order to avoid spurious linkage from multiple ligation events, the fragments produced by Sau3A digestion were rigorously fractionated on a 10–40% sucrose gradient to a size of 15–24 kb. The size of the DNA was confirmed by running a small aliquot on a 0.4% agarose gel.

Phage lambda DNA was isolated from phage particles purified by equilibrium centrifugation through CsCl gradients. The lambda 1059 DNA was digested with BamHI and SalI. BamHI digestion separates the left and right arms from the "stuffer" fragment. SalI digestion further cleaves the "stuffer" and thereby limits the reformation of the cloning vector during ligation. A 2 ug aliquot of the BamHI-SalI digested vector DNA was mixed with 0.6 ug of 15–24 kb fragments produced by Sau3A cleavage of X. campestris DNA and ligated with T4 ligase. The ligated DNA was packaged in vitro using lambda packaging mix obtained from Boehringer Mannheim.

Dilutions of the packaged DNA were used to infect three different E. coli strains: a nonrestrictive strain Km392, a recA$^-$ strain KRO, and a P2 lysogen strain, Q359. Strain Km392 is LE392 carrying Tn5 inserted into proC and is described by Young, R. A. in Science 222:778–782 (1983), specifically incorporated herein by reference. Infection of KM392 gave a titer of 1×10$^6$ while infection of KRO and Q359 gave titers of 6×10$^4$ and 1.2×10$^5$, respectively. The titer on KM392 is a measure of the total viable phage. The titer on KRO is a measure of the number of phages without an insert of X. campestris DNA, while the titer on Q359 indicates the number of phages containing an insert of X. campestris DNA. The relatively large number of viable phage that do not contain an insert of X. campestris DNA was surprising since double digestion of the vector DNA with BamHI and SalI should have prevented the formation of a significant number of lambda 1059 particles through religation events. It should also be noted that the total number of viable phage determined by adding the titers on KRO and Q359 is approximately five-fold lower than the total viable phage determined from infection of KM392. One interpretation of these results is that the plating efficiency of phage with and without insert DNA is about five-fold less on both KRO and Q359 than on KM392. In other words, the number of phage with and without an insert of *X. campestris* DNA is actually five-fold greater than the combined titers of KRO and Q359 indicate.

This interpretation was tested by determining the proportion of phage growing on KM392 that contain insert DNA. The phage present in 48 isolated plaques growing on KM392 were toothpicked to drops of sterile buffer and then printed in turn on a lawn of Q359 cells, KRO cells, and KM392 cells. All of the isolates grew on KM392, 62% grew on Q359 but not on KRO, and 38% grew on KRO but not on Q359. Thus, the proportion of phage growing on KM392 that carry an insert of *X. campestris* DNA is 62%. This value is in good agreement with the predicted value of 66% ($1.2 \times 10^5 / 1.8 \times 10^5$) and indicates that the actual number of viable phage containing insert DNA is $6 \times 10^5$.

Additional proof that *X. campestris* DNA had been successfully cloned was obtained by isolating the DNA present in six independent clones that grew on KM392 and Q359 but not on KRO. The size of each isolated phage chromosome was found to be slightly greater than the size of the lambda 1059 chromosome, indicating that the insert present in each clone is larger than the 14 kb "stuffer" fragment. A BamHI digest of the DNA from each of the isolates showed that each had a unique restriction pattern that was different from the BamHI restriction pattern of lambda 1059.

Example 4

This example describes the screening of the library of *X. campestris* DNA and demonstrates that some of the genes involved in xanthan biosynthesis are clustered.

Mutants of *X. campestris* that do not produce xanthan gum were isolated using Tn10 mutagenesis. The tetracycline resistance encoded by Tn10 has been used to clone restriction endonuclease fragments containing Tn10 and the chromosomal DNA from 35 gum::Tn10 mutants. These chromosomal sequences that flank the Tn10 insertion site provided hybridization probes used to identify wild-type *X. campestris* DNA sequences cloned in the lambda genomic library and to produce a physical map of gum::Tn10 mutations.

Chromosomal DNA was extracted and purified from the gum::Tn10 mutants as described above in Example 3. This DNA was digested to completion with restriction endonuclease PstI. This enzyme does not cleave within Tn10. Therefore, one chromosomal PstI fragment will contain the Tn10 element intact and fused to the *X. campestris* chromosomal DNA adjacent to the insertion site. The digested DNA was ligated to PstI-digested plasmid RSF1010 as follows.

Digestions were monitored by running aliquots of the reactions on agarose gels. In a typical ligation reaction, approximately 8 ug of plasmid and approximately 5 ug of chromosomal DNA were combined in a total volume of 200 ul. Approximately 20 units of T4 DNA ligase (New England Biolabs) were added and reactions were incubated at 12° C. for approximately 16 hours. The extent of ligation was assayed by agarose gel electrophoresis of an aliquot of the reaction prior to transformation.

Ligation products were used to transform *E. coli* LE392, selecting for resistance to streptomycin (carried by RSF1010) or tetracycline. The entire ligation reaction was then used to transform *E. coli* LE392. Selection for $Tet^r$ transformants should select for recombinant plasmids that contain both the large PstI fragment of RSF1010 (which provides replication function) and the PstI fragment of chromosmal DNA that contains Tn10 (which provides tetracycline resistance). For the transformation procedure, the ligation reaction is ethanol precipitated, resuspended in 50 ul of buffer, and added to 0.2 to 1.0 ml of cells (made transformation-competent by $CaCl_2$ treatment) at a concentration of about $3\times10^9$ per ml. This mixture is incubated on ice for 45 minutes, heat-shocked at 43° C. for two minutes, diluted five-fold with Luria broth, incubated at 37° C. for 60 minutes, and finally concentrated and plated on the appropriate drug-containing medium.

All ligations with chromosomal DNA's containing Tn10 gave some tetracycline-resistant transformants which contained recombinant plasmids carrying cloned Tn10 DNA. No tetracycline-resistant transformants were obtained from control transformations with RSF1010 alone, with no DNA, and, most significantly, with a ligation reaction using chromosomal DNA extracted from S4-L str-101 which does not carry Tn10. The frequency of streptomycin-resistant transformants in this control ligation was, however, equivalent to the frequencies of streptomycin-resistant transformants obtained from the other ligations.

Tetracycline-resistant transformants were analyzed for the presence of recombinant plasmids carrying Tn10. Colonies were picked and grown overnight in LB with 10 ug/ml tetracycline. Plasmid DNA was prepared using a standard, cleared lysate technique as described by Clewell and Helsinki in Biochemistry 62:1159–1166 (1969), specifically incorporated herein by reference. Plasmids were analyzed by digestion with appropriate restriction endonucleases. In order to test for the presence of Tn10 on the plasmid, a HindIII digest was done. Tn10 contains two internal HindIII fragments, 4.8 kb and 0.5 kb in length. Thus, all recombinant plasmids should generate these two fragments when cut with HindIII. Additionally, when cut with PstI, all recombinants should yield an 8.1 kb fragment derived from RSF1010, plus a second, larger fragment which ought to be greater than 9.3 kb. This is the PstI fragment of chromosomal DNA that contains Tn10, which is itself 9.3 kb in length.

Nearly all plasmids examined appeared to contain Tn10 by these criteria. However, PstI digests often revealed the presence of more than two PstI fragments. Presumably, these "extra" fragments are the result of multiple ligation events. These extra fragments are undesirable because, if such a recombinant were used as a hydridization probe, annealing to DNA fragments homologous to the extraneous PstI fragment could occur, as well as annealing to the PstI fragment that contains sequences from the gene of interest.

In order to eliminate the extraneous PstI fragments, the Tn10-containing fragment was then "recloned." Purified plasmid DNA was prepared over CsCl gradients and digested to completion with PstI. Digestion products were ligated at low DNA concentration (approximately 10 ug/ml). At this relatively low concentration, most ligation events should circularize linear fragments. Occasional dimer circles will be formed and higher order multimers should be rare.

The extent of ligation was assayed by gel electrophoresis of an aliquot of the reaction, and, in general, little multimet formation could be observed. The ligation reaction was then used to transform *E. coli* LE392, and tetracycline-resistant transformants were selected. The plasmids present in these transformants were then analyzed; they were nearly always found to have the desired recombinant structure. That is, they contained two, and only two, PstI fragments: one 8.1 kb in size, which is derived from RSF1010, and a second fragment greater than 9.3 kb in size, which is the *X. campestris* chromosomal fragment containing the Tn10 and the adjacent genomic DNA. These resulting recombinant plasmids were designated pTXnnn, where T stands for tetracycline resistance, and Xnnn is the strain number of the gum::Tn10 mutant from which the tetracycline resistance is cloned. For example, plasmid pTX655 was derived by cloning the tetracycline-resistance determinant out of gum::Tn10 mutant strain X655.

The Gum⁻ mutant designated X655 produces a polysaccharide having subunits with a trimer structure instead of the normal pentamer structure. This mutant is described more fully by Vanderslice et al., supra. It seemed possible that the gum biosynthetic gene defined by this mutation might be part of a cluster of genes that are coordinately expressed and regulated to bring about gum biosynthesis. To test this possibility, a set of 26 lambda 1059 clones carrying *X. campestris* DNA that hybridizes with plasmid pTX655 (called henceforth lambda 655(+)) was isolated and purified. Since the gene bank had not been amplified, each clone contained *X. campestris* DNA derived from an independent ligation event. The effect of this was to "walk" along the chromosome in the region of the genome carrying the gum gene defined by the X655 mutation. Since each cloned fragment is approximately 15 kb, the "walk" covered about 30 kb.

The set of 26 phage clones was then hybridized in turn with probe DNA cloned from each of 35 gum::Tn10 mutants. Twenty-four of thirty-five plasmid probes were found to hybridize with either all or some of the 26 phage clones in the set. These results indicate that at least some of the gum genes are clustered in the same region of the *X. campestris* genome that contains the gum biosynthetic gene defined by the X655 mutation, Transferase IV.

The 26 lambda 655(+) recombinant phages contain, as a population, approximately 30 kb of chromosomal *X. campestris* DNA centered around the PstI fragment cloned in pTX655. By hydridizing the other 34 pTX plasmids against these phages, it was determined which of the other Gum⁻ mutants had Tn10 insertions within this 30 kb segment. All 35 pTX plasmids were radiolabeled by nicktranslation and hybridized to filter-bound lambda 655(+) phage DNA along with lambda 1059 cloning vector DNA, which served as a negative control.

Nick translations were carried out in 50 mM Tris-HCl (pH 7.5), 10 mM EDTA, 1 mM DTT, and 50 ug/ml BSA (Sigma Pentax Fraction V). Typical reaction volume was 30 ul and generally 0.4 ug of DNA was added. Cold dNTP's were each present at 20 uM, and $^{32}$P-labeled dNTP's were each present at 3.3 uM. A total of approximately 80 uCi of $^{32}$p was added with each hot dNTP; generally one or two nucleotides were labeled. This reaction mixture was treated with DNAaseI (1 uliter of a 0.1 ug/ml solution) for 1 minute at 37° C. Subsequently, 1 ul of *E. coli* DNA polymerase I (5 units as defined by Richardson et al. (1964)) was added to the reaction. After incubation at 37° C. for 30 minutes, the reaction was ethanol preciptated with carrier DNA. The pellet was washed with 70% ethanol, vacuum-dried, and resuspended in 200 ul 10 mM Tris-Hcl (pH 8.0), 1.0 mM EDTA.

Hybridizations were conducted by the following method. Nitrocellulose filter bound lambda DNA's were prepared using the protocols of Davis et al. (1980). These filters were prehybridized in 5× SSPE, 5× Denhardt's solution (Maniatis et al. supra), 0.1% SDS, and 50% formamide containing 100 ug/ml denatured, sonicated calf thymus DNA for 4–16 hours at 42° C. on a rocker. The hybridization reaction itself was done in 2× SSPE, 1× Denhardt's solution, 56% formamide containing 100 ug/ml denatured, sonicated calf thymus DNA. Radiolabeled 32p probe DNA's were denatured in 0.1M NaOH and neutralized by addition of ⅒ volume of 2M Tris-HCl (pH 8.0). Typically, 10⁶ cpm of incorporated $^{32}$P were added per ml of hybridization reaction. Hybridizations were incubated at 42° C. for 12–20 hours on a rocker. Subsequently, filters were washed at room temperature, once in 2× SSPE and then once in 0.1× SSPE. Filters were blotted on Whatman 3 MM paper and allowed to air dry. The filters were then placed under Kodak X-OMAT AR film and exposed for 4–16 hours at −70° C. A Du Pont Cotonex intensifying screen was employed.

It was found that 25 of the 35 plasmids hybridized to some or all of the lambda 655(+) phage DNA's. Ten probes failed to hybridize to any of the lambda 655(+) phage. Thus, a sizable fraction of the gum::Tn10 mutations (approximately 60%) are located within this cloned 30 kb region, but a significant number lie outside this DNA segment.

The hybridization data allow classification of the lambda 655(+) phage on the basis of which probes hybridized and which failed to hybridize. These hybridization patterns reflect the DNA segments cloned in each phage. Because each of the cloned DNA fragments is a single contiguous piece of the *X. campestris* chromosome, the order of the mutations in the genome was deduced from the classes of hybridization patterns. The presence or absence of particular DNA fragments correlates well with hybridization to, or failure to hybridize to, particular probes.

The restriction maps and hybridization data indicated that the mutant X708 was located quite near one end of the cloned 30 kb segment of *X. campestris* DNA. The *X. campestris* chromosome was thus "walked" along by isolating recombinant lambda phage that hybridized to the pTX708 plasmid. Twenty-six such recombinants were picked and analyzed by restriction mapping as described above. This set of phage extended the cloned region by approximately 8 kb.

All 35 pTX plasmid probes were then hybridized to this set of recombinant phage using the same procedures employed in hybridizations with the lambda 655(+) phage. The same 25 pTX probes annealed to some or all of the lambda 708(+) phage, and the same set of probes that failed to hybridize to any lambda 655(+) phage also failed to hybridize to any of the lambda 708(+) phage. Again, the restriction maps of the lambda 708(+) phages permitted correlation of the presence or absence of particular DNA fragments with hybridization to particular plasmid probes. In summary, then, from these hybridizations, 25 mutations were found to be clustered in a region of DNA in the near vicinity of the mutation carried in the Transferase IV- strain X655. Ten mutations did not map to this region of DNA. Some of these mutations are described above and by Betlach et al., supra. These mutations do not alter the gum biosynthetic enzymes.

Example 5

This example describes the restriction mapping of cloned DNA carrying clustered gum biosynthetic genes.

Since a large number of the gum genes defined by the collection of Tn10 insertional mutations were found to be clustered around the location of X655 mutation, the region of the *X. campestris* genome carrying these genes was further characterized by restriction enzyme mapping. This was accomplished by generating a restriction enzyme map of the cloned DNA present in each of the 26 phage clones constituting the set of overlapping fragments carrying the gum gene cluster.

Since each of the phage clones contained lambda 1059 DNA in addition to the cloned *X. campestris* DNA, the restriction enzyme analysis was done with a restriction enzyme that would readily permit the distinction of the lambda DNA from the *X. campestris* DNA. One such enzyme is BamHI. Because there are no BamHI sites in either of the two arms of lambda 1059, the lambda DNA present in each BamHI digest will always be located in two bands: one greater than or equal to 20 kb contains lambda DNA from the left arm, the other greater than or equal to 9 kb contains lambda DNA from the right arm.

DNA isolated from each of the 26 phage clones was digested with BamHI. Since the restriction fragments produced ranged in size from greater than 20 kb to less than 0.5 kb, the digests were run on low percentage agarose gels (to separate the large fragments) and at high voltage (to reduce diffusion of the smallest fragments). The gels often used an agarose concentration of 0.4% run at 100 volts for about 5 hours. Each gel contained samples of the phage clones digested with BamHI, a HindIII digest of wild-type lambda DNA (for use as a size standard), and a BamHI digest of lambda 1059 DNA (to mark the location of vector DNA in the sample digests). The distance migrated by each restriction fragment in the sample digests was measured and converted to a molecular size using a standard curve prepared from the HindIII digest of wild-type lambda DNA.

The restriction patterns generated by the BamHI digests of the DNA present in each of the 26 phage clones were analyzed to determine the regions of overlapping DNA in each of the phage clones. From the pattern of overlaps, the order of the restriction fragments in each of the digests was determined (FIG. 2).

Since the position of the X708 mutation was very close to one end of the cloned DNA, it seemed possible that one or more of the 10 pTX probe DNA's that did not hybridize was located just outside of the region of the DNA contained in the set of overlapping phage clones. This possibility was tested by isolating a set of lambda clones which hybridize with pTX708 from the gene bank. In this way, the region of the *X. campestris* genome contiguous with the gum gene cluster was extended beyond the location of the Gum⁻ mutation present in X708. BamHI restriction maps were prepared for the DNA contained in these clones (FIG. 3).

To determine if there were any very small BamHI restriction fragments (less than 0.5 kb) that were not detected on 0.4% agarose gels, selected phage clones containing DNA derived from the entire cloned region were digested with BamHI and run on a 5% polyacrylamide gel. Such a gel can resolve fragments as small as 30 bp. This experiment revealed the presence of two previously undetected BamHI fragments having sizes of 300 bp and 190 bp.

Figures 4, 5A, 5B:
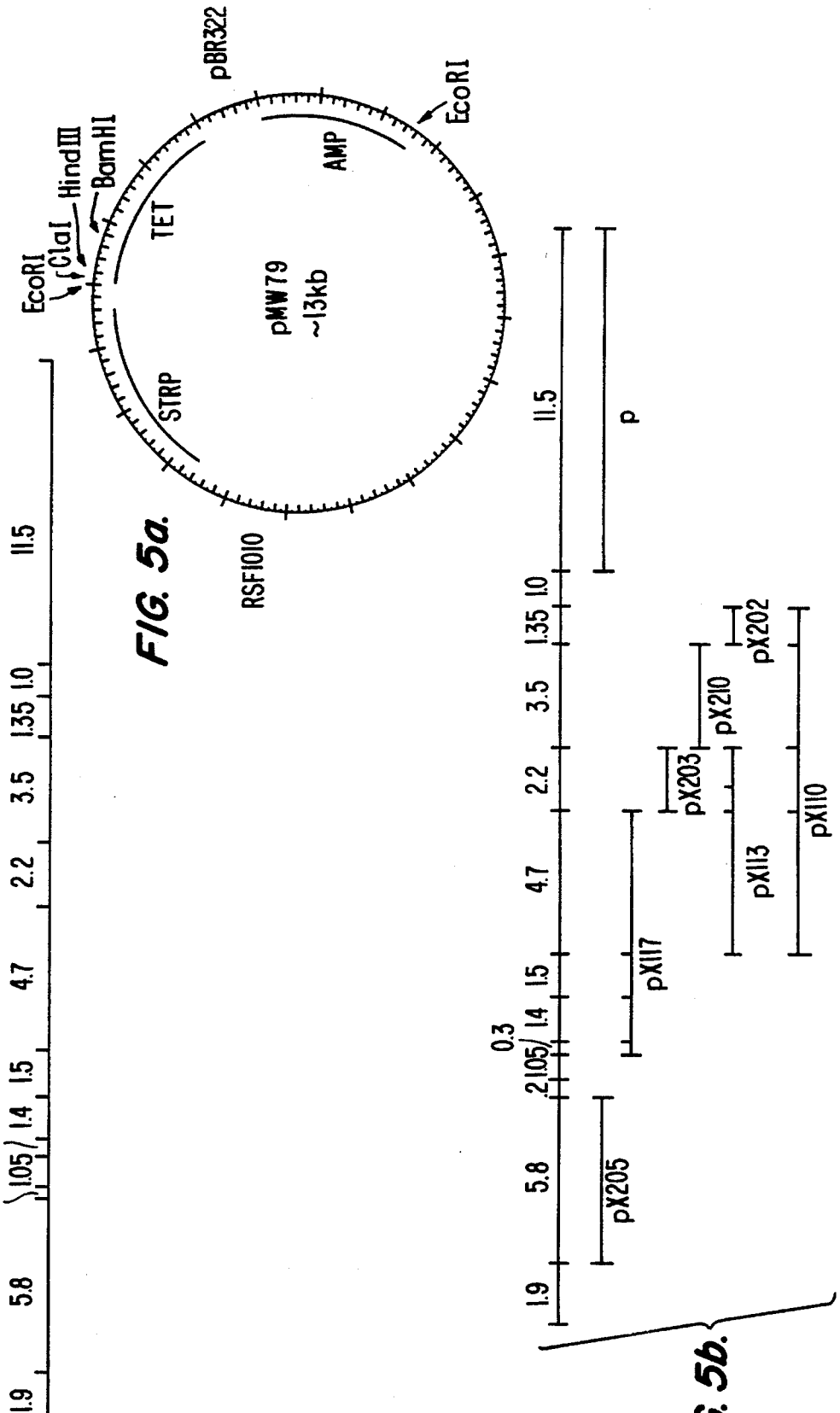
FIG. 4 is a BamHI restriction map of the region of the *X. campestris* genome containing the gum gene cluster. The numbers are the molecular size of the fragment in kilobases (kb).
FIG. 5a shows the general structure and pertinent restriction endonuclease cleavage sites of cloning vector pMW79.
FIG. 5b depicts a representative, but not inclusive, sample of segments of gum gene DNA cloned into the BamHI site of pMW79 from either partial or complete digests of various lambda recombinants with BamHI as described in Example 6.

Further analysis of these data indicated that the 300 bp fragment is located between the 1.05 fragment and 1.4 kb fragment, while the 190 bp fragment is located between the 5.8 kb fragment and 1.05 kb fragment. All of the BamHI restriction mapping data and the probe hybridization data were combined to generate a physical and genetic map of a region of the *X. campestris* chromosome that carries a cluster of genes involved in xanthan gum biosynthesis (FIG. 4).

Example 6

Example 6 describes the subcloning of gum gene cluster DNA from the lambda 1059 library onto the broad-host range plasmid vector pMW79.

The vector pMW79 is described in detail by Wood et al. in J. Bact. 14:1448–1451 (1981), specifically incorporated herein by reference. Briefly, it is a chimetic plasmid combining the broad-host range, Inc-Q plasmid RSF1010 and the classical *E. coli* cloning vector pBR322 (see FIG. 5a). pMW79 can be transferred to, and propagated in, a wide variety of gram-negative bacteria and retains many of the useful cloning sites present in pBR322. Cloning sites in the pBR322 portion of the plasmid have been principally used and in particular sites have been used that occur within the tetracycline resistance gene.

The lambda 1059 phage clone 655 (I) contains the entire region of the *X. campestris* genome that carries the gum genes defined by our Tn10 mutations. *X. campestris* DNA in phage clone I was subcloned into the plasmid cloning vector pMW79.

A partial BamHI digest of DNA isolated from lambda clone 655 (I) was ligated with a BamHI limit digest of pBR322 and pMW79. The ligated DNA was used to transform KM392 selecting Amp$^r$ transformants. A total of 1200 Amp$^r$ transformants were printed on agar plates containing tetracycline to determine which of the transformants are Tet$^s$ and, thus, likely to contain an insert in the unique BamHI site located in the Tet gene of pMW79. Sixty Amp$^r$ Tet$^s$ transformants were isolated and streak purified. Plasmid DNA was then isolated from each of the transformants, digested with BamHI, and the digests were run on 0.4% agarose gels to ascertain the presence and extent of *X. campestris* DNA.

The majority of the isolated plasmids contained no insert DNA. However, 19 were found that did contain inserts. Nine of the 19 contained a single fragment insert, while 10 contained inserts composed of two or more fragments. In all 10 cases where two or more BamHI fragments are present in the cloned DNA, the fragments are contiguous on the BamHI restriction map of lambda clone 655 (I). This finding provides independent evidence that the order of the BamHI fragments in lambda clone 655 (I) is correct. With the exception of the 1.0 kb fragment on the right end, all of the Xamthomonas DNA present in lambda clone 655 (I) is represented in one or more of the subclone derivatives.

Clones of pMW79 containing either the 5.8 kb fragment or the 11.5 kb fragment (which are not contained in lambda clone 655 (I) were prepared in a separate experiment by ligating BamHI limit digests of lambda clone 655 (C') and lambda clone 708 (8) with BamHI-digested pMW79. A representative sample of *X. campestris* DNA fragments that were thus cloned into pMW79 is shown in FIG. 5b.

In a series of steps, a single large (20 kb) segment of DNA spanning the region that is genetically implicated in xanthan gum biosynthesis was cloned into pMW79. Steps followed in this cloning were as follows. Phage lambda clone 655(B) (FIG. 2) DNA was digested to completion with BglII and HindIII and ligated with plasmid pMW79 DNA digested to completion with BamHI and HindIII. BamHI and BglII cut different sequences but create identical cohesive ends; thus, -BamHI ends can be ligated to BglII ends. The ligation products were used to transform *E. coli* selecting for ampicillin resistance encoded by pMW79. Eighty-eight Amp$^r$ transformants were screened for resistance to tetracycline and 75 Tet$^s$ isolates were found. Cloning into the BamHI-HindIII region of pMW79 results in inactivation of tetracycline resistance. The high frequency of Tet$^s$ transformants occurs because HindIII and BamHI ends cannot be ligated together to reseal the plasmid; insertion of a DNA fragment is required for recircularization. Six Tet$^s$ transformants were analyzed for plasmid. Small-scale cleared lysates were prepared, digested with BamHI, and run out on agarose gels. Two transformants proved to have plasmids carrying the desired fragment. One isolate was grown up for a larger plasmid preparation. This plasmid DNA was purified by CsCl density gradient centrifugation and reanalyzed by various restriction endonuclease digestions. This plasmid (now termed pX206) had the expected structure, shown in FIG. 6, as evidenced by the cutting patterns of these restriction endonucleases.

Figure 6:
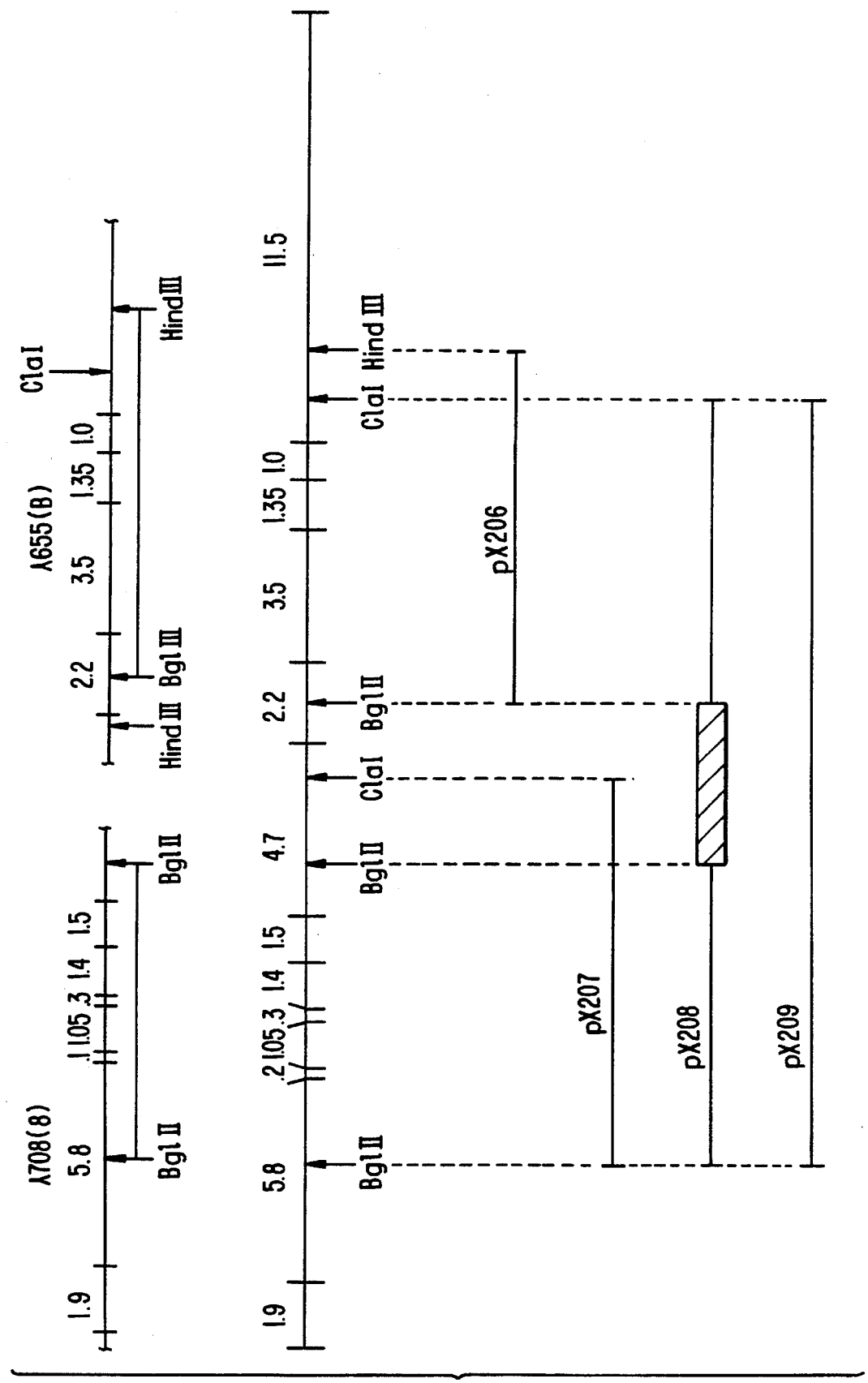
FIG. 6 depicts partial restriction maps of two recombinant lambda phages (lambda 708(8) and lambda 655(B)) shown in relation to the BamHI restriction map of the *X. campestris* DNA in the vicinity of the gum gene cluster. The cloned segments of gum gene DNA carried in four recombinant plasmids (pX206, pX207, pX208, and pX209) are also shown. For simplicity, the pMW79 vector sequences of these plasmids are not depicted, but the details of these constructions are given in Example 6.

An attempt was also made to clone the 8 kb BglII fragment of lambda 708(8) as shown in FIG. 6. Purified lambda 708(8) DNA was digested to completion with BglII and ligated with BamHI-cut pMW79 DNA. The ligation mixture was used to transform *E. coli*, again selecting for Amp$^r$. One hundred sixty-six Amp$^r$ transformants were tested for resistance to tetracycline and 49 Tet$^s$ isolates were found. Plasmid DNA from 18 of these was isolated and one recombinant plasmid that appeared to carry the BglII fragment of interest was found. A large-scale cleared lysate was prepared from this strain and purified the plasmid DNA over CsCl gradients. Further analysis indicated that this plasmid had the fragment of interest but contained a second, extraneous BglII fragment as well.

The structure of this fortuitous recombinant provided an opportunity to construct a more useful subclone. By chance, the locations of the BglII and ClaI sites in this plasmid provided an opportunity to digest with ClaI and BglII and then ligate in the 2 kb ClaI-BglII fragment that is contiguous in the gum gene cluster. This construction extends the cloned DNA present in the plasmid by 2 kb beyond the BglII site; this extra DNA was useful in facilitating gene replacement experiments. Additionally, this construct contained unique HindIII and BglII sites within the cloned Xanthomonas DNA. The structure of this plasmid, designated pX207, is shown in FIG. 6.

Subsequently, the large (8 kb) BglII-ClaI fragment of lambda 655(B) was inserted into pX207, replacing the small (2 kb) BglII-ClaI segment of pX207. Plasmid pX207 was digested to completion with both these enzymes and ligated with the DNA of the lambda recombinant lambda 655(B), which was also digested with BglII and ClaI. The double digestion with ClaI and BglII selects for recombinant plasmids among the transformants because BglII ends cannot be ligated to ClaI ends, and thus the pX207 plasmid cannot recircularize unless a second BglII-ClaI fragment is ligated into it. Indeed, the 12 transformants that were examined all contained recombinant plasmids, and one of these proved to be the desired recombinant. This plasmid, pX208, is shown in FIG. 6. This plasmid contains the gum gene DNA from the right-hand BglII site of the 5.8 kb BamII fragment through the ClaI site of 11.5 kb BamHI fragment, with the exception of an interstitial 4.5 kb BglII piece. The missing 4.5 kb BglII fragment was subsequently inserted into pX208 to create the large subclone of interest, termed pX209.

The pX208 plasmid DNA was linearized by digestion with BglII. The missing 4.5 kb BglII fragment was purified by electroelution out of a preparative agarose gel and ligated to the BglII-cut pX208. Ligation products were used to transform *E. coli* and ampicillin-resistant transformants were obtained. In this ligation, there is no selection for recombinants and there is no simple screening procedure. The transformants were screened for recombinant plasmids by the technique of colony hybridization (Maniatis et al., supra). This procedure is analogous to the plaque hybridization protocol used to screen lambda clones for DNA segments of interest. Transformants are toothpicked onto a "master" plate in an ordered array. This master plate is then used to produce a copy on a nitrocellulose filter. This filter copy is incubated on top of an agar plate with the result that bacterial growth occurs on the surface of the filter, fed by diffusion of nutrients from the agar through the filter. Subsequently, the bacteria on the filter are lysed in situ and DNA is irreversibly bound to the filter. This filter can then be probed with any radiolabeled DNA. In this instance, a radiolabeled 4.5 kb BglII fragment was used; only recombinants that acquired this fragment hybridized to the probe. Most transformants contained only the recircularized plasmid pX208 and did not hybridize. Five hundred and seventy-six transformants were screened using the 4.5 kb BglII DNA labeled with $^{32}$P by the nick translation procedure. Among these, 20 transformants were found that hybridized to the probe. Plasmid DNA's from some of these transformants were analyzed in order to verify the presence of the 4.5 kb fragment and determine its orientation. Plasmids from twelve such putative recombinants were analyzed using agarose gel electrophoresis. Eleven of these contained the expected BglII 4.5 kb fragment, and, of these eleven, eight carried the fragment in the correct orientation. One of these eight was picked for further analysis. This plasmid, designated pX209, is depicted in FIG. 6.

Example 7

This example describes methodology for in vivo and in vitro regionally-directed mutagenesis of the cloned gum gene DNA segment carried on pMW79.

Regionally-directed mutagenesis was performed upon subcloned portions of the gum DNA carried in plasmid pMW79. These cloned DNA segments were mutagenized in vivo with transposons and in vitro, by using recombinant DNA technology to generate insertion, deletion, and substitution mutations within the cloned *X. campestris* DNA. In order to study the phenotypes conferred by these mutations, the plasmids carrying the mutations were transferred back into *X. campestris* and subsequently recombinants were identified in which the plasmid-borne, mutated gene had been inserted in the chromosome via homologous recombination. The tetracycline resistance encoded by Tn10 affords a convenient selective system for movement of mutations from a plasmid into the chromosome.

In preliminary experiments designed to study recombination between plasmid-borne *X. campestris* DNA and the *X. campestris* chromosome, the plasmid pTX655 was used as a model system. This plasmid carries a Tn10 insert in the middle of a 2.3 kb *X. campestris* PstI fragment cloned in plasmid RSF1010. The experiment was to mobilize pTX655 with plasmid pRK2013 and transfer it from *E. coli* into *X. campestris* by selecting for movement of the tetracycline resistance encoded by Tn10. The initial results of this mating were anomalous and suggested that Tn10 did not express tetracycline resistance efficiently in *X. campestris* when carried on the plasmid, but that the drug resistance was more efficiently expressed when Tn10 was carried in the chromosome of *X. campestris.* This phenomenon has also been described for Tn10 in *E. coli.* There, it has been shown that strains carrying one copy of Tn10 inserted in the chromosome are resistant to significantly higher concentrations of tetracycline than are strains carrying Tn10 on a multicopy plasmid. The selection of $Tet^r$ *X. campestris* out of the above mating resulted in a high frequency (0.5 per recipient) of progeny which grew very poorly (i.e., only small, watery colonies) on tetracycline. After prolonged incubation, a large fraction of the colonies (25%) produced sectors of more vigorously growing cells. More than 50% of these sectors appeared to be Gum⁻ in morphology. These probably result from recombination between the plasmid-borne DNA containing the Tn10 insertion and the chromosomal wild type DNA. When the Tn10 is recombined into the chromosome, high-level Tet$^r$ is obtained and the vigorously growing sector is observed. When these Gum⁻ Tet$^r$ sectors were picked and restreaked on tetracycline, they grew well and displayed a characteristic Gum⁻ morphology. This strongly argues that the original X655 mutation has been reconstituted by recombination of the plasmid-carried Tn10 insertion into the chromosome.

Figure 7:
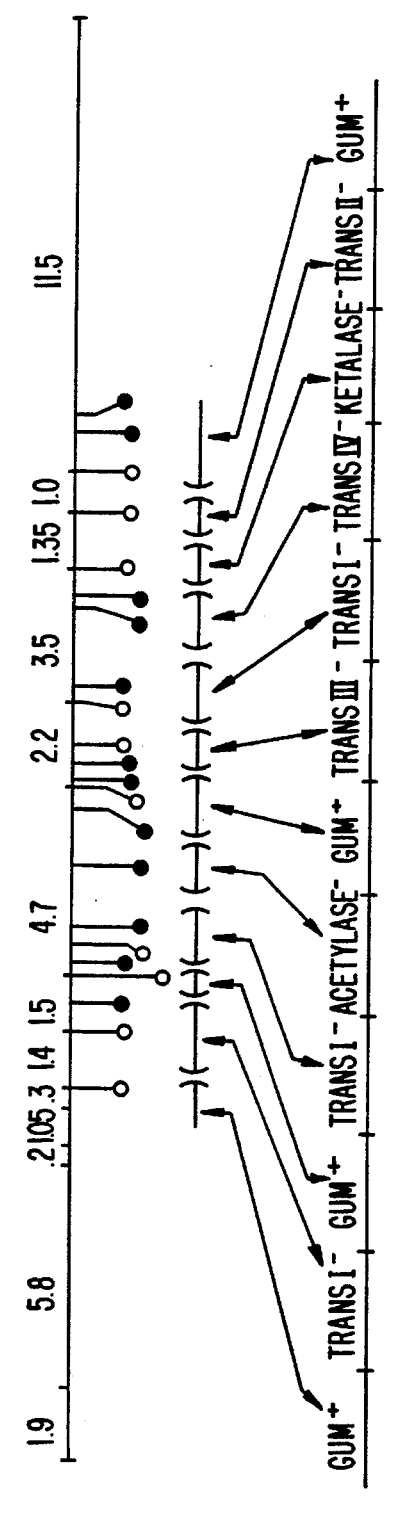
FIG. 7 shows the positions, within the BamHI restriction map of the gum gene cluster DNA, of 22 insertion mutations. Open circles indicate in vitro-generated insertions of the BglII Tet$^r$ fragment of Tn10, while filled circles represent in vivo-derived Tn10 insertions. Phenotypic classification of mutants carrying these insertions, as described in Example 2, is shown below.
Figure 8:
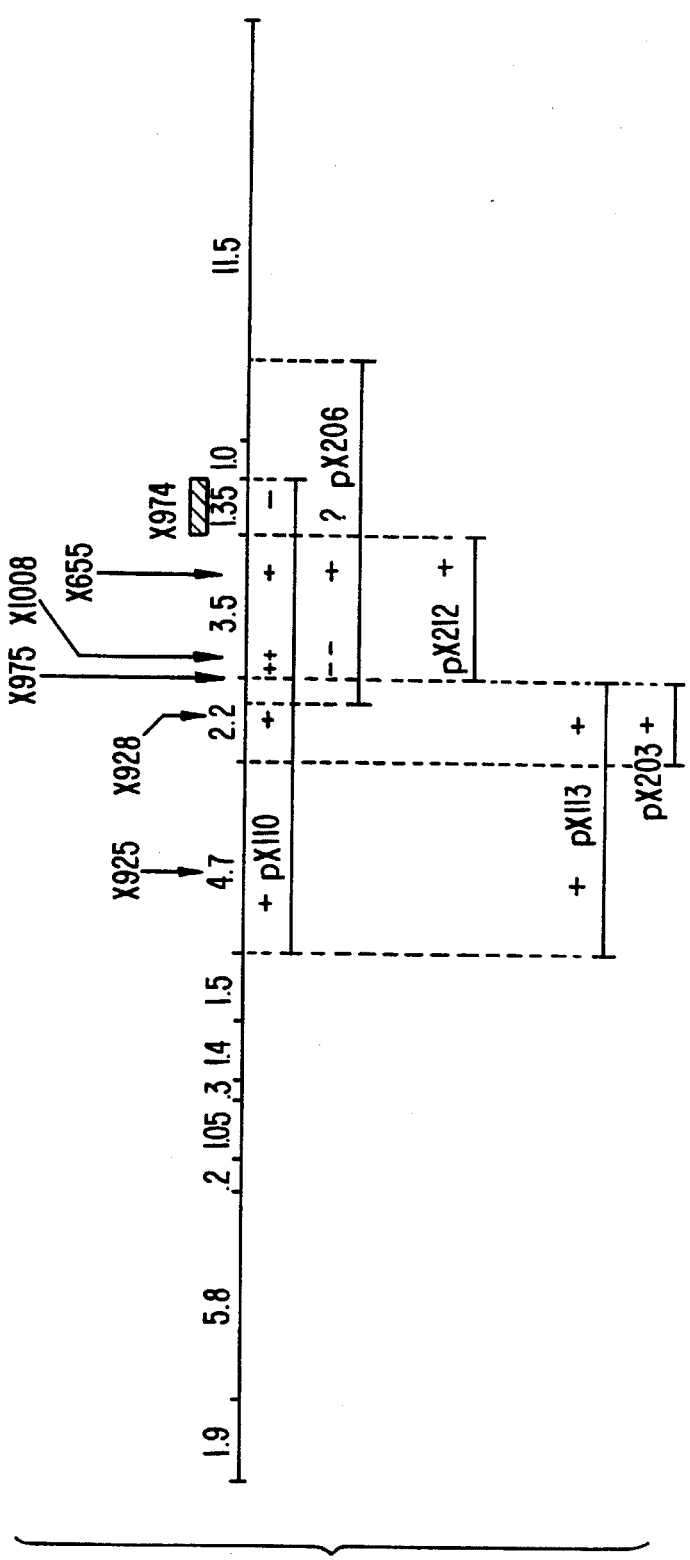
FIG. 8 depicts the location within the BamHI restriction map of a set of six representative mutations in the gum gene cluster. Strains X925, X928, X975, X1008, and X655 carry insertion mutations of Tn10 or the BglII Tet$^r$ fragment of Tn10 at the positions indicated. Strain X974 carries a deletion of the 1.35 kb BamHI fragment and a substitution of the BglII Tet$^r$ fragment at that position. Below the restriction map are shown representative plasmids used in complementation experiments with the above mutants. For simplicity, only cloned *X. campestris* sequences are shown; the vector pMW79 sequences are omitted. A plus sign (+) indicates successful complementation of the mutant by the plasmid, whereas a minus sign (−) denotes failure to complement. Details of the experiments and interpretations are given in Example 8.
Figure 9:
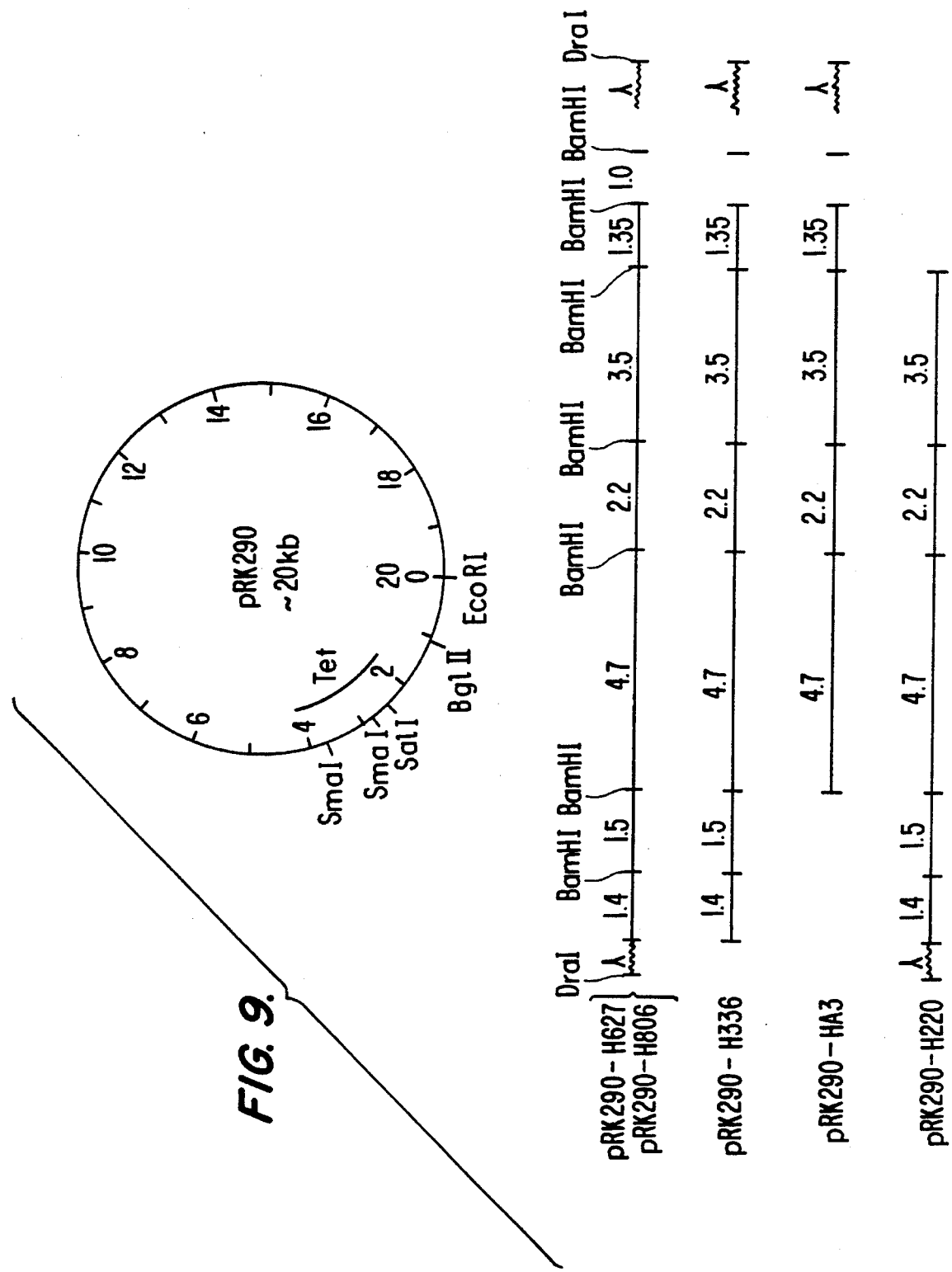
FIG. 9 shows a partial restriction map of plasmid pRK290 and various segments of DNA cloned out of the recombinant lambda phage 655 (L') and into the BglII site of pRK290 as detailed in Example 10.

Lambda 173, as described by Kleckner et al. in Genetics 90:426–461 (1978), specifically incorporated herein by reference, was used to introduce Tn10 into plasmids containing X. campestris DNA. This bacteriophage contains a temperature-sensitive repressor of lytic functions and a Tn10 insertion in a nonessential gene. Aliquots of this phage were used to infect a lambda-sensitive *E. coli* carrying a recombinant plasmid of interest at multiplicity of infection of 0.1 at 30° C. After 45 minutes (to allow phage adsorption, DNA injection, and expression of tetracycline resistance), the cells are pelleted to remove any unadsorbed phage. Then the cells are resuspended in Luria broth and aliquots containing $10^8$ cells are plated on Luria plates containing 20 ug/ml tetracycline, 100 ug/ml ampicillin, and 2.5 mM sodium pyrophosphate. The tetracycline selects for Tn10, while the pyrophosphate chelates magnesium to minimize secondary phage infections. The formation of lysogens is minimized by incubating the plates at 42° C. $Tet^r$ survivors arise at a frequency of $10^{-7}$ to $10^{-6}$. In an experiment designed for the purpose of plasmid mutagenesis, $10^{10}$ cells are infected with $10^9$ phage, and $10^2$ plates are spread. After 24-hour incubation, the colonies from each plate are suspended in 4 ml Luria broth and pooled on ice. After centrifugation, plasmids are extracted from the cells using a lysozyme-Triton cleared lysate protocol, and then plasmid DNA is purified by ethidium bromide-cesium chloride density gradient centrifugation. After further purification, the plasmid DNA is used to transform *E. coli* LE392 with selection for $Amp^r$, $Tet^r$. Subsequently, plasmid DNA is extracted from each transformant and cut with BamHI to localize the insertion to *X. campestris* DNA or vector DNA. Those plasmids with Tn10 inserted in *X. campestris* sequences are then mobilized into Gum+ *X. campestris.* Selection for tetracycline-resistant *X. campestris* out of this mating frequently results in movement of the plasmid-borne Tn10 insertion into the chromosome of *X. campestris* via homologous recombination, as detailed above. The phenotypic properties of *X. campestris* strains carrying these chromosomal insertions can then be analyzed.

A second strategy for isolating Tn10 insertion in vivo was also employed. This strategy used plasmid pRK2013::Tn10 described in Example 1 as a source of Tn10. Advantage was taken of the incompatibility between the $Amp^r$ pMW79 replicon (of pX113) and pRK2013::Tn10, and the lack of a SmaI restriction site in pX113. Rifr $Amp^r$ *E. coli* (pXl13) was mated with $Rif^s$ *E. coli* (pRK2013::Tn10), with selection for $Rif^r$ $Amp^r$ $Tet^r$. The selection for $Amp^r$ $Tet^r$ with the plasmid incompatibility should favor cells which sustain transpositions of Tn10 onto pXl13. Plasmid DNA was purified from a pool of several thousand colonies and then cut to completion with restriction endonuclease SmaI. Plasmid pRK2013::Tn10 has SmaI sites within the vector portion of the plasmid, while there are no SmaI sites within Tn10. The resultant DNA was used to transform a native *E. coli* to $Amp^r$ $Tet^r$. Only pX113::Tn10 plasmids should confer this phenotype during transformation. The plasmid content of $Amp^r$ $Tet^r$ transformants was analyzed by BamHI restriction endonuclease cutting and agarose gel electrophoresis. Some of them contained inserts of Tn10 within the cloned *Xanthomonas campestris* sequences. Such plasmid-borne insertion mutations could be introduced into the *X. campestris* chromosome via gene replacement as described above.

The in vitro mutagenesis experiments were also designed to exploit the useful properties of the Tn10 tetracycline resistance determinant. A 2.8 kb BglII fragment was purified from Tn10. Previous work has shown that this fragment contains intact the gene encoding the protein conferring tetracycline resistance and a regulatory gene which encodes a protein that regulates the expression of the resistance gene. In *E. coli,* at least, this regulatory gene must be functional for the difference between plasmid-borne and chromosomally-located tetracycline resistance to be observed. The DNA fragment of interest was purified from preparative agarose gels by electrophoretic elution of DNA out of gel slices (Maniatis et al., 1982). The eluted DNA was extracted with phenol two times, ethanol-precipitated, washed with 70% ethanol, vacuum dried, and resuspended in appropriate buffer.

In vitro insertions of this DNA fragment were subsequently made in BglII and BamHI sites present within cloned gum gene DNA carried on various pMW79 derivatives. In making these new constructs, advantage was taken of the fact that the cohesive ends of BamHI-cut DNA are identical to the cohesive ends of BglII-digested DNA; therefore, BglII-cut DNA can be ligated into a BamHI site. Plasmid DNAs were digested with BamHI in the presence of 20–80 ug/ml of ethidium bromide. In the presence of ethidium bromide, the activity of the restriction endonuclease is perturbed. The result is that this digestion produces a high proportion of singly-cut linear products. A priori, one would expect that the BamHI site that is cut would be chosen, more or less, at random and, to a first approximation, this appears to be so. The purified BglII $Tet^r$ fragment can be ligated to this population of linear fragments. The ligation products were used to transform *E. coli* and tetracycline-resistant transformants were selected. Plasmids were extracted from these transformants and analyzed by restriction endonuclease digestion. Plasmids carrying an insertion of the BglII $Tet^r$ fragment at either a BamHI or BglII site were then mated into *X. campestris* and the differential tetracycline resistance of the chromosomal vs. plasmid-borne $Tet^r$ element was used to identify homologous recombinational events that generate gene replacements. With slight modification of this technology, deletion mutations were also constructed. When the plasmid DNA's digested in the presence of ethidium bromide incurred two or more cleavages by BamHI, the segment flanked by the two cleaved sites was lost. When the $Tet^r$ BglII fragment was ligated to such linear plasmid molecules, the resultant recombinant contained a deletion of a segment of gum gene DNA. Plasmids containing deletions of gum gene DNA were also purposely constructed by ligating together noncontiguous segments of gum gene DNA. If the $Tet^r$ BglII fragment is present at the junction to two such cloned, noncontiguous gum gene cluster DNA segments, it often proved possible to introduce even very large deletions into the *Xanthomonas campestris* chromosome via gene replacement. For example, the deletion strain X1107, which deletes 15 kb of DNA from the gum gene cluster, was constructed by this technique.

Through the application of both in vivo and in vitro regionally-directed mutagenesis technology to a number of subcloned segments of gum gene DNA, numerous plasmid-borne insertions were obtained which subsequently gave rise to tetracycline-resistant *X. campestris* derivatives in the gene replacement experiment. A physical map of some of these insertion mutations is shown in FIG. 7. Southern blot hybridization analyses of the chromosomal DNA's of these gene replacement strains was performed in order to confirm that the positions of the chromosomal insertions corresponded to the positions of the plasmid-borne insertions from which they were derived. For these experiments, total chromosomal DNA was prepared from each putative gene replacement strain as described above. The purified DNA's were digested with diagnostic restriction endonucleases; usually BamHI, BglII, EcoRI, HindIII, or PstI, or some combination of the above. DNA digests were run out on agarose gels, transferred to nitrocellulose filters, and probed with radiolabeled plasmid DNA. Autoradiographs reveal the pattern of hybridization, which is compared to wild-type controls to deduce the location and orientation of the Tn10, or BglII $Tet^r$ fragment, insertion. All of the insertions shown in FIG. 7 were found to be genuine gene replacement strains. That is, no plasmid sequences were detected by hybridization and the chromosomal DNA's were altered from the wild-type by the indicated insertion mutation and by no other evident event. The phenotypes of all these insertion mutations were examined by in vitro and/or in vivo methodologies described in Example 2. The phenotypes thus identified are indicated on FIG. 7.

Example 8

This example describes procedures used in complementation experiments that demonstrate the expression, in *X. campestris*, of cloned gum biosynthetic genes carried on plasmid vectors.

Complementation experiments have been performed with plasmids carrying segments of gum gene DNA and $Gum^-$ insertion mutations within the gum gene cluster. The results of these experiments are summarized in FIG. 8. In these experiments, the plasmids were mated into *X. campestris* recipients and maintained there using selection for streptomycin resistance. The presence of plasmid was confirmed by making plasmid DNA preps out of each recipient strain and analyzing the plasmid DNA with restriction endonuclease digestion and agarose gel electrophoresis. Plasmid "curing" experiments were performed to demonstrate that loss of the plasmid was correlated to loss of the Gum+ phenotype in complemented strains. In general, mutants were complemented by plasmid DNA's that spanned the mutational insertion site. For example, plasmid pX110 complemented X925, X928, X975, and X655 but not the deletion mutant strain X974. The gum gene DNA carried by plasmid pX110 extends significantly beyond the insertion sites of all the complemented mutations. However, as seen in FIG. 8, the deletion mutation in X974 extends right up to the right-hand endpoint of cloned gum DNA carried in pX110. It is possible, therefore, that pX110 does not carry an intact copy of the gene eliminated by the deletion in strain X974. In fact, the failure to obtain complementation of X974 by pX110 argues that this is the case.

A surprising result was the failure of pX206 to complement X974. This plasmid also fails to complement X975, but the cloned segment extends only 1.0 kb beyond the site of the X975 insertion. It is entirely plausible that some element (e.g., a promoter) that is required for expression of the gene that is mutated in X975 is located outside the cloned segment in pX206. The failure of pX206 to complement X974 is more perplexing since the cloned gum gene DNA extends 4 to 5 kb beyond the mutation site in both directions. However, this particular mating was unique in that it gave an unusually low frequency of plasmid transfer. This frequency was three orders of magnitude lower than that observed in all other matings in this set of experiments. In all other matings, the plasmid pX206 was transferred at the higher frequency, and in all other matings with X974 as the recipient, the higher transfer frequency was observed. Thus, there may be a negative impact resulting from combination of that particular chromosomal mutation and that particular cloned DNA segment.

Most of the complementation results can be interpreted in a straightforward manner. The plasmid-borne gum genes can be expressed at least in *X. campestris*.

Example 9

This example illustrates the sequencing of DNA from the gum gene biosynthetic cluster.

The nucleotide sequence of the cloned segment of DNA containing the gum gene cluster is being determined using the dideoxy chain termination sequencing procedures described by Sanger et al. in Proc. Natl. Acad. Sci. USA 74:5463–5468 (1977) specifically incorporated herein by reference. Each of the BamHI fragments contained in the gum gene cluster have been cloned (in both orientations) into the M13 cloning vectors MP18 or MP19. Each cloned fragment was then subcloned using a procedure described by S. Henikoff in Gene 28:351–359 (1984) specifically incorporated herein by reference. By sequencing the DNA contained in a nested set of overlapping subclones, a nucleotide sequence for the entire cloned BamHI fragment can be obtained. Thus far, a complete sequence of each of the two DNA strands has been determined for the 0.3, 1.4, 1.5, and 2.2 kb BamHI fragments as depicted below:

```
        10         20         30         40         50         60
GGATCCGGTT GAGGCGGTAA CAGGGGATTG GCATGGCATT GACGAAAGCG GAGATGGCCG 70         80         90        100        110        120
AGCGTCTGTT CGACGAAGTC GGCCTGAACA AGCGTGAGGC GAAGGAATTC GTCGACGCGT 130        140        150        160        170        180
TTTTCGATGT GCTGCCGATG CACTGGAGCA GGGCCGTGCA GGTGAAGTTG TCGGGCTTGC 190        200        210        220        230        240
CGAACTTCGA TCTGCGGCGC AAGAACCAAC GGCCCGGTCG CAATCCCAAG ACCGGTGAGG 250        260        270        280        290        300
AAATTCCGAT CTTGGCCAGG ACGGTGGTGA CCTTCCGCCC CGGCCAGAAA CTCCAAGGAA 310        320        330        340        350        360
CGGGTGGAGG CTTTATGCTG GATCCGGGCA GTAATCGCGA GCTACCGCCG ATTCCGGCCA
```

```
            370        380        390        400        410        420
     AGCGCTACTT CACCATCGGT GAGGTGAGCG AGCTGTGCGA CGTCAAGCCG CACGTGCTGC 430        440        450        460        470        480
     GCTATTGGGA AACCGAATTTT CCGAGCCTGG AGGCCAGTCA AGCGGCGCGC AACCGACGCT 490        500        510        520        530        540
     ACTACCAGCG GCACGATGTC GTGATGGTGC GGCAGATTCG TGGCCTGCTG TACGAGCAGG 550        560        570        580        590        600
     GTTACACCAT CGGGGGCGCG CGTCTGCGTC TTGAAGGGGA TGGGGCCAAG AGCGAGTCAG 610        620        630        640        650        660
     CGCTGAGCAA TCAGATCATC AAGCAGGTGC GCATGGAGCT TGAAGAAGTC CTGCAGCTGC 670        680        690        700        710        720
     TGCGACGCTA GGAAAGCGCC GCATAAAGCC GCTATAATCG CAGGCCGCCT CAGGGCGGGA 730        740        750        760        770        780
     CGCAACATCT TCGGGGTATA GCGCAGCCTG GTAGCGCACT AGTCTGGGGGACTAGTGGTC 790        800        810        820        830        840
     GTCGGTTCGA ATCCGGCTAC CCCGACCAAA CAACAGGCCT ACGTCGCAAG ACGTGGGCCT 850        860        870        880        890        900
     TTTTGTTGCG TCGCAACATG TCAGTTCGAT GGCATTCCAG GCTATGCCAC TATGCGCAAC 910        920        930        940        950        960
     GGCATATTGC AAGGCGGCAT ATGCAAGTCC TGTACGCAAT TATTTCGCGG TTCAGGCTGC 970        980        990       1000       1010       1020
     TACAAGTCGG GATCAGCAGG CGTCCGTAAG TGCCCGGAAA CGCTAGAGTT CGTATGCTGA 1030       1040       1050       1060       1070       1080
     GAATGACGAC CCAGGTCACG TTCTCTTAAC GTCGAGGCGA CGAACTTGAA TCAATAGGCC 1090       1100       1110       1120       1130       1140
     AACGCCGTCA AAAAAATGGC GTGTTGTGCC TTGCGATGTG TTCGTTCTAT GCCATAGTGC 1150       1160       1170       1180       1190       1200
     ACTGCAACAC GCGATTCAAC GTTGGTCCCG GCACGCGTCG GGATGCAACT TCCTGTCGTA 1210       1220       1230       1240       1250       1260
     CGTTCGTGCT GGCGCCTGAG CCGGTTGAAT GCTGCGCGAG GTCCTGTCCC ACCCAACAGA 1270       1280       1290       1300       1310       1320
     GGCAGCCAGC TACACGCATG AAGAAACTGA TCGGACGACT CGTCGCAAGG CCTCAGCCTG 1330       1340       1350       1360       1370       1380
     GCTCTGCTCT GCTCGATGTC GCTGGGCGCT TGCAGCACCG GCCCGGAGAT GGCGTCTTCG 1390       1400       1410       1420       1430       1440
     CTGCCGCATC CGGACCCGCT GGCAATGTCC ACGGTGCAGC CCGAATACCG TCTTGCGCCG 1450       1460       1470       1480       1490       1500
     GGCGATCTGT TGCTGGTGAA GGTGTTTCAG ATCGACGATC TGGAGCGGCA GGTCCGCATC 1510       1520       1530       1540       1550       1560
     GACCAGAACG GTCACATCTC ACTGCCGTTG ATTGGCGACG TCAAGGCCGC CGGTCTGGGC 1570       1580       1590       1600       1610       1620
     GTTGGCGAAC TGGAAAAGCT GGTCGCCGAT CGGTATCGCG CAGGCTACCT GCAGCAGCCG 1630       1640       1650       1660       1670       1680
     CAGATTTCGG TATTCGTGCA GGAGTCCAAC GGGCGTCGCG TCACGGTCAC TGGTGCGGTA 1690       1700       1710       1720       1730       1740
     GACGAGCCGG GCATCTACCC GGTGATCGGC GCCAACCTCA CCTTGCAGCA GGCGATCGCG 1750       1760       1770       1780       1790       1800
     CAGGCCAAGG GTGTCAGCAC GGTGGCAAGC CGCGGCAACG TGATCGTGTT CCGCATGGTC 1810       1820       1830       1840       1850       1860
     AACGGGCAAA AAATGATTGC GCGGTTCGAC CTGACCGAGA TCGAGAAGGG GGCCAATCCG 1870       1880       1890       1900       1910       1920
     GATCCTGAGA TTTATGGCGG CGACATTGTC GTGGTGTATC GCTCGGATGC GCGCGTGTGG 1930       1940       1950       1960       1970       1980
     TTGCGCACCA TGCTGGAACT GACCCCCTTG GTGATGGTGT GGCGCGCTTA CCGATGAGTA 1990       2000       2010       2020       2030       2040
     TGAATTCAGA CAATCGTTCC TCTTCGTCGC AGCGGTCATG GTCATCTGGA ACTGGCAGAT
```

```
        2050       2060       2070       2080       2090       2100
GTCGACTTGA TGGACTACTG GCGCGCCCTG GTCTCGCAGC TCTGGCTGAT CATCCTGATC 2110       2120       2130       2140       2150       2160
GCCGTCGGCG CGCTGTTGCT GGCATTCGGC ATCACGATGT TGATGCCCGA GAAGTACCGC 2170       2180       2190       2200       2210       2220
GCCACCAGCA CCCTGCAGAT CGAACGTGAC TCGCTCAATG TGGTGAACGT CGACAACCTG 2230       2240       2250       2260       2270       2280
ATGCCGGTGG AATCGCCGCA GGATCGCGAT TTCTACCAGA CCCAGTACCA GTTGCTGCAG 2290       2300       2310       2320       2330       2340
AGCCGTTCGC TGGCGCGTGC GGTGATCCGG GAAGCCAAGC TCGATCAGGA GCCGGCGTTC 2350       2360       2370       2380       2390       2400
AAGGAGCAGG TGGAGGAGGC GCTGGCCAAA GCCGCCGAAA GAATCCCGA GGCGGGTAAG 2410       2420       2430       2440       2450       2460
TCGCTCGATT CGCGGCAGGC GATCGTCGAG CGCAGCCTCA CCGATACGTT GCTCGCCGGG 2470       2480       2490       2500       2510       2520
CTGGTGGTCG AGCCGATCCT CAACTCGCGC CTGGTGTACG TCAATTACGA TTCGCCAGAC 2530       2540       2550       2560       2570       2580
CCGGTGCTGG CCGCCAAGAT CGCCAATACG TACCCGAAGG TGTTCATCGT CAGCACCCAG 2590       2600       2610       2620       2630       2640
GAACGCCGCA TGAAGGCGTC TTCGTTTGCG ACACAGTTTC TGGCTGAGCG CCTGAAGCAG 2650       2660       2670       2680       2690       2700
TTGCGCGAGA AGGTCGAAGA CTCTGAAAAG GATCTGGTCT CGTATTCGAC CGAAGAGCAG 2710       2720       2730       2740       2750       2760
ATCGTGTCGG TTGGCGATGA CAAGCCCTCG CTGCCTGCGC AGAATCTGAC CGATCTCAAT 2770       2780       2790       2800       2810       2820
GCGTTGCTGG CATCCGCACA GGACGCCCGG ATCAAGGCCG AGTCAGCTTG GCGGCAGGCT 2830       2840       2850       2860       2870       2880
TCCAGTGGCG ATGGCATGTC ATTGCCGCAG GTGTTGAGCA GCCCGCTGAT TCAAAGCCTG 2890       2900       2910       2920       2930       2940
CGCAGCGAGC AGGTGCGTCT GACCAGCGAG TACCAGCAGA AACTGTCGAC CTTCAAGCCG 2950       2960       2970       2980       2990       3000
GATTACCCGG AGATGCAGCG CCTCAAGGCG CAGATCGAAG AGTCGCGTCG TCAGATCAAT 3010       3020       3030       3040       3050       3060
GGCGAAGTCA TCAATATCCG TCAGTCGCTG AAGGCGACCT ACGACGCCTC CGTGCATCAG 3070       3080       3090       3100       3110       3120
GAGCAGCTGC TCAACGACCG CATCGCCGGT CTGCGGTCCA ACGAGCTGGA TCTGCAGAGC 3130       3140       3150       3160       3170       3180
CGCAGCATCC GCTACAACAT GCTCAAGCGC GAACGTCGAC ACCAACCGCC AGCTCTACGA 3190       3200       3210       3220       3230       3240
TAGCGCTCCT GCAGCGCTAC AAGGAAATCG GCGTGGCGAG CAACGTGGGC GCCAACAACG 3250       3260       3270       3280       3290       3300
TGACCATCGT CGATACCGCA GACGTGCCTA CGTCTAAGAC TTCGCCGAAA CTCAAATTGA 3310       3320       3330       3340       3350       3360
ACCTCGCGTT GGGCCTGATC TTTGGCGTAT TCCTGGGCGT GGCTGTGGCT CTGGTTCGCT 3370       3380       3390       3400       3410       3420
ACTTCCTGCG TGGGCCTTCT CCGAAGTCGC GGTTGAACTG ACATCGTGAT GTTGCAAAAC 3430       3440       3450       3460
GATGGTTAAT TGAAGTGACA ACTGATTCAG CGTGGAAAAG GTGGGATCC
```

The sequence of the 2.2 Kb BamHI fragment is as follows:

```
         10         20         30         40         50         60
GGATCCAGCT TGTATGTGCT CCCGGCCTTG TGGTTTCTCC CCGCACTGTT TGTCGCCACC 70         80         90        100        110        120
GTTGTCTACC TGGCACTGCG CGAAGACCTG AGCGCGCAGT GCTCGCGGTC TGCAGTTTGC
```

```
              130        140        150        160        170        180
     TGGTTGTGTG GGCGTGGACG CGTTGGTTCC CAGGGCTGCG GCTGCGCTTC CGTTTGCACT 190        200        210        220        230        240
     GGATGTGCTG CCGGTCGCGC TGTTCTTCAT TGCAGTCGGC GCATGGCTGT CACGCTTCGC 250        260        270        280        290        300
     AGAGAGAGTG CGCGCGCTTC CTGCGGTCGT TTGGGTCGTC GCGTTCCCGG TCCTGCATTC 310        320        330        340        350        360
     GCCTGGGGGG GCGTTGCAGC CATGAACGGG CAGGTGGATG TCAATAATCT TCAGTTCGGA 370        380        390        400        410        420
     AAATCGTCGC TCCTGTTCCT GATCGCAAGC CTGCTGGGTA CAGCAATGAC GTTGTGCATT 430        440        450        460        470        480
     GCCTACTTCA TGCAAGGGTG GCGCTGGCTG CGTTGGATCG GCGCCAATAC GCTGCTGATC 490        500        510        520        530        540
     CTTGGCACGC ACACGTTGGT GTTTCTGGTC GTGACCAGTG TCGTGGTGCG AACCGGGGTG 550        560        570        580        590        600
     ATCGATCGCA AACTCATCGG TACACCTGTC TGGGCGCTGG CTCTCTGCGC CTTTGCCATC 610        620        630        640        650        660
     GCTGCCTGCA TTCCCATGCG TGCCGTGCTG GTGCGCCGCG CCCTGGATGT TGGGATTGAA 670        680        690        700        710        720
     ACGCAAGTGA GACATTTTCA GAATCATCAG TCGATGTGGC GTGTTCGTGT GAGTCACCGG 730        740        750        760        770        780
     CAAAGGAGAT CGGCGCAATG AAAGTCGTGC ATGTGGTCCG CCAGTTCCAT CCGTCGATCG 790        800        810        820        830        840
     GGGGGATGGA GGAAGTCGTG CTGAACGTGG CACGTCAGCA TCAGGCCAAC AGTGCCGACA 850        860        870        880        890        900
     CGGTTGAGAT CGTCACGTTG GATCGTGTGT TCACCGATCC CTTCGCGCAA CTGGCGCAGC 910        920        930        940        950        960
     ACGAGGTCCA TCAGGGGTTG TCGATCACTC GCATCGGCTA TCGTGGTTCA TCGCGGTACC 970        980        990       1000       1010       1020
     CGATCGCGCC GTCGGTGCTG GGGGCGATCC GTTCGGCGGA CGTGGTGCAT CTGCATGGCA 1030       1040       1050       1060       1070       1080
     TTGATTTTTT CTACGACTAC CTGGCGTTGA CCAAGCCGCT GCACGGCAAG CCGATGGTGG 1090       1100       1110       1120       1130       1140
     TCTCGACGCA TGGCGGGTTT TTCCACACTG CCTATGCGTC GCGCATGAAG CAGATCTGGT 1150       1160       1170       1180       1190       1200
     TCCAGACGCT GACGCGTACT TCTGCGCTGG CCTATGCGCG TGTGATCGCC ACTAGCGAGA 1210       1220       1230       1240       1250       1260
     ATGACGGCGA TCTGTTCGCC AAGGTGGTCG CGCCGTCGCG CTTGCGGGTG ATCGAGAACG 1270       1280       1290       1300       1310       1320
     GTCGTCGACG TGGAGAAGTA TGCAGGGCAG GGCGCTCGAG CGCCGGGACG GACCATGCTG 1330       1340       1350       1360       1370       1380
     TATTTCGGGC GTTGGTCGGT CAACAAGGGC CTGATCGAAA CGCTTGAATT GCTGCAGGCT 1390       1400       1410       1420       1430       1440
     GCGCTCACGC GTGATCCGCA GTGGCGGTTG ATCATCGCCG GGCGCGAGTA CGATTTGAAT 1450       1460       1470       1480       1490       1500
     GAGGCGGATC TGCGCAAGGC CATCGCGAAC GCGGTTTGCA GGACAAGGTG CAGCTGAGCA 1510       1520       1530       1540       1550       1560
     TGTCGCCATC GCAGCAGCAG TTGTGCGCGT TGATGCAGCA GGCGCAGTTC TTCGTGTGCC 1570       1580       1590       1600       1610       1620
     TGTCGCGGCA TGAGGGGTTT GGGATTGCGG CGGTGGAAGC GATGAGCGCG GGGTTGATCC 1630       1640       1650       1660       1670       1680
     CGATTCTCAG CGACATTCCT CCGTTCGTGC GGCTTGCCAC CGAGTCCGGA CAGGGTGTGA 1690       1700       1710       1720       1730       1740
     TCGTCAATCG CGACAGGATT CAGGCCGCGG CCGACAGCGT GCAAGCATTG GCGCTGCAGG 1750       1760       1770       1780       1790       1800
     CCAATGCGGA TTTCGATGCG CGCCGCACGG CGACCATGGC GTATGTGGCG CGCTACGACT
```

```
                1810        1820        1830        1840        1850        1860
          GGCGGCACGT  GGTGGGGCGT  TATATCGACG  AGTACCACGT  GCGCTGGGAA  CACCACGTAC 1870        1880        1890        1900        1910        1920
          GCAGGAGGCC  GTGCGATGAG  CGCGTCTGCT  TCGCTGCCAG  TGACGCGTGC  TGCTGCGGCG 1930        1940        1950        1960        1970        1980
          CCCCGGATCA  CGGTGCTGTT  CTCCACCGAA  AAGCCGAACG  CCAACACCAA  CCCGTATCTC 1990        2000        2010        2020        2030        2040
          ACCCAGCTCT  ACGATCGCTG  CCGGAGCGGT  GCAGCCGCGC  TTCTTTTCGA  TGCGCGAGGC 2050        2060        2070        2080        2090        2100
          GTTGTTGTCG  CGCTACGACG  TGCTGCATCT  GCACTGGCCG  GAATATCTGC  TGCGCCATCC 2110        2120        2130        2140        2150        2160
          CAGCAAGATG  GGCACGCTGG  CCAAGCAGGC  CTGCGCTGCC  TTGCTGCTGA  TGAAGTTGCA 2170        2180        2190        2200        2210        2220
          GCTGACCGGA  ACGCCGGTGG  TACGCACCTT  GCACAACCTG  GCGCCGCATG  AAGACCGCGG 2230        2240        2250        2260        2270
          CTGGCGGAGC  GCGCGCTGCT  GCGTGGATCG  ATCAGCTCAC  GCGGCGCTGG  ATCC

CGCCGGTGG  TACGCACCTT  GCACAACCTG  GCGCCGCATG  AAGACCGCGG
```

The G+C content of Xanthomonas DNA is relatively high (reported in *Bergey's Manual of Systematic Bacteriology*, Vol. 1 (1984) Williams and Wilkins, Baltimore, Maryland, as 65–70 percent). Because of this high G+C content, band compressions on the sequencing gels occur at a relatively high frequency. This problem has been addressed in two ways: (1) the nucleotide sequence is derived for both strands of the DNA so that all sequence can be verified by complementarity of strands and (2) deoxyinosine was substituted for deoxyguanosine to obtain the sequence in areas where band compression was an acute problem. In spite of these measures to avoid errors, the sequence shown above is subject to slight uncertainty due primarily to technical difficulties resulting from the high G+C content of the DNA.

Example 10

This example describes cloning a large segment of *X. campestris* DNA that contains all of the DNA known to encode gum biosynthetic genes.

In order to efficiently transfer the gum gene cluster from *X. campestris* to alternative production organisms, the gum gene cluster was cloned onto plasmid pRK290, described by Titta et al. Proc. Natl. Acad. Sci. USA 77:7347–7351 (1980), specifically incorporated herein by reference. This plasmid vector has a low copy number, a broad host range, and can be conjugally transferred from *E. coli* to a wide variety of gram-negative bacteria. It was found that the restriction enzyme DraI does not cut within any of the cloned *X. campestris* DNA of the gum region, however it does cut several times within the lambda cloning vector used in construction of the *X. campestris* gene bank. Cleavage of recombinant bacteriophage DNA with DraI, therefore, generated several DNA fragments, one of which contains the entire *X. campestris* insert and a relatively small amount of lambda DNA (approximately 3 kb) fused on each end. Therefore, it was decided to choose a lambda recombinant that contains all the *X. campestris* DNA believed to contain gum genes, to purify a large quantity of that phage DNA, to digest the DNA with DraI, and to purify and subsequently clone the restriction fragment that contains the *X. campestris* insert DNA.

Upon isolation of each lambda phage carrying gum gene DNA, a BamHI restriction map was constructed for each phage. As a result of the mutational analysis, a picture developed of which segments of cloned DNA carried gum genes. It was concluded that lambda 655(L'), shown in FIG. 2, contained the intact gum gene cluster. Therefore, this phage was chosen for initial cloning efforts. Using standard techniques, a large-scale (1 liter) lysate of lambda 655(L') was prepared. This lysate yielded a total of approximately $8\times10^{11}$ phage particles. The phage particles were purified by polyethylene glycol precipitation and CsCl density gradient centrifugation. Phage DNA was extracted from the virions, and a yield of approximately 225 ug was obtained.

Approximately half of the purified lambda 655(L') DNA (120 ug) was treated with EcoRI methylase and BamHI methylase. These enzymes recognize and modify, i.e., methylate, the nucleotide sequences recognized and cleaved by the corresponding restriction endonucleases. Methylation renders the sequence resistant to cleavage by the endonuclease. Methylation allows use of BamHI or EcoRI oligonucleotide linkers on the ends of the DraI fragments, which are blunt and therefore poor substrates in ligation reactions. The success of the methylation reaction is monitored by analyzing subsequent resistance of lambda 655(L') DNA to cleavage by EcoRI and BamHI. The methylated DNA was not perceptibly cleaved by an approximately 20× excess of each enzyme in a 2-hour digestion.

Roughly 100 ug of methylated DNA was then digested to completion with DraI, and approximately 80 ug of this DNA was then reacted in a ligation with an 8 bp BamHI oligonucleotide linker. The linker is a small double-stranded, blunt-ended DNA which is ligated onto the blunt DraI ends in a reaction using high DNA concentrations and approximately 100× molar excess of linker fragment over DraI lambda 655(L') fragment. The ligated linker fragments can subsequently be cleaved with BamHI to generate sticky ends suitable for cloning into BamHI-cut vector DNA. However, prior to BamHI digestion, the DNA is fractionated by sedimentation through a sucrose gradient. The purpose of fractionation over sucrose is two-fold. First, a large enrichment of the 20 kb fragment can be achieved, although the resolution of sucrose gradient sedimentation will not afford absolute purification of the 20 kb fragment away from the other DraI fragments. Second, the unligated BamHI linker molecules can be eliminated, because these small DNA segments essentially do not enter the gradient. Thus, the gradient fractions containing the 20 kb DraI fragment will be, for practical purposes, completely free of linker DNA. This is important because the linker DNA can potentially interfere with subsequent digestion and/or ligation steps. The DraI digest was centrifuged through a 5 ml 5% to 20% sucrose gradient. Fractions (approximately 250 ul) were collected and analyzed by running an aliquot of each fraction on an agarose gel. Fractions containing the bulk of the 20 kb DraI fragment were pooled, ethanol precipitated, resuspended in buffer, and stored for future use.

The 20 kb DraI fragment was then digested with BamHI in order to cleave the attached linker molecules and generate single-stranded DNA ends suitable for cloning. The plasmid pRK290 was digested with BqlII, which generates single-stranded DNA ends identical to the BamHI ends. The ligation reaction was carried out in 50 mM Tris-HCl (pH 7.8), 10 mM MgCl$_2$, 20 mM dithiothreotol, and 1.0 mM ATP. The 20 ul reaction contained 0.2 ug of pRK290 (digested with BglII) and 0.1 ug of 20 kb DraI fragment (digested with BamHI) and was catalyzed by T4 DNA ligase (6 Weiss units). The reaction was allowed to proceed overnight (approximately 18 hours) at 12° C.

The products of the ligation reaction were then used to transform E. coli. Tetracycline-resistant transformants were selected and then screened for the presence of recombinant plasmids containing the cloned gum gene cluster. This screening was accomplished by mating individual tetracycline-resistant transformants with a X. campestris strain containing a Gum⁻ mutation (within the gum gene cluster), selecting for conjugal transfer of the tetracycline resistance into X. campestris and visually assessing the resulting Gum phenotype. Most matings produced Gum⁻ Tet$^r$ X. campestris, but a small number yielded $Tet^r$ colonies that appeared very mucoid. Analysis of plasmids carried by *E. coli* plasmid donors in these matings revealed the presence of recombinant plasmids comprised of pRK290 and the inserted gum gene cluster DNA.

Five recombinant plasmids have been analyzed. Purified plasmid DNA's were prepared by CsCl density gradient centrifugation and analyzed by BamHI digestion and agarose gel electrophoresis. The restriction fragments generated were compared to the BamHI digestion products of lambda 655(L'). The vector pKR290 has no BamHI sites (the DraI fragment, carrying BamHI linkers on its ends, was cloned into a BqlII site) and the lambda 655(L') phage contains no BamHI sites outside the cloned *X. campestris* DNA. Therefore, the BamHI digests should produce identical sets of *X. campestris* DNA fragments. However, only two pRK290 derivatives (H627 and H806) contained all of the BamHI fragments found in lambda 655(L'). The other three recombinants each contained a unique and contiguous subset of these BamHI fragments. The most likely explanation for these truncated clones is that the methylation of BamHI sites (a step in preparation of the DraI fragment for cloning) was incomplete. That is, a small fraction of the BamHI sites were not methylated and therefore not protected against the subsequent BamHI digestion used to cleave the attached linkers. If, for example, 5% of the BamHI sites were unprotected, then 40% of the DraI fragments would contain an unmethylated BamHI site. The subsequent BamHI digestion would cleave these sites and produce a family of truncated fragments that could be cloned in pRK290. The assay of BamHI methylation used to check the initial reaction would not have detected a 5% level of unmethylated BamHI sites. The incomplete clones probably arose as described above. In any event, the structures of the five clones obtained are shown in FIG. 9.

Example 11

This example shows, through the use of immunologic assays, that the enzymes encoded by the gum biosynthetic cluster were present only in small quantities in *X. campestris*.

Proteins were displayed through the technique of two-dimensional electrophoresis. Wild-type *X. campestris* was compared to a *X. campestris* strain unable to synthesize a sugar nucleotide precursor, but which was able to synthesize xanthan in vitro. These two strains contain gum biosynthetic enzymes. The protein proposed to be UDP-glucose dehydrogenase was missing in the pattern of the second strain. An *X. campestris* strain deleted for the entire gum biosynthetic cluster was also analyzed. Several proteins were missing from extracts of the deletion strain. The intensity of the spots proposed to correspond to the gum biosynthetic enzymes was very low.

Additional data are provided. An insertion mutation in the central portion of the 2.2 kb BamHI fragment produces a $Gum^-$ mutant which is defective in Transferase III activity. This insertion is located at the BqlII site approximately at position 1132 in the DNA sequence of the 2.2 kb BamHI fragment. The DNA sequence indicates that a large open reading frame (ORF) is present in this region of the sequence. The putative protein product having Transferase III activity begins with the ATG start codon at approximately position 738. Eight base pairs upstream from the start codon is a ribosome binding site (AGGAGA). The ORF clearly extends well beyond the BqlII site where the insertion mutation defining the Transferase III activity is located.

Peptides corresponding to several regions of the predicted protein sequence were selected for their predicted immunogenicity by a hydrophilicity plot known to those in field and developed by Hopp and Woods and described in the article entitled "Prediction of Protein Antigenic Determinants from Amino Acid Sequences," Proc. Natl. Acad. Sci. USA, Vol. 78, No. 6, pp. 3824–3828, June 1981, specifically incorporated herein by reference. The peptides chosen and their location within the 2.2 kb BamHI fragment are shown in Table 2.

TABLE 2

Peptides chosen from the 2.2 kb BamHI fragment for antisera production.

| Approximate location in 2.2 kb fragment (first bp) | Synthetic Peptides (13 residues) | | | | | | | |
|---|---|---|---|---|---|---|---|---|
| 807 | A. | Val | Ala | Arg | Gln | His | Gln | Ala |
| | | Asn | Ser | Ala | Asp | Thr | Val | |
| 930 | B. | Arg | Ile | Gly | Tyr | Arg | Gly | Ser |
| | | Ser | Arg | Tyr | Pro | Ile | Ala | |
| 1041 | C. | Leu | Ala | Leu | Thr | Lys | Pro | Leu |
| | | His | Gly | Lys | Pro | Met | Val | |
| 1632 | D. | Asp | Ile | Pro | Pro | Phe | Val | Arg |
| | | Leu | Ala | Thr | Glu | Ser | Gly | |
| 1677 | E. | Val | Ile | Val | Asn | Arg | Asp | Arg |
| | | Ile | Gln | Ala | Ala | Ala | Asp | |
| 1740 | F. | Ala | Asn | Ala | Asp | Phe | Asp | Ala |
| | | Arg | Arg | Thr | Ala | Thr | Met | |

The peptides were synthesized by solid-phase peptide synthesis, conjugated to bovine serum albumin and used to immunize rabbits. After four immunizations, the hyperimmune sera were found to contain respectable titers of antibodies specific to the immunizing peptides by ELISA (enzyme-linked immunosorbent assay) widely used in the field and herein referenced Eva Engvall, Methods in Enzymology, Vol. 70, pp. 419–439, 1980, "Enzyme Immuno-Assay ELISA and EMIT".

These specific antibodies also reacted with a 40 kd protein encoded by the 2.2 kb BamHI fragment on Western immunoblots as described by Towbin, H., Staehelin, T. and Gordon, J. in "Electrophoretic Transfer of Proteins from Polyacrylamide Gels to Nitrocellulose Sheets: Procedure and Some Applications," Proc. Natl. Acad. Sci. USA 76:4350–4354 (1979), specifically incorporated herein by reference, of cell lysates of *X. campestris* S4-L. The protein was not present in cell lysates of X1107, the strain with the gum cluster DNA deleted, or X928, a strain with a mutational insertion in the 2.2 kb BamHI fragment. This 40 kd protein is not visualized in S4-L by the less sensitive method of direct staining of protein in the gel with Coomassie blue; thus, this gum biosynthetic protein is a very small percentage of the total cell protein. It appears that low expression of the gum biosynthetic proteins is sufficient for xanthan gum production in S4-L.

Example 12

This example discusses the specific sugar nucleotide pools identified in various *X. campestris* strains that are Gum⁻ in vivo, and in bacteria contemplated as alternative hosts.

Several Gum⁻ strains were able to make xanthan in vitro when supplied with the sugar nucleotides UDP-glucose, GDP-mannose, and UDP-glucuronic acid. These mutants were defective in sugar nucleotide synthesis, rather than biosynthesis of xanthan itself. Subsequently, such mutants were found to be sensitive to the dye toluidine blue. Additional sugar nucleotide mutants were obtained by screening other $Gum^-$ strains for toluidine blue sensitivity.

The following method was employed to identify the specific sugar nucleotide defects in strains which were Gum+ in vitro but $Gum^-$ in vivo. An isolated colony from each strain was picked and inoculated into 10 ml YM broth (3 g yeast extract, 3 g malt extract and 5 g peptone per liter) with 2% glucose in a 125 ml Erlenmeyer flask. Cultures were incubated at 30° C., 250 rpm, for 24 hours or until turbid. Five percent inocula were transferred from YMG broth into mineral salts medium with glucose as the carbon source and allowed to grow at 30° C. for 24 hours. Cultures were harvested by centrifugation, washed twice with salts, and resuspended in a volume to sufficient to give an absorbance at 600 nm of 100. Samples, 1.5 ml, were placed in 50 ml Erlenmeyer flasks containing sufficient glucose to bring the concentration to 20 mM. Each sample was incubated in a 30° C. water bath at 400 rpm for ten minutes, then 1 ml was removed and added to 0.1 ml of 11N formic acid in an Eppendorf centrifuge tube. The tube was capped, the contents mixed for 5 seconds on a vortex mixer, then the tube was placed in a dry ice-alcohol bath. After all samples had been processed, the tubes were removed from the dry ice bath, thawed at room temperature, and centrifuged for 5 minutes to pellet the cell debris. The supernatants were placed in prechilled 15 ml conical centrifuge tubes and frozen in a dry ice-alcohol bath again. Frozen samples were placed on a lyophilizer and taken to dryness. The contents of each tube were dissolved in 0.2 ml HPLC buffer, 40 mM phosphoric acid adjusted to pH 6.5 with triethylamine (Aldrich). Samples were filtered through 0.45 um filters into microsample vials, then analyzed by injection onto a 4.6 mm×250 mm C18 reverse phase ion pair column, 40° C., flow rate of 0.8 ml per minute. Sugar nucleotides were identified by comparing retention times to those of standards run under the same conditions, and by examining the spectra of compounds eluting in the region of interest.

Four classes of sugar nucleotide mutants of *X. campestris* were identified using this procedure:

(1) mutants unable to synthesize UDP-glucose and UDP-glucuronic acid;

(2) mutants unable to synthesize GDP-mannose;

(3) mutants able to synthesize UDP-glucose but not UDP-glucuronic acid; and (4) mutants unable to synthesize UDP-glucose, GDP-mannose, and UDP-glucuronic acid.

Extracts from wild-type strains of *X. campestris* had all of the sugar nucleotides required by xanthan biosynthesis. $Gum^-$ mutants defective in the xanthan biosynthetic pathway itself had higher concentrations of the precursor sugar nucleotides than did wild-type cells. These data indicate that the rate of xanthan synthesis in wild-type cultures may be limited by the supply of precursor sugar nucleotides.

The sugar nucleotides in *Paracoccus denitrificans* (ATCC 17741), *Pseudomonas stutzeri* (ATCC 17588), and *Pseudomonas perfectomarina* (ATCC 14405) were analyzed using procedures developed for *X. campestris*. All organisms were grown for twelve hours in DENITE medium, a mineral salts medium, with two percent glucose as the carbon source. Cells were collected, washed, and resuspended to an absorbance at 600 nm of 100. The cell pellets had a pink hue typical of denitrifying bacteria which have derepressed synthesis of the cytochromes required for anaerobic growth (a typical response to oxygen limitation during growth). Consequently, 25 mM nitrate was included as an additional electron acceptor in the incubation mixtures. Cell suspensions were incubated with 20 mM glucose for five minutes with and without nitrate, then extracted with formic acid. Extracts were lyophilized, dissolved in TEA-phosphate buffer and analyzed by HPLC. *Paracoccus denitrificans* had UDP-glucose and GDP-mannose, but undetectable amounts of UDP-glucuronic acid, as verified by spectra of peaks in the regions of interest. Similarly, *Pseudomonas perfectomarina* and *Pseudomonas stutzeri* had UDP-glucose and GDP-mannose. UDP-glucuronic acid was not detected in extracts from either organism.

Example 13

This example shows that several gum biosynthetic enzymes have been expressed in the alternative host *E. coli.*

Many gum cluster DNA fragments have been cloned in the expression vector pp3, which was engineered from the plasmid pKO-1. That plasmid was described by K. McKenny et al. in Gene Amplification and Analysis, Volume II Elsevier, North Holland, p. 383, 1981, specifically incorporated herein by reference.

The 2.2 kb BamHI fragment of the gum cluster encoding Transferase III was cloned into pp3, resulting in pJP1. *E. coli* JM105 transformed with pJP1 was cultured in rich medium, induced with IPTG ($10^{-3}$M) and harvested by centrifugation after 3 hours at 37° C. A cell lysate was prepared by two passes through a French pressure cell at 18,000 psi and run on a 10% SDS-acrylamide gel to separate the proteins by molecular weight. These proteins were probed with antibodies specific to Transferase III by the Western immunoblot technique. The cell lysate of JM105(pJP1) showed a distinct band of the 40 kd protein. The similarly-treated *E. coli* cell lysate with pp3 without an insert did not have the 40 kd protein. Even in the JM105(pJP1) cells induced by IPTG, the 40 kd protein from the *X. campestris* cloned DNA was not visible by Coomassie blue staining and thus was a small percentage of the total cell protein. When the electroblots of E. coli JM105 (pJP1) were probed with affinity-purified antibodies, the antibodies reacted singularly with Transferase III. The gum biosynthetic gene was unequivocally expressed in E. coli JM105.

Further evidence is given by the expression of fragments of the gum biosynthetic DNA cluster cloned into pp3 which were used to transform E. coli FD1098 (F'lacI$^Q$). FD1098 is a strain that gives off, by an unequal cell division, minicells which do not contain chromosomal DNA but do contain copies of the pp3-derived plasmids. The use of minicells to analyze gene expression is described by J. E. Clark-Curtiss and R. Curtiss III in Methods in Enzymology 101:347–362 (1983), specifically incorporated herein by reference. After the minicells have been separated from whole cells by centrifugation through a series of sucrose gradients, the minicells are induced with IPTG and they are radiolabeled while expressing proteins encoded by the pp3-derived plasmid. The minicells are harvested, run out on 10% SDS-acrylamide gels, and the expressed proteins are visualized by autoradiography.

The gum biosynthetic DNA clearly encoded several proteins that were visualized by this method. A protein of 40 kd was again seen in E. coli, and it was dependent on the presence of the 2.2 kb BamHI fragment. A protein of 47 kd molecular weight was encoded by the 3.5 kb BamHI fragment. A protein of 27 kd is encoded by the X. campestris DNA spanning the 3.5 and the 1.35 kd BamHI fragments. The evidence for other gum biosynthetic proteins in E. coli minicells is tentative. The expression of gum cluster DNA is low in the alternate host E. coli*, as is true in *X. campestris.*

Example 14

This example contemplates the means for achieving gene expression in an alternative host.

It is conceivable that the gum cluster of biosynthetic genes, when introduced into an alternative host, will be either transcriptionally silent or translationally silent. It is conceivable also that some, but not all, of the biosynthetic genes will be expressed. With nucleic acid probes and antibodies directed against the proteins encoded by the gum cluster, transcription and translation of all genes within the cluster will be measured.

If some or all of the genes are not transcribed, regulatable promoters will be added to the cluster in appropriate locations. The RNA polymerases of the eubacteria are very similar, including those from Gram-negative and Gram-positive species. The DNA sequences that permit initiation of transcription are sufficiently understood for one familiar with the art to introduce such promoters with ease.

Similarly, both Gram-positive and Gram-negative ribosome binding sites (which are used to initiate translation) are understood sufficiently to achieve translation of any mRNA which has been transcribed. Using standard methods of site-directed mutagenesis, any gum cluster enzyme that is inappropriately expressed relative to its expression in wild-type *X. campestris* will be adjusted for correct output in the alternative host.

Example 15

This example describes increased thermo-stability of gum biosynthetic enzymes.

The present invention contemplates the use of organisms that grow above 30° C. as potential alternative hosts. Xanthan biosynthesis occurs optimally in *X. campestris* at temperatures between 27° and 30° C. If the enzymes involved in gum biosynthesis do not function well above 30° C. but are expressed, the enzymes will be altered to thermo-stable variants as described in Liao et al. in U.S. patent application Ser. No. 793,475 entitled "Method for the Generation and Detection of Enzyme Variants with Enhanced Thermostability and Activity," filed Oct. 28, 1985 as a continuation of U.S. patent application Ser. No. 532,765, filed Sep. 16, 1983, specifically incorporated herein by reference. Single amino acid substitutions in a protein can raise the maximum temperature at which an enzyme functions by more than 10° C. The gene sequences described herein readily permit such replacements.

Example 16

This example describes additional improvements that will allow alternative hosts to synthesize polysaccharides.

Alternative hosts containing the gum biosynthetic genes, and capable of transcription and translation of those genes, may fail to produce polysaccharide at all or at a significant rate.

The first experiments, if this occurs, will address the abundance and potential synthetic rate of the sugar nucleotide precursors (UDP-glucose, UDP-glucuronic acid and GDP-mannose). Cloned genes for the key enzymes of the sugar nucleotide pathways are available from *X. campestris* using methods described by Betlach et al., supra. If a particular sugar nucleotide pool is too low for adequate polysaccharide production, the appropriate *X. campestris* genes will be added to the alternative host. The alternative host may then yield adequate polysaccharide, or the rate may remain low.

If the rate of polysaccharide synthesis remains low, the second improvement will be attempted by surveying all other regions of the *X. campestris* genome for genes that allow the gum gene cluster and, if required, the sugar nucleotide pathway, to function so as to produce polysaccharide. A library of *X. campestris* genomic fragments as constructed in Example 3 of ca. 20,000 base pairs in length will be conjugally added by standard techniques as described by Titta et al. to the alternative hosts that have all of the gum cluster genes and sugar nucleotide genes but are still not making polysaccharide. Recipients of this library will be observed on petri plates for mucoid colonies; bacterial colonies that produce polysaccharide are easily distinguished from those that do not. Even when crowded, petri plates with $10^3$ bacterial colonies are easily observed. Only a small number of recipients must be observed (less than $10^3$) to see whether any other gene cluster present on an *X. campestris* DNA fragment will provide a missing gene product required for polysaccharide production.

If this experiment fails to yield a polysaccharide producer, the entire collection of recipient alternative hosts (now containing the well-expressed gum biosynthetic genes, the missing sugar nucleotide enzymes, if necessary, and a random collection of 20,000 base pair DNA fragments from *X. campestris* ) will be mutagenized with chemicals that cause base-pair substitutions (such as, but not exclusively, nitrosoguanidine, 2-aminopurine or ethylmethane sulfonate). Mutagenized bacteria will be plated on agar medium so as to observe mucoid colonies. Mucoid colonies have been found as very rare revertants of some transposition-induced Gum$^-$ mutations of *X. campestris*. More than $10^8$ mutagenized colonies of any given alternative host will be screened for polysaccharide production.

The choices of alternative hosts need not be restricted to a few best candidates. Plasmid pRK290-H336 has a broad host range and can be conjugally moved to a large number of potential alternative production strains. Similar constructs carrying the sugar nucleotide biosynthetic enzyme(s) will be made so that many alternative hosts can be tried. Thus far, pRK290-H336 has been placed within the potential production strains *Pseudomonas putids, Pseudomonas cepacis, Pseudomonas denitrificans, Pseudomonas fluorescens, Pseudomonas stutzeri, Escherichia coli,* and *Enterobacter cloacae.*

One strategy for alternative host selection would be to select a bacterium that is known to be capable of extracellular polysaccharide biosynthesis. Such strains can easily be mutated to incapacitate the endogeneous polysaccharide biosynthesis before pRK290-H336 is incorporated into the strain. Such strains could contain important gene products that must interact with the *X. campestris* gum biosynthetic enzymes and/or biosynthetic intermediates in order to facilitate polysaccharide synthesis and secretion. Since the plasmid transfer experiments are so straightforward, hosts with widely varying capacities to make a gum will be tried.

The proposed invention contemplates an alternative host, producing polysaccharide, within which reside the gum gene cluster of biosynthetic enzymes, the genes which provide for the biosynthesis of the appropriate sugar nucleotides and a random *X. campestris* DNA fragment. In addition, the strain may contain a number of base pair substitution mutations from the last step of the strain improvement. The alternative host will be successively cured, by standard techniques, of the random *X. campestris* DNA fragment and the sugar nucleotide biosynthetic gene. If polysaccharide production remains unchanged, these DNA fragments will not be used in the alternative host production strains.

Example 17

This example describes the derivation of the nucleotide sequence for a 16 kb stretch of Xanthomonas genomic DNA which contains a cluster of genes involved in xanthan gum biosynthesis. A portion of the DNA sequence (i.e., the sequence of the 0.3, 1.4, 1.5, and 2.2 kb BamHI fragments) that is presented here was previously described in the patent application of Capage et al. entitled "Recombinant-DNA Mediated Production of Xanthan Gum" filed Mar. 26, 1986. The previous sequence has been modified (corrected) by more recent results which were derived from sequencing reactions that utilized deoxyinosine to resolve areas of band compression on the sequencing gels. This example also shows how appropriate analysis of the DNA sequence reveals the structure and organization of the gum genes.

The complete nucleotide sequence for the entire 16 kb segment of DNA is presented in a double-strand format in FIG. 10. The top strand of the sequence reads 5' to 3' in the left-to-right direction of the BamHI restriction map shown in FIG. 4. The computer technique (frame analysis) described by Bibb et al. in Gene 30:157–166 (1984), specifically incorporated herein by reference, was used to determine the G+C distribution at each of the three nucleotide positions that define the three possible reading frames of the sequence in each direction. These frame analysis results showed that all of this DNA is transcribed in the left-to-right direction. Thus, the top strand of the sequence shown in FIG. 10 is the coding strand sequence (i.e., the sequence of the mRNA with T substituted for U). The exact location of the genes defined by the sequence can be obtained from data that is shown in Table 3.

TABLE 3

Location and characteristics of the gene proteins within the DNA of the gum gene cluster

| Protein | BamHI Fragment | Location (BP number) Beginning | End | Reading Frame | Mutant Phenotype | Function | Molecular Wt. (kD) |
|---|---|---|---|---|---|---|---|
| gpA | 0.3 and 1.4 | 33 | 669 | 3 | Gum$^+$ | — | 24.4 |
| gpB | 1.4 and 1.5 | 1336 | 1975 | 1 | No charger (lethal) | Not Known | 23.3 |
| gpC | 1.5 | 2050 | 3181 | 1 | No charger (lethal) | Not Known | 42.8 |
| gpD | 4.7 | 3644 | 5096 | 2 | No charger | Not Known | 54.6 |
| gpE | 4.7 | 5181 | 6477 | 3 | Lethal | Not Known | 48.3 |
| gpF | 4.7 | 6476 | 7568 | 2 | No acetylation | Acetylase | 39.9 |
| gpG | 4.7 and 2.2 | 7567 | 8704 | 1 | Mucoid Gum$^+$ | Not Known | 42.0 |
| gpH | 2.2 | 8703 | 9843 | 3 | Cellobiose | Transferase III | 42.1 |
| gpI | 2.2 and 3.5 | 9842 | 10889 | 2 | No charger | Putative Transferase I | 38.9 |
| gpJ | 3.5 | 10909 | 12382 | 1 | Possibly Lethal | Not Known | 52.9 |
| gpK | 3.5 | 12764 | 13649 | 2 | Trimer | Transferase IV | 32.4 |
| gpL | 1.35 | 13693 | 14485 | 1 | No pyruvylation | Ketalase | 29.3 |
| gpM | 1.35 and 1.0 | 14495 | 15284 | 2 | Glucose | Transferase II | 28.6 |

Finally, the successful alternative host will be used in combination with those mutations in the gum biosynthetic cluster that cause synthesis of variant polysaccharides. Thus, the alternative host, with its combination of advantages from metabolic rate, growth temperature, and anaerobic metabolism, will be used to make xanthan and the xanthan variants of Vanderslice et al. and Doherty et al. and any other exopolysaccharide.

An overview of the organization and structure of the genes contained in the 16 kb segment of DNA is presented in FIG. 11. The top line in the figure is a BamHI restriction map and indicates the location of each of the BamHI restriction sites in the sequence shown in FIG. 10. In FIG. 11, the line drawn above the frame analysis curves shows the approximate position of some of the mutations that have been isolated and characterized (examples 1, 2, 7, 19, 20).

The frame analysis curves presented in FIG. 11 show the distribution of G+C content at the first (blue line), second (red line), and third (black line) nucleotide positions. Note that the distribution of G+C content at the three nucleotide positions is non-random throughout most of the entire sequence, indicating that virtually all of this DNA codes for protein products. Each area of non-random G+C distribution along the sequence predicts regions of the DNA that code for protein products. The reading frame of each protein is defined by the nucleotide position having an intermediate value within each region of non-random G+C distribution. The points where the G+C distribution at the three nucleotide positions change predict either the beginning or end of a gene or the end of one gene and the beginning of the next. In each case, these points were found to correlate with the presence of either a start or stop codon in the appropriate reading frame.

Below the frame analysis curves, separate arrows are drawn to indicate the location and extent of each gene in the sequence. For convenience, each gene is designated with a letter, and that letter preceded by "gp" is used to designate its protein product. Above each arrow, the molecular weight of the protein product is shown in kD. Below each arrow, the name of each gene product is shown as its lettered name as well as its functional name for those cases where gene function could be derived from the mutant phenotype.

Figure 13:
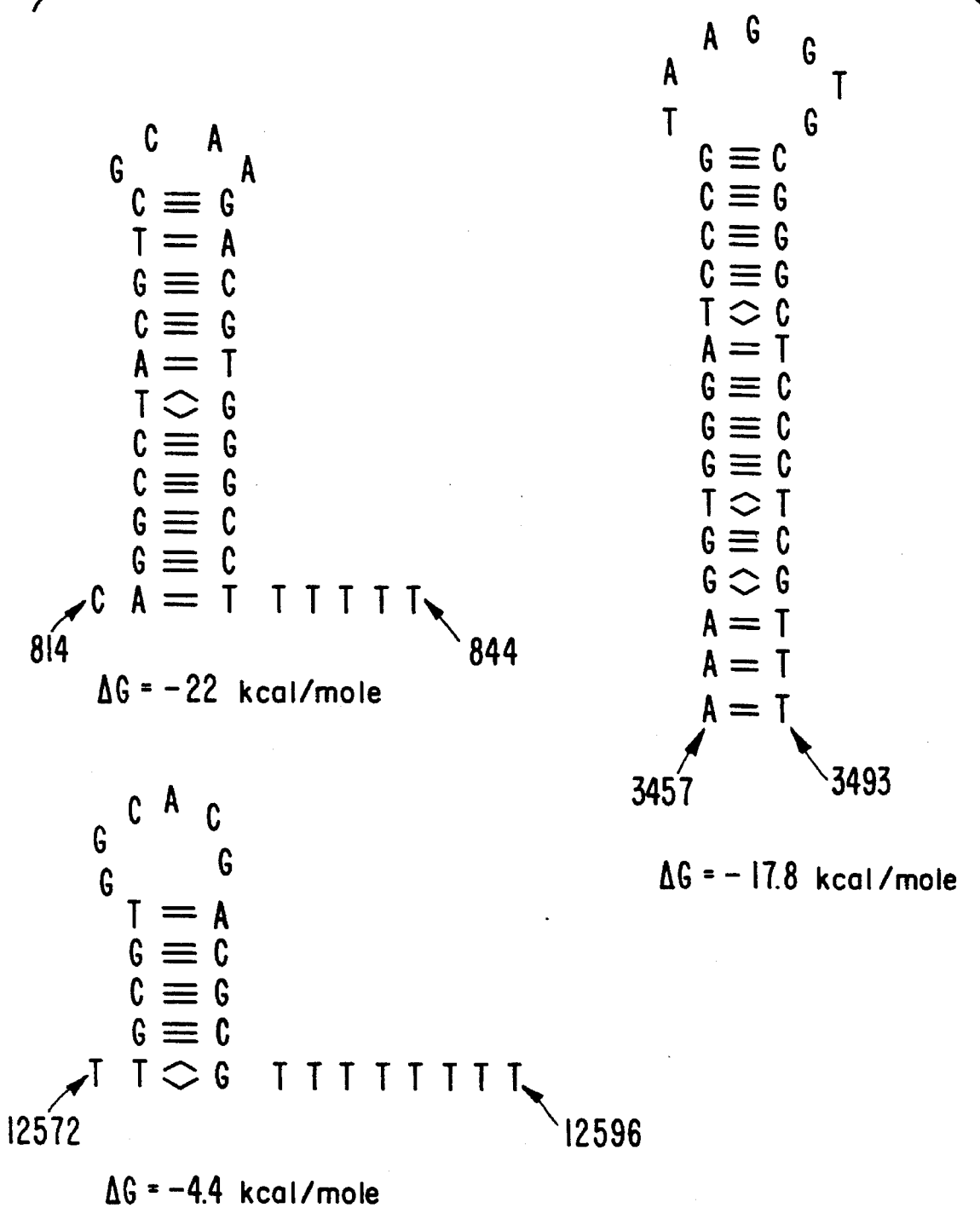
Figure 14:
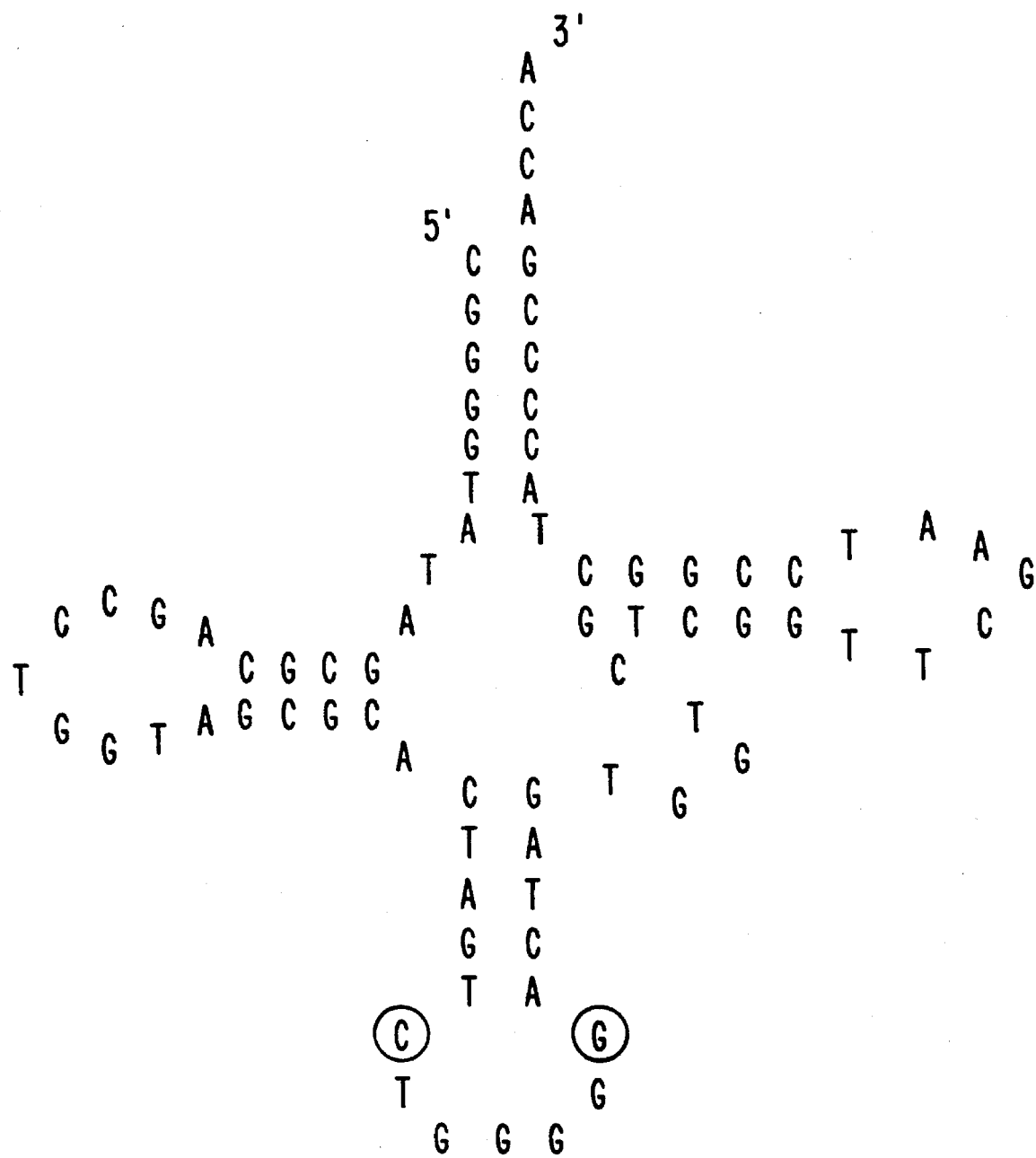

The frame analysis curves indicate that there were three areas of the sequence (centered at base numbers 900, 3400, and 12400) where the G+C content at each of the three nucleotide positions shows a random distribution. Hence, these three areas of the DNA were not expected to code for protein products. All three of these areas contain a transcription termination signal as defined by an area of sequence containing a run of T's that is preceded by a GC-rich region that forms a stem-loop secondary structure. The secondary structure of these terminators is shown in FIG. 13. Based on the location of the transcription terminators, the DNA of the 16 kb segment is delimited into three transcription units. The arrows at the bottom of FIG. 11 show the extent, location, and direction of transcription for each of the three units which are designated as transcription units I, II and III.

The DNA sequence between each terminator and the beginning of the first gene within each transcription unit should contain a sequence (promoter) which specifies the point of transcription initiation. Since results reported in the literature indicate that the sequence of at least some Pseudomonad promoters bears a resemblance to the sequence of *E. coli* promoters, the appropriate regions of DNA sequence within each of the three transcription units were examined for homology to the consensus sequences of *E. coli* promoters at both the −10 (Pribnow Box) and −35 positions. It is generally believed that the sequence of the Pribnow Box is the most important of these two sequences in specifying the binding of RNA polymerase to the DNA to initiate transcription. The consensus sequences of the Pribnow Box and the −35 hexamer are TAtaaT and TTGAca, respectively (capital letters designate the highly conserved nucleotides of each hexamer). Thus, a minimum criterion for defining a putative promoter is the presence of a hexamer having the sequence TANNNT ("N" is any nucleotide).

Transcription units I and III were found to contain putative promoters (at positions 1199 and 12664, respectively) that satisfied only the minimum criterion, i.e, homology with the first, second, and sixth nucleotides of the Pribnow Box. Thus, the location of the putative promoters for these two transcription units is very tentative. Transcription unit II contained a putative promoter (around position 3580) having a sequence bearing striking homology to the consensus sequence of *E. coli* promoters. The sequence of the Pribnow Box shows homology with four out of the six nucleotides, including the three that are highly conserved. The sequence of the −35 hexamer shows homology with five out of six nucleotides, including the four that are highly conserved. The distance between the two hexamers is 16 base pairs, in perfect agreement with the consensus distance of 16 to 19 base pairs. Thus, although it is not possible to unequivocally identify a promoter from sequencing data alone, it seems highly probable that the putative promoter for transcription unit II is correct.

The data presented in FIGS. 10, 11, and 12 and Table 3 (taken together) show a unified picture of the structure and organization of the gum genes as well as provide an easily accessible source of specific information. For example, FIG. 11 shows that there is an insertion mutation in the 4.7 kb BamHI fragment that generates mutant Xanthomonas cells that produce non-acetylated gum. The mutation is located around position 7000 of the DNA sequence in a region containing a frame 2 ORF that defines a protein product (gpF) having a moleculer weight of 39.9 kD. The exact position of the gene within the DNA sequence is shown in Table 3. This information can be used to locate the DNA sequence of the gene in FIG. 10. FIG. 11 shows that the gene is located within transcription unit II and probably functions as the acetylase enzyme. The predicted amino acid sequence of the acetylase enzyme is shown in FIG. 12 along with additional data that indicate that the enzyme contains a high proportion of hydrophobic amino acid residues that are distributed throughout the protein sequence. Therefore, the acetylase enzyme probably functions in the bacterial membranes.

The region of the DNA sequence which begins with the first nucleotide at the left-hand BamHI site of the 0.3 kb BamHI fragment and extends to the transcription terminator around position 800 is DNA that appears to lie outside of the region of the Xanthomonas chromosome that contains genes involved in gum biosynthesis. The DNA sequence in this area shows that there is a frame 3 ORF that spans the BamHI site that delimits the 0.3 and 1.4 kb BamHI fragments. The ORF defines a protein product (gpA) having a molecular weight of 24.4 kD. Insertions into the BamHI site that are located within the gene produce Xanthomonas cells with a $Gum^+$ phenotype. Thus, gpA appears to be the final gene in a transcription unit that begins somewhere to the left of the 0.3 kb BamHI fragment in a region of the Xanthomonas chromosome containing genes that are not involved in gum biosynthesis.

The region of DNA sequence between the end of gpA and the transcription terminator was found to contain a proline tRNA gene. The folded secondary structure of this tRNA transcript is shown in FIG. 14. The G and C nucleotides at the top of the anticodon loop (shown circled in FIG. 14) would probably preclude the functioning of this tRNA in translation. Chromosomal deletions which completely remove this tRNA gene as well as the entire gum gene cluster and insertions into the anticodon loop produce Xanthomonas cells that are viable but $Gum^-$ in the case of deletions and $Gum^+$ in the case of insertions. Thus, this proline tRNA gene is not essential for viability or gum biosynthesis.

The frame analysis curves (FIG. 11) for the area of the DNA sequence contained within transcription unit I indicate that this region of the Xanthomonas chromosome contains a large frame 1 ORF. The location of start and stop condons (Table 3) shows that the ORF contains two proteins (gpB and gpC) having molecular weights of 23.3 and 42.8 kD, respectively. Initial results from studies done to characterize mutant Xanthomonas strains containing Tn10 insertions within the 1.4 and 1.5 kb BamHI fragments showed that both of these proteins exhibited a "no charger" mutational phenotype. However, thse results were ambiguous since Southern blots of the chromosomal DNA from the mutant strains clearly indicated that the DNA had undergone a rearrangement. More recent results from complementation experiments showed that deletion of the 1.5 kb BamHI fragment was lethal in Xanthomonas cells. The Xanthomonas mutant X1231 contains a deletion of the entire 16 kb segment of DNA (which includes the 1.5 kb BamHI fragment) and, although the strain is Gum⁻, it remains fully viable. Thus, gpC or gpB or both are essential for viability in Xanthomonas cells which contain an otherwise functional gum gene pathway.

The DNA defining transcription unit II (FIG. 11) is greater than 9 kb in length and codes for seven gene products. Insertion mutations in each of these genes have been isolated and characterized. The effects of insertions into the region of DNA defining gpJ are still uncertain. Preliminary results suggest that insertions in this region are probably lethal. Insertions at several places in the ORF defining gpG yield Xanthomonas cells that produced mucoid colonies which produce seemingly normal gum, although the quantity of gum produced may be somewhat reduced. The hydrophobic properties of the amino acids contained in gpG (FIG. 12) indicate that this gene product is probably a membrane protein. We cannot explain the apparent absence of any deleterious effects from insertion mutagenesis. Two of the genes (gpF and gpH) in transcription unit II play an obvious role in gum biosynthesis. The mutational phenotypes for these two genes indicate that gpF is acetylase and gpH is transferase III. Two of the genes, gpD and gpI, show a "no charger" mutational phenotype. This phenotype would be expected for the gene defining transferase I as well as any gene product involved in the regulatory control of transcription and/or translation of the gum genes. This phenotype might also be expected for a gene product that plays a structural role in maintaining an enzyme complex that is necessary for gum biosynthesis. Three of the expected five genes that define the transferase enzymes have been clearly identified from their mutational phenotypes. These are gpH, gpK, and gpM, which are transferase III, IV, and II, respectively (see FIG. 11). All three of these genes are composed of amino acids having a relatively low hydrophobicity profile (FIG. 12) and are located in the DNA on the right-hand side of the gum gene cluster. If it is assumed that these properties are general characteristics of the Xanthomonas transferase enzymes, then gpI is clearly the best candidate to be transferase I, leaving gpD as a putative regulatory or structural protein that is necessary for gum biosynthesis. Insertions into the region of DNA occupied by gpE are lethal in Xanthomonas cells which contain an otherwise intact gum gene pathway. As was also the case for the genes located in the 1.5 kb BamHI fragment (discussed above), gpE itself is not an essential protein for cell viability since several deletion strains which remove the region of the chromosome containing gpE are Gum⁻ but viable. It appears that gpE as well as gpC and/or gpB must be proteins that are necessary to prevent the accumulation of a product(s) (produced by the functioning gum genes) that is toxic unless it is further metabolized by the enzyme activities of gpE, gpC, and/or gpB. Thus, it seems likely that these proteins function in the polymerization and/or the transport of xanthan gum out of the cell.

The DNA following the transcription terminator at position 12570 and extending beyond the right-hand BamHI site of the 1.0 kb fragment (i.e., beyond the end of the sequenced DNA) defines what we believe is a third transcriptional unit. It should be noted that the transcription terminator defining the end of the transcription unit II has a rather short hairpin stem with a free energy strength (G) of only −4.4 kcal/mole. If the strength of the hairpin is related to the efficiency of transcription termination, then it is possible that transcriptional read-through occurs in this area. Transcription unit III clearly contains at least three genes defined by mutational phenotypes which indicate that their protein products are transferase IV (gpK), ketalase (gpL), and transferase II (gpM). The transferase II gene terminates at position 15284 which is 227 base pairs in from the left-hand BamHI site of the 1.0 kb BamHI fragment. Beyond this point extending rightward to the end of the sequenced DNA, the frame analysis curves show a non-random G+C distribution at the three nucleotide positions that is charateric of DNA that codes for a protein product. Although we were not able to clearly define the position, extent, or number of ORFs in this region, the frame analysis profile clearly indicates that this DNA contains at least one gene or possibly one gene and a small portion of a second gene, that spans the right-hand BamHI site of the 1.0 kb fragment extending into DNA that has not as yet been sequenced. On the other hand, insertions into the right-hand BamHI site of the 1.0 kb fragment as well as an insertion within the 1.0 kb fragment located about 300 base pairs to the right of the left-hand BamHI site both show a Gum⁺ phenotype.

In general, membrane proteins contain a high percentage of hydrophobic amino acid residues (i.e., Phe, Trp, Tyr, Ile, Leu, Met, and Val). To determine which of the gum gene proteins were likely to be located in the bacterial membranes, the computer was used to determine the proportion of hydrophobic amino acid residues as well as the distribution of hydrophobic regions within each protein sequence. These data are presented in FIG. 12 and show that proteins gpD, gpE, gpF, gpG, and gpJ contain a relatively high proportion of hydrophobic amino acid residues (greater than 40%) that are distributed throughout each amino acid sequence. Thus, these proteins are probably membrane proteins.

Example 18

This example shows that an enzyme encoded by the gum biosynthetic cluster is expressed in several alternate host strains of a different genus.

Antibodies which recognize Transferase III were purified by affinity chromatography and used to detect Transferase III on Western immunoblots. The production of the sera containing the antipeptide antibodies specific to the 40 kD protein identified as Transferase III is described in Example 11. One of these sera was absorbed to a peptide affinity column which consisted of the immunizing peptide which had been conjugated to CH-Sepharose via carbodiimide. The specific antipeptide antibodies were eluted from the affinity column with glycine-HCl (0.2M, pH 2.6) and neutralized with Tris. The purified serum recognized specifically Transferase III on Western immunoblots (supra).

The affinity-purified antipeptide antiserum was used to detect the presence or absence of Transferase III in cell lysates of alternate host strains containing a plasmid with (pRK290-H336) or without (pRK290-H11) the gum cluster DNA (Example 16). The strains tested are shown in Table 4.

The presence of Transferase III on the Western immunoblots indicated that the gum cluster DNA is being expressed in the alternate host strains. Transferase III was expressed in *Pseudomonas denitrificans, Pseudomonas stutzeri,* and *Pseudomonas putida* with pRK290-H336. The level of expression in *Pseudomonas stutzeri* was almost equivalent to that in *Xanthomonas campestris* itself. Expression of Transferase III off of pRK290-H336 in these alternative hosts is probably due to transcription of a messenger RNA that is initiated at an endogenous *X. campestris* promoter sequence located in the leftward end of the 4.7 kb BamHI fragment. The DNA sequence of the gum gene cluster, presented in Example 17, identifies two putative strong transcription terminators between Transferase III and the plasmid DNA of the vector pRK290. These terminator sequences, which occur at positions 814–844 and 3457–3493, would almost certainly prevent the transcription of Transferase III and any other downstream genes by RNA polymerase molecules that initiated transcription upstream of the terminators. Therefore, the transcript that contains the Transferase III gene must originate within the gum gene DNA and very likely originates from a putative promoter sequence located in the 4.7 kb BamHI fragment around position 3580. This argues that the transcription signals present in the gum cluster and normally used by *X. campestris* are also recognized and used in these alternative hosts. This implies that many or all of the gum genes carried on pRK290-H336 are transcribed and quite possibly translated in the alternative hosts.

The enzyme was not expressed from this plasmid construct in the *E. coli* strains tested. Evidently, the appropriate expression signals for *E. coli* must be present for the expression of xanthomonad DNA in *E. coli* . Example 13 showed expression of Transferase III from pp3, a plasmid with appropriate *E. coli* expression signals. It is expected that the other proteins encoded by the gum biosynthetic cluster can be expressed in a variety of alternate host strains.

TABLE 4

Expression of Transferase III in Alternate Host Strains

| | Transferase III by Western Immunoblot |
|---|---|
| *Xanthomonas campestris* S4L | ++ |
| *Xanthomonas campestris* X928 ($III^-$) | − |
| *Xanthomonas campestris* S4L (pRK290-H11) | ++ |
| *Xanthomonas campestris* S4L (pRK290-H336) | ++ |
| *Pseudomonas putida* (pRK290-H11) | − |
| *Pseudomonas putida* (pRK290-H336) | ± |
| *Pseudomonas fluorescens* (H11) | − |
| *Pseudomonas fluorescens* (H336) | + |
| *Pseudomonas stutzeri* (H11) | − |
| *Pseudomonas stutzeri* (H336) | ++ |
| *Pseudomonas denitrificans* (H11) | − |
| *Pseudomonas denitrificans* (H336) | + |
| *Pseudomonas cepacia* (H11) | − |
| *Pseudomonas cepacia* (H336) | − |
| *Enterobacter cloacae* (H11) | − |
| *Enterobacter cloacae* (H336) | − |
| *Escherichia coli* LE392 (H11) | − |
| *Escherichia coli* LE392 (H336) | − |
| *Escherichia coli* SM32 (H11) | − |
| *Escherichia coli* SM32 (H336) | − |
| Example 19 | |

This example describes methodology for regionally-directed mutagenesis of cloned gum gene DNA carried by recombinant plasmids pRK290-H336 and pRK290-HA3.

Regionally-directed mutagenesis was performed upon gum gene DNA carried by plasmids pRK290-H336 (H336) and pRK290-HA3 (HA3) described in Example 10. These cloned DNA segments were subjected to transposon mutagenesis in vivo and mutagenized in vitro through use of recombinant DNA technology to generate insertion and deletion mutations within the cloned *X. campestris* DNA. Plasmids carrying such mutations were transferred into *X. campestris* recipients including deletion mutant strains that lack all or nearly all of the gum gene DNA carried by H336. The resulting recipient strain carrying the mutant plasmid then immediately displays the gum phenotype that results from the plasmid mutation. This method eliminates the need for the gene replacement step utilized previously (Example 7).

Transposon mutagenesis employed a transposon described by Kleckner et al. in Gene 32:369–379 (1984) and termed by her "element 12" and here referred to as TnK12 (Kleckner's element 12). This transposon carries a DNA segment containing the kanamycin resistance determinant of Tn5. In addition, this DNA segment also carries a gene encoding resistance to streptomycin. This gene does not function in *E. coli* but has been shown to be active in other gram-negative bacteria. Previously we demonstrated that this gene was active in Xanthomonas and conferred a streptomycin-resistant phenotype when introduced, on a plasmid, into Xanthomonas. Therefore, movement of TnK12 into Xanthomonas ought to similarly confer simultaneous resistance to kanamycin and streptomycin, thus affording a strong selection for plasmids carrying TnK12 insertions.

TnK12 is carried in the chromosome of an *E. coli* strain, NK7133, which is resistant to rifampicin, the drug we most frequently use to select for *X. campestris* recipients in plasmid transfer experiments. Therefore, we isolated and used a chloramphenicol-resistant ($Cam^r$) derivative of the deletion strain X1107 (FIG. 15) as the recipient in our initial TnK12 transposition experiments. The first experiment was performed as follows. The plasmid pRK290-H336 was introduced into strain NK7133 by transformation using purified plasmid DNA. We then performed a triparental mating using NK7133 (pRK290-H336) as the donor, LE392 (pRK2013) as a mobilizer, and X1107 $Cam^r$ as the recipient. Fresh overnight cultures of these strains were washed once in LB, and 3 ml of each parent were mixed together and filtered through a 0.45 uM filter. The filter was incubated on an LB plate at 30° C. for 4 hours. The cells were then resuspended off the filter in 3.0 ml (total) of YM broth. Aliquots were plated out on YMG plates containing chloramphenicol, kanamycin, and streptomycin or streptomycin alone. Each of 15 plates of each type of medium was spread with 0.1 ml of the resuspended mating mix. Plates were incubated at 30° C. for 6–12 days and then scored. From this experiment, we ultimately obtained 100 $Kan^r$ $Str^r$ colonies. Most of these were Gum+ and wild-type in appearance. Seven were $Gum^-$, and five colonies were clearly mucoid but appeared to be morphologically distinct from wild-type $Gum^+$. Fourteen of these $Kan^r$ $Str^r$ derivatives of X1107 were mated in triparental crosses with *E. coli* HB101 and *X. campestris* S4L rif-101 (R68.45 tet::Tn7). The plasmid R68.45 tet::Tn7 is a tetracycline-sensitive derivative of the conjugally active plasmid R68.45. In the mating, this plasmid serves as the mobilizer which directs transfer of pRK290-H336::TnK12 derivatives to *E. coli* Because the plasmid gene encoding tetracycline resistance is inactivated (by virtue of the Tn7 insertion), selection for $Tet^r$ *E. coli* HB101 by selection for growth at 37° C. on 10 ug/ml of tetracycline results in specific selection for the transfer of the pRK290-H336 derivative into HB101. The analysis of the physical structure of these plasmids is technically easier in *E. coli* than Xanthomonas. The 14 matings all yielded Tet$^r$ derivatives of HB101 at frequencies ranging from $10^{-5}$ to $10^{-4}$ per recipient.

Figure 15A:
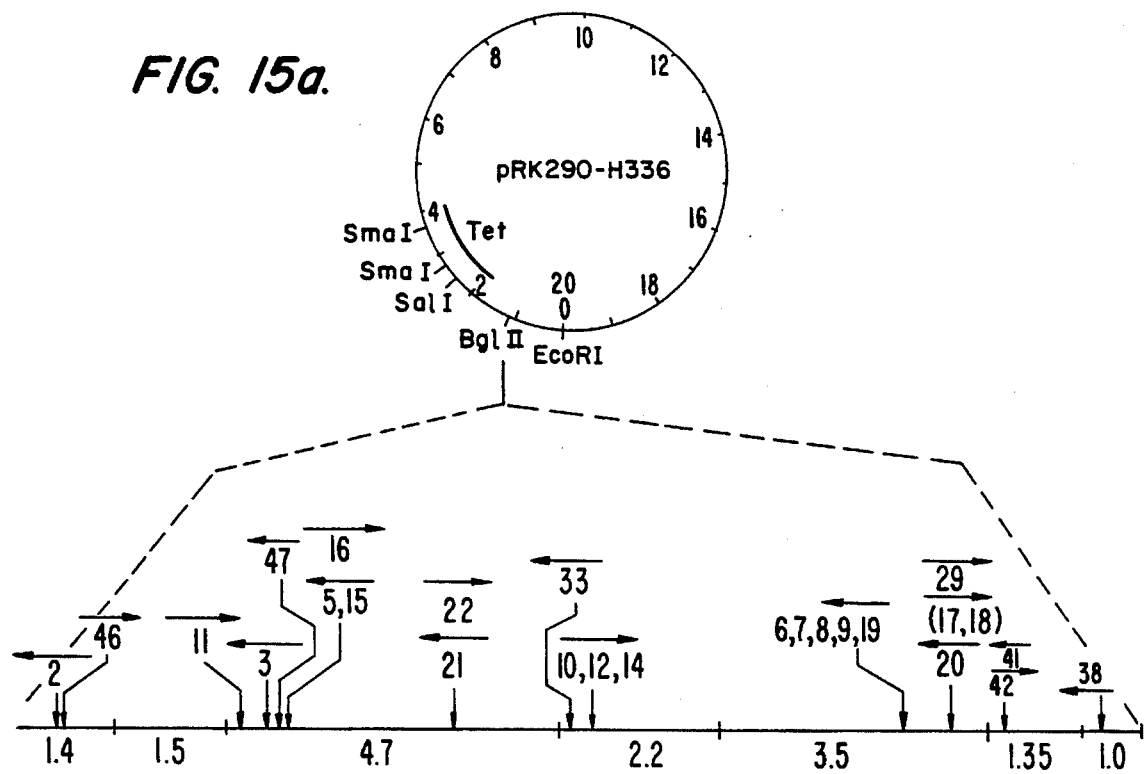
Figure 15B:
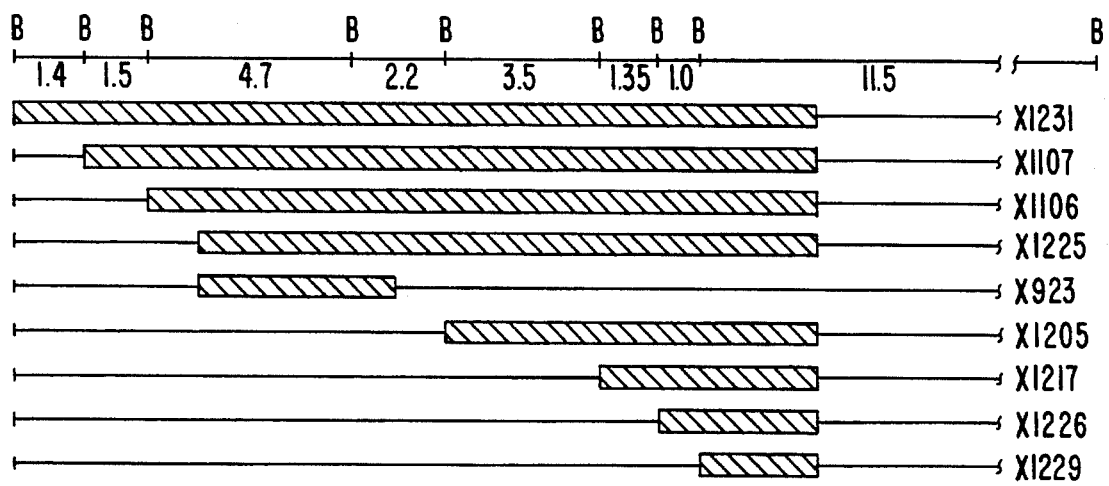
Figure 16A:
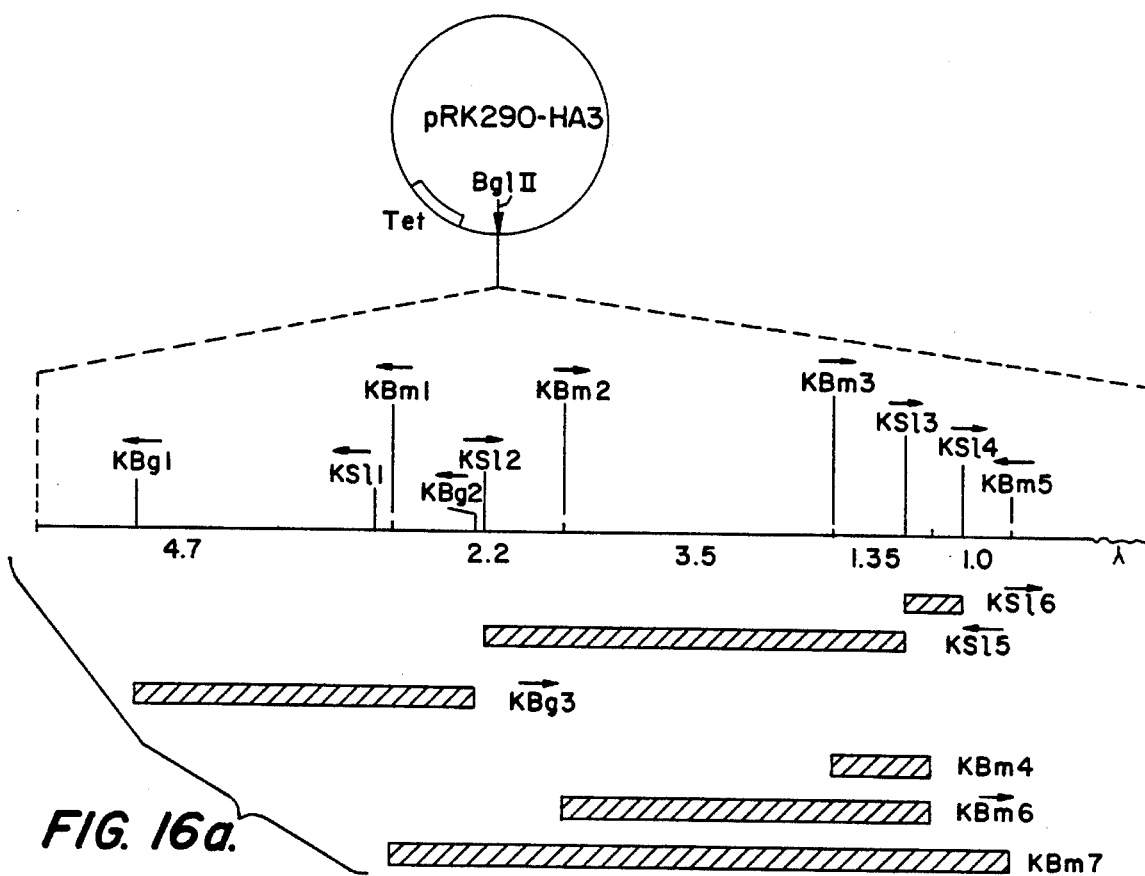
Figure 16B:
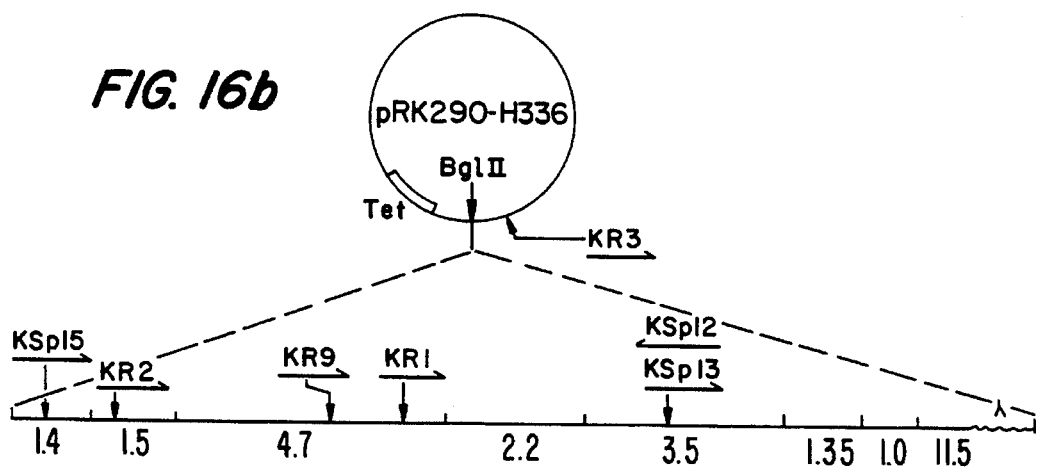

Plasmid DNAs were prepared from these stains and analyzed by restriction endonuclease digestions and agarose gel electrophoresis. Molecular weights of particular restriction fragments were determined by comparison of fragment mobility to the electrophoretic mobility of DNA fragment standards of known molecular weight. The pattern of restriction fragments produced by particular enzymes allowed us to determine the positions of the TnK12 insertions. These are shown in FIG. 15. Eleven insertions were found to be in the cloned gum gene DNA segment of pRK290-H336. All of these insertions resulted in a Gum$^-$ or mucoid phenotype when the particular mutant plasmid was present in X1107. Two Gum$^+$ plasmid derivatives were found to contain TnK12 insertions in the pRK290 portion of the molecule; this is consistent with the Gum$^+$ phenotype. One insertion (13) occurred in the vector but relatively near the gum gene DNA. This insertion conferred a slightly different Gum phenotype (morphologically), although the X1107 (pRK290-H336.13) strain produces large amounts of gum. This plasmid mutagenesis system allowed us to efficiently isolate and detect mutations within the cloned gum gene DNA. Using this procedure, with some minor variations, we isolated and characterized a set of TnK12 insertion mutations in pRK290-H336. In some experiments, a different *X. campestris* Gum$^-$ deletion strain was used. This deletion strain, X1231, (see FIG. 15) is deleted for all of the gum gene DNA carried by pRK290-H336. Some experiments also used different selection schemes. For example, in certain instances kanamycin plus streptomycin or streptomycin alone were used to select for transfer of TnK12 from *E. coli* into *X. campestris*. Ultimately, 45 TnK12 insertions into pRK290-H336 were isolated and analyzed. Most of these were found to occur with the gum genes and most were simple insertions, although some did show evidence of secondary DNA rearrangements as well.

Insertion and deletion mutations have also been isolated in pRK290-H336 and pKR290-HA3 by in vitro mutagenesis using a 1.3 kb restriction fragment of transposon Tn903. This fragment can be excised from a plasmid (pUC4-K) by a variety of restriction enzymes, including EcoRI, BamHI, SalI, AccI, HincII, and PstI. The HincII digestion yields a DNA fragment with blunt ends which can be modified by the addition of a DNA "linker" molecule in order to generate DNA ends that can be ligated into other restriction sites. In general, the procedure for insertion mutagenesis with this fragment is analogous to the procedure used to isolate insertion and deletion mutations within cloned gum gene DNA carried in plasmid pMW79 as described in Example 7. The plasmid pUC4-K was digested by the appropriate restriction endonuclease and the 1.3kb Kan$^r$ fragment was subsequently purified from preparative agarose gels by electrophoretic elution out of gel slices. When it was necessary to add a DNA linker molecule to the end of the Kan$^r$ fragment, a HincII digestion of pUC4-K was ligated with the desired linker molecule prior to the step of preparative electrophoresis. Subsequent purification of the Kan$^r$ DNA fragment removed the unligated linker molecules. The purified 1.3 kb Kan$^r$ fragment was then employed in in vitro mutagenesis experiments. In these experiments, partial restriction endonuclease digestions were performed on purified plasmid DNA by limiting the amount of restriction enzyme added to the reaction. By adding the appropriate amount of a given enzyme to a reaction, a high proportion of singly-cut linear molecules was obtained. The appropriate amount of each particular enzyme was determined empirically. Subsequently, the purified Kan$^r$ fragment is ligated to the partially digested plasmid DNA. Products of this ligation reaction are used to transform *E. coli*, and selection for kanamycin-resistant transformants selects for recombinant plasmid molecules which contain the Kan$^r$ DNA fragment inserted at some restriction site in the plasmid. Plasmid DNAs from Kan$^r$ transformants were analyzed to identify the location of particular insertion mutations. Deletion mutations were obtained when the Kan$^r$ DNA fragment was ligated to a plasmid molecule which had been cut two or more times by the restriction endonuclease. The insertion and deletion mutations constructed in plasmids H336 and HA3 are shown in FIG. 15.

In order to analyze the phenotypes of both in vivo- and in vitro-generated insertion mutations, the mutant plasmids were transferred via conjugation into *X. campestris* Gum$^-$ deletion mutants. Mutant derivatives of pRK290-H336 were transferred into the deletion strain X1231 where the Gum phenotype will reflect the affect of the insertion mutation carried by the plasmid. The phenotypes of many of the mutations have been analyzed in vivo and/or in vitro by methods described in Example 2. Plasmids carrying certain insertion mutations could not be transferred into deletion strain X1231. It is most probable that these insertion mutations are lethal or severely deleterious in *X. campestris*. These mutations and other lethal mutations are described in Example 20.

Example 20

This example describes the evidence for lethal mutations within the gum gene cluster and discusses the possible functions of the proteins inactivated by these lethal mutations.

As described in Example 19, mutations were isolated in gum gene DNA by in vitro insertion of the 1.3 kb Kan$^r$ fragment into the cloned gum gene DNA carried on pRK290-H336. These insertion mutant plasmids were constructed and analyzed in *E. coli*. In order to assess the Gum phenotypes of these mutants, we subsequently attempted to conjugally transfer mutant plasmids into the Gum$^-$ deletion strain X1231. Most mutant plasmids were efficiently transferred into X1231 via standard triparental matings. However, a few mutant plasmids were not transferred into X1231 or transferred at low frequency.

One such mutant plasmid was pRK290-H336.KR9 (KR9). This plasmid contains an insertion into the EcoRI site at position 6089 within the DNA sequence of the gum gene cluster and interrupts the open reading frame encoding gpE as described in Example 17. This is the only insertion isolated to date that interrupts this gene. Our initial attempt to transfer this insertion mutant plasmid, pRK290-H336.KR9, into X1231 failed, as did a repetition of this experiment. This result suggested the possibility that the KR9 insertion was a lethal mutation in *X. campestris*. We subsequently attempted to transfer KR9 into other *X. campestris* strains. A mating was performed with recipients X1231, X77 (wild type), and X1205, a Gum$^-$ deletion strain that lacks the gum DNA between the right-hand BamHI site of the 2.2 kb fragment and the HindIII site of the 11.5 kb BamHI fragment (FIG. 15). This strain has an intact copy of the 4.7 kb BamHI fragment and thus an intact copy of the gene inactivated by insertion KR9. In this experiment, KR9 was again not transferred into X1231. However, the plasmid was readily transferred into X77 and X1205. In the X1205 strain, the plasmid resulted in a "gummy" phenotype. This indicates that the gene functions missing from the chromosomal deletion of X1205 were supplied by the corresponding segment of cloned gum gene DNA on the plasmid. These results are consistent with the notion that the KR9 insertion is a lethal mutation. However, the gene inactivated by the KR9 mutation cannot be an essential gene, per se, because this gene is eliminated in many of the large deletion strains such as X1231, X1107, and X1106, which are viable. Thus, it seems that the KR9 mutation is lethal only when the rest of the gum biosynthetic pathway remains operative.

Similar results were observed for two insertion mutant plasmids that carried insertion mutations into the SpeI site at position 11,716 within the sequence. These mutant plasmids, pRK290-H336.KSp12 (KSp12) and pRK290-H336.KSp13 (KSp13), differ only in the orientation of the inserted Kan$^r$ DNA fragment. In standard triparental matings with a series of X. campestris recipients, both plasmids were efficiently transferred into the Gum$^+$ recipient X1229 and into the Gum$^-$ recipient X1217 which carries a wild-type copy of the 3.5 kb BamHI fragment in its chromosome and thus a wild-type copy of the gene encoding gpJ. Transfer of these two plasmids into the Gum$^-$ recipient X1205 was roughly three orders of magnitude lower, and transfer into the Gum$^-$ stain X1231 was lower still. The deletion in X1205 removes the 3.5 kb BamHI fragment but is otherwise identical to X1217. Strain X1231 is the largest gum gene deletion and eliminates all of the cloned gum gene DNA carried by pRK290-H336 and its insertion derivatives such as KSp12 and KSp13. These results indicate that the KSp12 and KSp13 insertions may be deleterious or lethal in X. campestris.

Using a somewhat different experimental approach, we have fortuitously discovered that a deletion of the 1.5 kb BamHI fragment appears to be lethal when the remainder of the gum gene cluster is intact. The plasmid pRK290-HA3 (HA3) as shown in FIG. 10 contains all the gum gene cluster DNA except the 1.4 kb and 1.5 kb BamHI fragments. We were interested in determining the phenotype of the deletion strain X1106 carrying the HA3 plasmid in order to determine the effect of breaking the gum cluster at the BamHI site delineating the 1.5 and 4.7 kb BamHI segments. Therefore, a derivative of HA3 (HA3.1) carrying a TnK12 insertion within the vector portion of HA3 was transferred into deletion X1106. This strain was found to be mucoid, which indicated that no gene essential for gum biosynthesis spans this BamHI site. Moreover, this shows that the cloned gum genes of HA3.1 are expressed off the plasmid.

However, a more interesting observation was made when we attempted to transfer HA3.1 into deletions X1107 and X1231. We hoped to analyze the phenotypes that would result from effective deletion of the 1.5 kb BamHI segment (in X1107) and deletion of both 1.5 and 1.4 kb BamHI fragments (in X1231). What we found was that HA3.1 could not be transferred into either deletion strain. This experiment was repeated and the result confirmed. HA3.1 was readily transferred into X1106 and X77 (wild type) but could not be transferred in X1107 or X1231. Thus, we conclude that the deletion of the 1.5 kb BamHI segment and deletion of the 1.5 kb and 1.4 kb BamHI segments are both lethal mutations. However, since the deletion strains X1107 and X1231 both lack the 1.5 kb BamHI fragment and are viable, it must be true that the genetic information eliminated by this deletion is not essential, per se. Again, this suggests that lack of the 1.5 kb BamHI segment becomes lethal when the rest of the gum gene pathway is operative.

We have obtained evidence that at least three different mutations in the gum gene cluster have lethal phenotypes. This lethality appears to be manifest only when at least some portion of the gum biosynthetic pathway remains active. Accumulation of a toxic product normally metabolized by the missing function(s) could account for this lethality. Under such a model, the activity of the gum biosynthetic pathway (or some portion of it) would result in lethality if certain other gene functions were absent. For example, such genes might encode the polymerase. Synthesis of $C_{55}$ lipid-linked pentasaccharide might be lethal because the $C_{55}$ lipid is absolutely required in at least one other cellular function that is essential for growth-cell wall biosynthesis. Thus, sequestering of the $C_{55}$ lipid into a non-metabolizable form might cause lethality. Alternatively, such genes might encode proteins involved in transport of the polymer out of the cell. Synthesis of the polymer in the absence of a transport system might also have deleterious effects on cell growth and could well be lethal. It is also possible that a "lethal" gene might encode Transferase V. No Transferase V mutants have been identified to date. Possibly the Transferase V defect could be lethal because it results in biosynthesis of a polymer (polytetramer) which is toxic to the microbe. For example, polytetramer might not be properly transported by the transport system that normally secretes xanthan.

The hypothesis that blocking gum biosynthesis at an early step in the pathway suppresses lethality could be tested. The experiment would be to construct double mutants between large Gum$^-$ deletions and sugar nucleotide mutants. A strain defective in UPD-glucose synthesis cannot initiate xanthan biosynthesis and therefore ought not to be subject to this lethality. Therefore, plasmids carrying the lethal insertion mutations ought to be readily transferred into and maintained by such double mutants. If this proved to be true, one could identify the functions encoded by the "lethal genes" through in vitro analysis of xanthan biosynthesis where the sugar nucleotides are supplied exogenously. It will be apparent to those skilled in the art that various modifications and variations can be made in the processes and products of the present invention. Thus, it is intended that the present invention cover the modifications and variations of this invention provided they come within the scope of the appended claims and their equivalents.

What is claimed is:

1. A recombinant-DNA mediated method for the production of a variant xanthan which is a polytrimer or non-acetylated polytrimer, said method comprising:

(a)

(i) for production of non-acetylated polytrimer, obtaining at least one vector comprising a Xanthomonas nucleotide sequence encoding transferase I, transferase II, transferase III, and polymerase, or (ii) for the production of polytrimer, obtaining at least one vector comprising a Xanthomonas nucleotide sequence encoding transferase I, transferase II, transferase III, acetylase and polymerase;

(b) transferring the vector or vectors into a gram negative bacterium, said bacterium producing UDP-glucose and GDP-mannose;

(c) culturing said gram negative bacterium under conditions appropriate for synthesis of said polytrimer or non-acetylated polytrimer; and (d) harvesting said polytrimer or non-acetylated polytrimer.

2. A recombinant-DNA mediated method for the production of a variant xanthan which is polytetramer or non-acetylated polytetramer, said method comprising:

(a)
(i) for production of non-acetylated polytetramer, obtaining at least one vector comprising a Xanthomonas nucleotide sequence encoding transferase I, transferase II, transferase III, transferase IV and polymerase, or (ii) for the production of polytetramer, obtaining at least one vector comprising a Xanthomonas nucleotide sequence encoding transferase I, transferase II, transferase III, transferase IV, acetylase and polymerase;

(b) transferring the vector or vectors into a gram negative bacterium, said bacterium producing UDP-glucose, UDP-glucoronic acid and GDP-mannose;

(c) culturing said gram negative bacterium under conditions appropriate for synthesis of said polytetramer or non-acetylated polytetramer; and (d) harvesting said polytetramer or non-acetylated polytetramer.

3. A recombinant-DNA mediated method for the production of a xanthan gum polypentamer, or a variant xanthan polypentamer which is non-acetylated polypentamer, non-pyruvated polypentamer, or non-acetylated and non-pyruvated polypentamer, said method comprising:

(a)
(i) for the production of non-acetylated and non-pyruvated polypentamer, obtaining at least one vector comprising a Xanthomonas nucleotide sequence encoding transferase I, transferase II, transferase III, transferase IV, transferase V and polymerase, (ii) for the production of non-pyruvated polypentamer, obtaining at least one vector comprising a Xanthomonas nucleotide sequence encoding transferase I, transferase II, transferase III, transferase IV, transferase V, acetylase and polymerase, (iii) for the production of non-acetylated polypentamer, obtaining at least one vector comprising a Xanthomonas nucleotide sequence encoding transferase I, transferase II, transferase III, transferase IV, transferase V, ketalase and polymerase, or (iv) for production of a xanthan gum polypentamer, obtaining at least one vector comprising a Xanthomonas nucleotide sequence encoding transferase I, transferase II, transferase III, transferase IV, transferase V, acetylase, ketalase and polymerase;

(b) transferring the vector or vectors into a gram negative bacterium, said bacterium producing UDP-glucose, UDP-glucuronic acid and GDP-mannose;

(c) culturing said gram negative bacterium under conditions appropriate for synthesis of said xanthan gum polypentamer, non-pyruvated polypentamer, non-acetylated polypentamer, or non-acetylated and non-pyruvated polypentamer; and (d) harvesting said xanthan gum polypentamer, non-pyruvated polypentamer, non-acetylated polypentamer, or non-acetylated and non-pyruvated polypentamer.

4. The method of claim 1, wherein the nucleotide sequence for production of non-acetylated polytrimer or the nucleotide sequence for production of polytrimer is a *Xanthomonas campestris* nucleotide sequence.

5. The method of claim 2, wherein the nucleotide sequence for production of non-acetylated polytetramer or the nucleotide sequence for production of polytetramer is a *Xanthomonas campestris* nucleotide sequence.

6. The method of claim 3, wherein the nucleotide sequence for production of xanthan gum polypentamer, non-acetylated polypentamer, non-pyruvated polypentamer, or non-acetylated and non-pyruvated polypentamer is a *Xanthomonas campestris* nucleotide sequence.

7. The method of claim 1, wherein said gram negative bacterium is selected from the group consisting of *Pseudomonas pudita, Pseudomonas cepacia, Pseudomonas denitrificans, Pseudomonas fluorescens, Pseudomonas stutzeri, Escherichia coli*, and *Enterobacter cloacae*.

8. The method of claim 2, wherein said gram negative bacterium is selected from the group consisting of *Pseudomonas pudita, Pseudomonas cepacia, Pseudomonas denitrificans, Pseudomonas fluorescens, Pseudomonas stutzeri, Escherichia coli*, and *Enterobacter cloacae*.

9. The method of claim 3, wherein said gram negative bacterium is selected from the group consisting of *Pseudomonas pudita, Pseudomonas cepacia, Pseudomonas denitrificans, Pseudomonas fluorescens, Pseudomonas stutzeri, Escherichia coli*, and *Enterobacter cloacae*.

10. The method of claim 1, wherein said gram negative bacterium is Xanthomonas.

11. The method of claim 2, wherein said gram negative bacterium is Xanthomonas.

12. The method of claim 3, wherein said gram negative bacterium is Xanthomonas.

13. A vector comprising a nucleotide sequence for production of non-acetylated polytrimer or a nucleotide sequence for production of polytrimer wherein:

(a) said nucleotide sequence for production of non-acetylated polytrimer comprises a Xanthomonas nucleotide sequence encoding transferase I, transferase II, transferase III, and polymerase; and (b) said nucleotide sequence for the production of polytrimer comprises a Xanthomonas nucleotide sequence encoding transferase I, transferase II, transferase III, acetylase, and polymerase.

14. A vector comprising a nucleotide sequence for production of non-acetylated polytetramer or a nucleotide sequence for production of polytetramer wherein:

(a) said nucleotide sequence for production of non-acetylated polytetramer comprises a Xanthomonas nucleotide sequence encoding transferase I, transferase II, transferase III, transferase IV, and polymerase; and (b) said nucleotide sequence for the production of polytetramer comprises a Xanthomonas nucleotide sequence encoding transferase I, transferase II, transferase III, transferase IV, acetylase, and polymerase.

15. A vector comprising a nucleotide sequence for production of xanthan gum polypentamer, a nucleotide sequence for production of non-acetylated polypentamer, a nucleotide sequence for production of non-pyruvated polypentamer, or a nucleotide sequence for production of non-acetylated and non-pyruvated polypentamer, wherein:

(a) said nucleotide sequence for the production of non-acetylated and non-pyruvated polypentamer comprises a Xanthomonas nucleotide sequence encoding transferase I, transferase II, transferase III, transferase IV, transferase V, and polymerase;

(b) said nucleotide sequence for the production of non-pyruvated polypentamer comprises a Xanthomonas nucleotide sequence encoding transferase I, transferase II, transferase III, transferase IV, transferase V, acetylase, and polymerase;

(c) said nucleotide sequence for the production of non-acetylated polypentamer comprises a Xanthomonas nucleotide sequence encoding transferase I, transferase II, transferase III, transferase IV, transferase V, ketalase, and polymerase; and (d) said nucleotide sequence for production of a xanthan gum polypentamer comprises a Xanthomonas nucleotide sequence encoding transferase I, transferase II, transferase III, transferase IV, transferase V, acetylase, ketalase, and polymerase.

16. The vector of claim 13, wherein the nucleotide sequence for production of non-acetylated polytrimer or the nucleotide sequence for production of polytrimer is a *Xanthomonas campestris* nucleotide sequence.

17. The vector of claim 14, wherein the nucleotide sequence for production of non-acetylated polytetramer or the nucleotide sequence for production of polytetramer is a *Xanthomonas campestris* nucleotide sequence.

18. The vector of claim 15, wherein the nucleotide sequence for production of xanthan gum polypentamer, non-acetylated polypentamer, non-pyruvated polypentamer, or non-acetylated and non-pyruvated polypentamer is a *Xanthomonas campestris* nucleotide sequence.

19. A microorganism comprising the vector of claim 13.
20. A microorganism comprising the vector of claim 14.
21. A microorganism comprising the vector of claim 15.
22. The microorganism of claim 19, wherein said microorganism is Xanthomonas.
23. The microorganism of claim 20, wherein said microorganism is Xanthomonas.
24. The microorganism of claim 21, wherein said microorganism is Xanthomonas.
25. The microorganism of claim 19, wherein said microorganism is a gram negative bacterium.
26. The microorganism of claim 20, wherein said microorganism is a gram negative bacterium.
27. The microorganism of claim 21, wherein said microorganism is a gram negative bacterium.
28. The microorganism of claim 19, wherein said microorganism is selected from the group consisting of *Pseudomonas putida, Pseudomonas cepacia, Pseudomonas denitrificans, Pseudomonas fluorescens, Pseudomonas stutzeri, Escherichia coli*, and *Enterobacter cloacae*.
29. The microorganism of claim 20, wherein said microorganism is selected from the group consisting of *Pseudomonas putida, Pseudomonas cepacia, Pseudomonas denitrificans, Pseudomonas fluorescens, Pseudomonas stutzeri, Escherichia coli*, and *Enterobacter cloacae*.
30. The microorganism of claim 21, wherein said *Pseudomonas putida, Pseudomonas cepacia, Pseudomonas denitrificans, Pseudomonas fluorescens, Pseudomonas stutzeri, Escherichia coli*, and *Enterobacter cloacae*.
31. A recombinant-DNA mediated method for the production of xanthan, and variant xanthan polysaccharide which is a non-acetylated polytrimer, polytrimer, non-acetylated polytetramer, polytetramer, non-acetylated and non-pyruvated xanthan gum polypentamer, non-pyruvated xanthan gum polypentamer, or non-acetylated xanthan gum polypentamer, said method comprising:

(a) obtaining at least one vector comprising a Xanthomonas nucleotide sequence encoding at least one enzyme selected from the group consisting of transferase I, transferase II, transferase III, transferase IV, transferase V, acetylase, ketalase and polymerase;

(b) transferring the vector or vectors into Xanthomonas;

(c) culturing said Xanthomonas under conditions appropriate for synthesis of said xanthan or variant xanthan polysaccharide; and (d) harvesting said xanthan or variant xanthan polysaccharide.

32. The method of claim 31, wherein said method produces non-acetylated polytrimer.
33. The method of claim 31, wherein said method produces polytrimer.
34. The method of claim 31, wherein said method produces non-acetylated polytetramer.
35. The method of claim 31, wherein said method produces polytetramer.
36. The method of claim 31, wherein said method produces non-acetylated and non-pyruvated xanthan gum polypentamer.
37. The method of claim 31, wherein said method produces non-pyruvated xanthan gum polypentamer.
38. The method of claim 31, wherein said method produces non-acetylated xanthan gum polypentamer.
39. The method of claim 31, wherein said method produces xanthan gum polypentamer.
40. The method of claim 31, wherein said nucleotide sequence encodes at least two enzymes selected from the group consisting of transferase I, transferase II, transferase III, transferase IV, transferase V, acetylase, ketalase and polymerase.
41. The method of claim 31, wherein said nucleotide sequence encodes at least three enzymes selected from the group consisting of transferase I, transferase II, transferase III, transferase IV, transferase V, acetylase, ketalase and polymerase.
42. The method of claim 31, wherein said nucleotide sequence encodes at least four enzymes selected from the group consisting of transferase I, transferase II, transferase III, transferase IV, transferase V, acetylase, ketalase and polymerase.
43. A vector comprising a nucleotide sequence for the production of xanthan and a variant xanthan polysaccharide which is a non-acetylated polytrimer, polytrimer, non-acetylated polytetramer, polytetramer, non-acetylated and non-pyruvated xanthan gum polypentamer, non-pyruvated xanthan gum polypentamer, or non-acetylated xanthan gum polypentamer, wherein said nucleotide sequence comprises a Xanthomonas nucleotide sequence encoding at least one enzyme selected from the group consisting of transferase I, transferase II, transferase III, transferase IV, transferase V, acetylase, ketalase, and polymerase.
44. A microorganism comprising the vector of claim 43.
45. A microorganism of the strain *E. coli* LE392 (pRK290-H 336).
46. A microorganism of the strain *E. coli* LE392 (pX209).
47. The plasmid pX209.
48. The plasmid pRK290-H336.

* * * * *